US012709607B2

(12) United States Patent
Hatcher

(10) Patent No.: US 12,709,607 B2
(45) Date of Patent: Aug. 18, 2026

(54) POTENT AND SELECTIVE IRREVERSIBLE INHIBITORS OF IRAK1

(71) Applicant: Dana-Farber Cancer Institute, Inc., Boston, MA (US)

(72) Inventor: John M. Hatcher, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 945 days.

(21) Appl. No.: 17/906,938

(22) PCT Filed: Mar. 22, 2021

(86) PCT No.: PCT/US2021/023509
§ 371 (c)(1),
(2) Date: Sep. 21, 2022

(87) PCT Pub. No.: WO2021/194982
PCT Pub. Date: Sep. 30, 2021

(65) Prior Publication Data

US 2024/0043405 A1 Feb. 8, 2024

Related U.S. Application Data

(60) Provisional application No. 62/993,369, filed on Mar. 23, 2020.

(51) Int. Cl.
*C07D 401/14* (2006.01)
*A61K 45/06* (2006.01)
*C07D 401/04* (2006.01)
*C07D 413/14* (2006.01)

(52) U.S. Cl.
CPC ............ *C07D 401/14* (2013.01); *A61K 45/06* (2013.01); *C07D 401/04* (2013.01); *C07D 413/14* (2013.01)

(58) Field of Classification Search
CPC .................................................... C07D 401/14
See application file for complete search history.

(56) References Cited

U.S. PATENT DOCUMENTS

2018/0111917 A1 4/2018 Tso et al.

FOREIGN PATENT DOCUMENTS

WO WO 2018/098367 A1 5/2018
WO WO 2019/238102 A1 12/2019

OTHER PUBLICATIONS

Wright et.al (Dalton Trans., 2014, 43, 17006) (Year: 2014).*
Hatcher et al., "Discovery of a Selective, Covalent IRAK1 Inhibitor with Antiproliferative Activity in MYD88 Mutated B-Cell Lymphoma", ACS Medicinal Chemistry Letters 11(11):2238-2243 (2020).
International Search Report and Written Opinion for International Application No. PCT/US2021/023509, mailed Jun. 8, 2021, 7 pages.
Park et al., "Metabolism of Fluorine-Containing Drugs", *Annual Review of Pharmacology and Toxicology* 41:443-470 (2001).

* cited by examiner

*Primary Examiner* — John S Kenyon
*Assistant Examiner* — Rehana Ismail
(74) *Attorney, Agent, or Firm* — Nielsen IP Law LLC

(57) ABSTRACT

The disclosure relates to compounds that act as irreversible inhibitors interleukin 1 (IL-1) receptor-associated kinases (IRAKs); pharmaceutical compositions comprising the compounds; and methods of treating or preventing kinase-mediated disorders, including cancer and other proliferation diseases.

17 Claims, No Drawings

POTENT AND SELECTIVE IRREVERSIBLE INHIBITORS OF IRAK1

RELATED APPLICATIONS

This application claims priority to U.S. Provisional Application No. 62/993,369 filed on Mar. 23, 2020, the entire content of which is hereby incorporated in its entirety.

BACKGROUND

Interleukin 1 (IL-1) receptor-associated kinases (IRAKs) are serine/threonine kinases that play critical roles in initiating innate immune responses against foreign pathogens. Altogether there are four IRAK kinases: IRAK1 and IRAK4, which are catalytically active kinases, and IRAK2 and IRAK3, which are believed to be catalytically inactive and are hence classified as "pseudokinases" (Flannery, S., et al. *Biochemical Pharmacology,* 2010, 80(12), 1981-1991). IRAK1 is ubiquitously expressed with its highest expression observed in blood and immune tissues (e.g., bone marrow, lymph nodes, thymus, and peripheral blood) and hematological malignancies (Cao, Z. D., et al, *Science* 1996, 271(5252), 1128-1131). IRAK signaling contributes to multiple signaling pathways downstream of the Toll-interleukin receptors (TIRs) that ultimately regulate NF-κB and IFN regulatory factors (IRFs) (Rao, N., et al. *Molecular and Cellular Biology* 2005, 25(15), 6521-6532). In the case of NF-κB, IRAK1 mediates the downstream signals of TIRs through an interaction with MYD88 that is rapidly recruited to the receptor upon ligand binding to either IL-1R or a TLR. Subsequent phosphorylation on IRAK1 by upstream signals or through autophosphorylation is the key post-translational modification and hallmark of its activation, which allows IRAK1 to bind to TRAF6 resulting in release of the IRAK1 homodimer from MYD88 and downstream NF-κB activation (Jain, A., et al, *Frontiers in Immunology* 2014, 5).

The participation of IRAK1 in signaling networks of the innate immune response makes it a critical regulator of inflammation (Ringwood, L., et al. *Cytokine* 2008, 42(1), 1-7), antiviral response (Wong, W., *Science of Signaling* 2011, 4(183), ec203), and subsequent activation of the adaptive immune response (Gottpati, S., et al., *Cellular Signaling* 2008, 20(2), 269-276). Consequently, an extensive investigation into physiological and pathological functions of IRAK1 in regulating these processes has been performed. In particular, these studies have implicated IRAK1 inhibition as potential treatment for myocardial contractile dysfunction following burn (Thomas, J A., et al., *American Journal of Physiology-Heart and Circulatory Physiology* 2002, 283(2), H829-H836), autoimmune conditions associated with hyper inflammation (Deng, C., et al. *Journal of Immunology* 2003, 170(6), 2833-2842; Jacob, C. O., *Proceedings of the National Academy of Sciences of the U.S. Pat. No.* 2009, 106(15), 6256-6261), myocardial dysfunction (Thomas J. A., et al. *American Journal of Physiology-Heart and Circulatory Physiology* 2003, 285(2), H597-H606), microbial septic response (Chandra, R., et al. *Inflammation* 2013, 36(6), 1503-1512), human myelodysplastic syndrome (MDS), and acute myeloid leukemia (AML). IRAK1 is also overexpressed and hyperphosphorylated in a subset of breast cancers: in particular, triple-negative breast cancer (TNBC).

Furthermore, in Waldenström macroglobulinemia cells, the MYD88 L265P somatic mutation is highly prevalent and responsible for malignant growth through activation of nuclear factor NF-κB. Two downstream signaling branches, one including BTK and one including IRAK1, regulate NF-κB activation in Myd88L265P expressing WM cell lines. Genetic knockdown of either BTK or IRAK1 leads to modest cell killing. Although IRAK1 was identified over twenty years ago, and its critical function in autoimmunity and inflammation has been widely recognized, medicinal chemistry efforts directed at the development of selective inhibitors of IRAK1 have not been reported.

SUMMARY

Provided herein is a compound of Formula I:

(I)

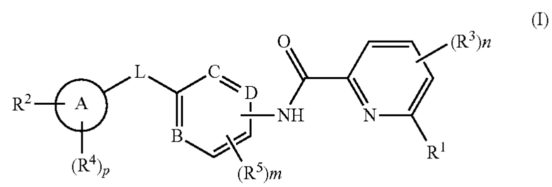

or a pharmaceutically acceptable salt thereof, wherein the variables are defined herein.

In an embodiment, the compound of Formula I is a compound of Formula II:

(II)

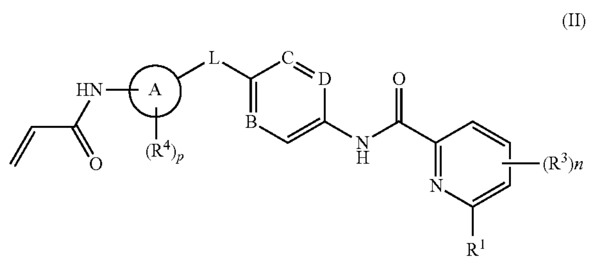

or a pharmaceutically acceptable salt thereof.

In another embodiment, the compound of Formula I is a compound of Formula III:

(III)

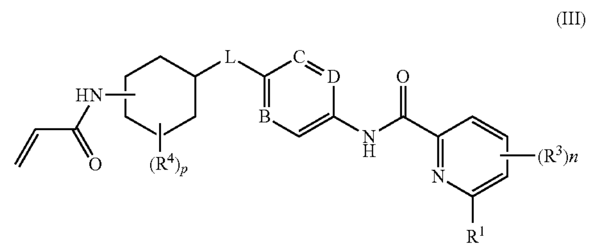

or a pharmaceutically acceptable salt thereof.

In yet another embodiment, the compound of Formula I is a compound of Formula IV:

(IV)

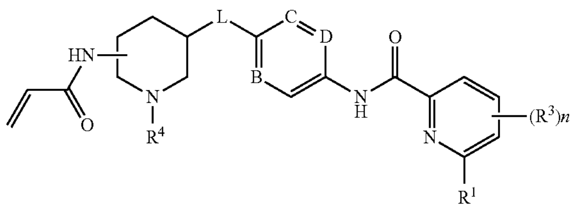

or a pharmaceutically acceptable salt thereof.

In still another embodiment, the compound of Formula I is a compound of Formula V:

(V)

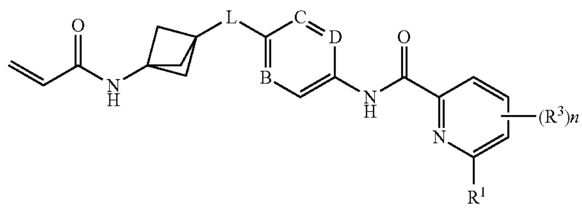

or a pharmaceutically acceptable salt thereof.

In an embodiment, the compound of Formula I is a compound of Formula VI:

(VI)

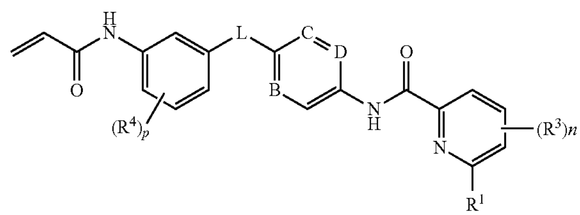

or a pharmaceutically acceptable salt thereof.

In another embodiment, the compound of Formula I is a compound of Formula VII:

(VII)

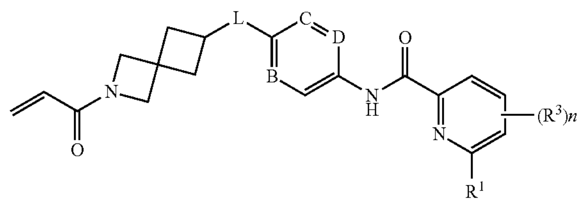

or a pharmaceutically acceptable salt thereof.

In another aspect, provided herein are pharmaceutical compositions comprising any of the compounds disclosed herein, or a pharmaceutically acceptable salt thereof, and at least one pharmaceutically acceptable carrier.

In yet another aspect, provided herein is a method of inhibiting a kinase comprising administering to a subject in need thereof an effective amount of a compound of Formula or a pharmaceutical composition comprising a compound of Formula I and a pharmaceutically acceptable carrier.

In an aspect, provided herein is a method of treating a proliferation disease, comprising administering to a subject in need thereof an effective amount of a compound of Formula I or a pharmaceutical composition comprising a compound of Formula I and a pharmaceutically acceptable carrier.

The present disclosure also provides a kit comprising a compound capable of inhibiting a kinase selected from a compound of Formula I, or a pharmaceutically acceptable salt thereof, and instructions for use in treating a proliferative disease.

DETAILED DESCRIPTION

IRAK1 is a serine/threonine kinase that was originally identified in 1994. It is ubiquitously expressed with its highest expression observed in blood and immune tissues (for example, bone marrow, lymph nodes, thymus and peripheral blood) and hematological malignancies. IRAK signaling contributes to multiple signaling pathways downstream of the Toll-interleukin receptors (TIRs) that ultimately regulate NF-κB and IFN regulatory factors (IRFs). In the case of NF-κB, IRAK1 mediates the downstream signals of TIRs through an interaction with MYD88, which is rapidly recruited to the receptor upon ligand binding to either IL-1R or a TLR. Subsequent phosphorylation on IRAK1 by upstream signals or through autophosphorylation is the key post-translational modification and hallmark of its activation, which allows IRAK1 to bind to TRAF6 resulting in release of the IRAK1 homodimer from MYD88 and downstream NF-κB activation.

The participation of IRAK1 in signaling networks of the innate immune response has defined the enzyme as a critical regulator of inflammation, the antiviral response, and the subsequent activation of the adaptive immune response. Consequently, an extensive investigation into physiological and pathological functions of IRAK1 in regulating these processes has been performed. In particular, these studies have implicated IRAK1 inhibition as potential treatment for myocardial contractile dysfunction following burn, autoimmune conditions associated with hyper inflammation, myocardial dysfunction, microbial septic response, human myelodysplastic syndrome (MDS), and acute myeloid leukemia (AML). In Waldenström macroglobulinemia cells, the MYD88 L265P somatic mutation is highly prevalent and responsible for malignant growth through activation of nuclear factor NF-κB. Two downstream signaling branches, one including BTK and one including IRAK1, both regulate NF-κB activation in Myd881_265P expressing WM cell lines.

IRAK1 inhibitors should be pursued for the disease since genetic knockdown of either BTK or IRAK1 leads to modest cell killing; and IRAK1 is activated in viable cells isolated from WM patient currently receiving Ibrutinib therapy WM cell lines, and primary patient samples treated with an IRAK114 inhibitor and a BTK inhibitor display augmented inhibition of NF-κB signaling and more robust cell killing. Although IRAK1 was identified over twenty years ago, and its critical function in autoimmunity and inflammation has been widely recognized, medicinal chemistry efforts directed at the development of selective inhibitors of IRAK1 have not been reported. Thus, it is important to develop selective inhibitors of IRAK (e.g., IRAK1 and IRAK4) for use as research tools as well as therapeutic agents in the treatment of diseases.

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those weft-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises bringing into contact with IRAK an effective amount of a compound disclosed herein for conditions related to cancer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa, 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent; diluent; excipient, thickening agent, solvent or encapsulating material; involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars; such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol;

phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genera, Ed., Mack Publishing Co., 1985, Easton, PA), which is incorporated herein by reference.

An "oral dosage form" includes a unit dosage form prescribed or intended for oral administration. In an embodiment of the pharmaceutical combinations provided herein, the IRAK inhibitors disclosed herein is administered as an oral dosage form.

As used herein, the term "IRAK" refers to interleukin 1 (IL-1) receptor-associated kinases and may refer to the wild-type receptor or to a receptor containing one or more mutations.

As used herein, the term "alkyl," by itself or as part of another substituent means, unless otherwise stated, a straight or branched chain hydrocarbon having the number of carbon atoms designated (i.e., $C_1$-$C_6$alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_5$ alkyl include ethyl, methyl, isopropyl, isobutyl, n-pentyl, and n-hexyl.

As used herein, the term "alkylamine" refers to the group —N(H)-alkyl or —N(alkyl)$_2$, wherein alkyl is defined supra.

As used herein, the phrase "nitrogen protecting group" refers to a functional group introduced into a molecule by chemical modification of a nitrogen atom to obtain chemoselectivity in a subsequent chemical reaction. Examples of nitrogen protecting groups include, but are not limited to, carbobenzyloxy (Cbz), tert-butyloxycarbonyl (Boc), 9-fluorenylmethyloxycarbonyl (Fmoc), acetyl (Ac), benzoyl (Bz), tosyl (Ts), and benzyl (Bn).

The term "alkylene," employed alone or in combination with other terms, refers to a divalent alkyl linking group. An alkylene group formally corresponds to an alkane with two C H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "alkenyl" refers to a monovalent group derived from a hydrocarbon moiety containing, in certain embodiments, from two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term "alkynyl" refers to a monovalent group derived from a hydrocarbon moiety containing, in certain embodiments, from two to six, or two to eight carbon atoms having at least one carbon-carbon triple bond. The alkynyl group may or may not be the point of attachment to another group. The term "alkynyl" includes, but is not limited to, ethynyl, 1-propynyl, 1-butynyl, heptynyl, octynyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, spiro[3.3] heptanyl, and bicyclo[1.1.1]pentyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]-hexanyl, 5-azabicyclo [2.1.1]hexanyl, 6-azabicyclo[3.1.1] heptanyl, 2-azabicyclo [2.2.1]-heptanyl, 3-aza-bicyclo[3.1.1]heptanyl, 2-azabicyclo [3.1.1]heptanyl, 3-azabicyclo[3.1.0]-hexanyl, 2-azabicyclo-[3.1.0]hexanyl, 3-azabicyclo[3.2.1]octanyl, 8-azabicyclo [3.2.1]octanyl, 3-oxa-7-azabicyclo[3.3.1]-nonanyl, 3-oxa-9-azabicyclo[3.3.1]nonanyl, 2-oxa-5-azabicyclo-[2.2.1] heptanyl, 6-oxa-3-aza-bicyclo[3.1.1]heptanyl, 2-azaspiro [3.3]heptanyl, 2-oxa-6-azaspiro[3.3]heptanyl, 2-oxaspiro [3.3]-heptanyl, 2-oxaspiro[3.5]nonanyl, 3-oxaspiro[5,3]-nonanyl, 2-azaspiro[3.3]heptane, and 8-oxabicyclo[3.2.1] octanyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8 tetrahydroisoquinolinyl, 5,6,7,8-tetrahydroquinolinyl, 6,7-dihydro-5H-cyclopenta[b]pyridinyl, 6,7-dihydro-5H-cyclo-penta[c]pyridinyl, 1,4,5,6-tetrahydrocyclopenta[c]pyrazolyl, 2,4,5,6-tetrahydrocyclopenta[c]-pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

Provided herein are compounds that are irreversible inhibitors of interleukin 1 receptor-associated kinase (IRAK) useful in the treatment of kinase-mediated disorders; including cancer and other proliferation diseases.

In an aspect, provided herein is a compound of Formula I:

(I)

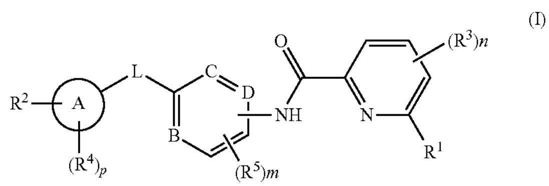

or a pharmaceutically acceptable salt thereof;

wherein

A is selected from the group consisting of 3-8 membered cycloalkyl, 3-8 membered heterocycloalkyl, 6-10 membered aryl, and 5-10 membered heteroaryl;

B, C, and D are each, independently, CH, $CR^5$, or N, provided that B, C, and D are not all CH when m is 0;

L is selected from the group consisting of absent, $C_1$-$C_6$ alkyl, 5-10 membered heteroaryl,

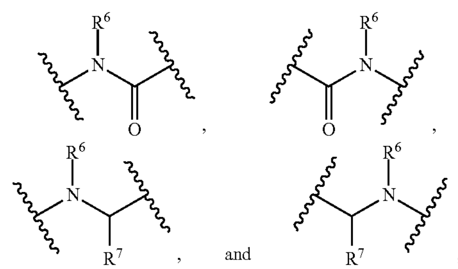

$R^1$ is 5-10 membered heteroaryl optionally substituted one or two times with $R^8$;

$R^3$ and $R^4$ are independently, at each occurrence, selected from the group consisting of hydrogen, halogen, $C_1$-$C_6$ alkyl, $C(O)C_1$-$C_5$ alkyl, $C_2$-$C_6$ alkenyl, $C_2$-$C_6$ alkynyl, 3-8 membered cycloalkyl, 3-8 membered heterocycloalkyl, 6-10 membered aryl, 5-10 membered heteroaryl, $OR^9$, $N(R^9)_2$, and $SR^9$, wherein alkyl, alkenyl, alkynyl, cycloalkyl, heterocycloalkyl, aryl, and heteroaryl are optionally substituted with one, two, or three $R^9$;

$R^5$ is independently, at each occurrence, selected from the group consisting of halogen, $C_1$-$C_6$ alkyl, $C(O)C_1$-$C_6$ alkyl, $C_2$-$C_6$ alkenyl, $C_2$-$C_6$ alkynyl, $OR^9$, $N(R^9)_2$, and $SR^9$, wherein alkyl is optionally substituted with one, two, or three halogen;

$R^6$ is independently, at each occurrence, selected from the group consisting of hydrogen, $C_1$-$C_6$ alkyl, and a nitrogen protecting group, wherein alkyl is optionally substituted with $R^9$;

$R^7$ is selected from the group consisting of hydrogen, $C_1$-$C_6$ alkyl OH, ON, $NO_2$, halogen, $C_1$-$C_5$ alkoxy, and $C_1$-$C_6$ alkylamine, wherein alkyl is optionally substituted with one, two, or three halogen;

$R^8$ is selected from the group consisting of $C_1$-$C_6$ alkyl, OH, ON, $NO_2$, halogen, $C_1$-$C_6$ alkoxy, and $C_1$-$C_6$ alkylamine, wherein alkyl is optionally substituted one, two, or three times with halogen, OH, and $NH_2$;

$R^9$ is independently, at each occurrence, selected from the group consisting of hydrogen, halogen, $C_1$-$C_6$ alkyl, $C(O)C_1$-$C_6$ alkyl, $C_2$-$C_6$ alkenyl, $C_2$-$C_6$ alkynyl, 3-8 membered cycloalkyl, 3-8 membered heterocycloalkyl, 6-10 membered aryl, and 5-10 membered heteroaryl;

alternatively, two $R^9$, together with the atoms to which they are attached form a 3-8 membered heterocycloalkyl;

$R^2$ is selected from the group consisting of:

(i-1)

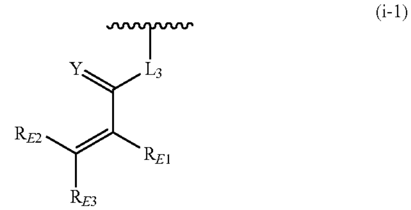

(i-2)

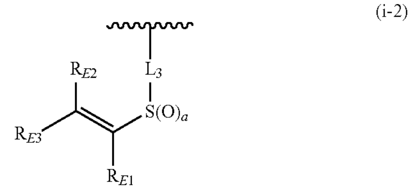

-continued
(i-3)
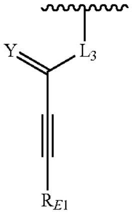
(i-4)
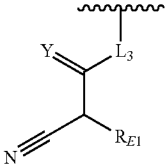
(i-6)
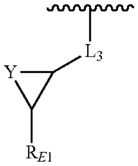
(i-7)
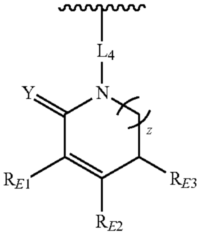
(i-8)
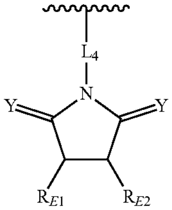
(i-9)
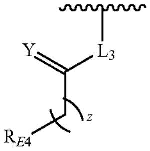
(i-11)
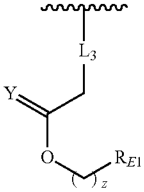
(i-12)
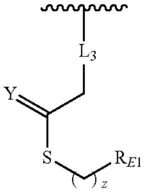
-continued
(i-13)
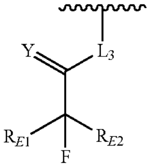
(i-14)
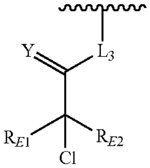
(i-16)
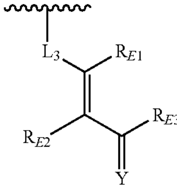
(i-17)
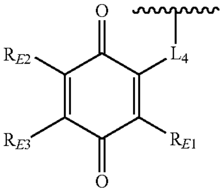
(i-18)
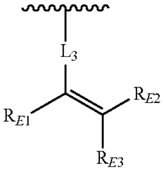
(i-19)
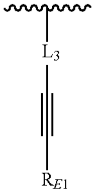
(i-21)
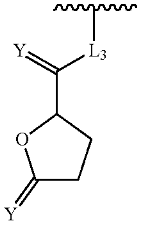
(i-22)
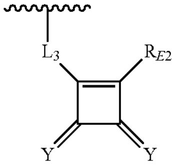

-continued (i-23)

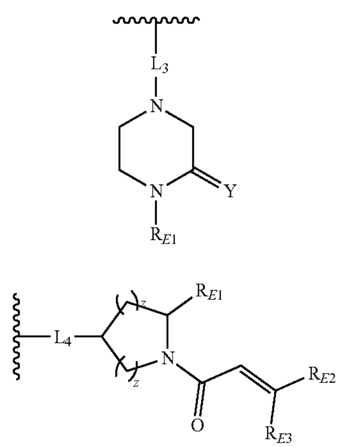

(i-24)

(i-26)

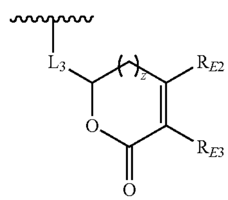

(i-27)

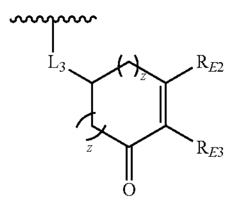

(i-28)

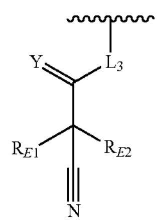

(i-29)

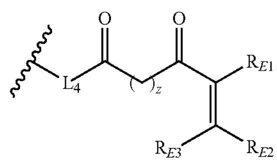

(i-31)

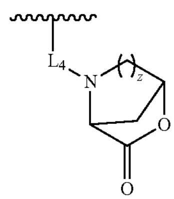

(i-32)

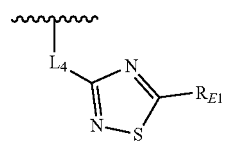

-continued (i-33)

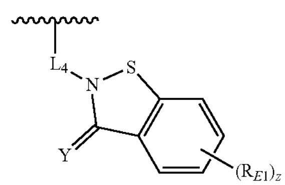

(i-34)

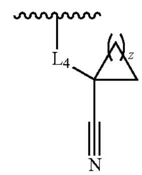

(i-36)

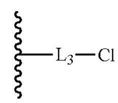

(i-37)

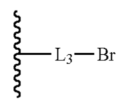

(i-38)

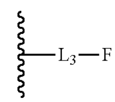

(i-39)

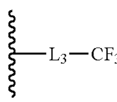

(i-40)

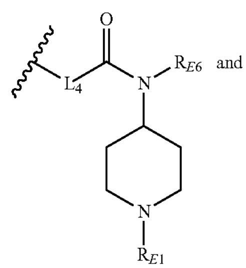

and (i-41)

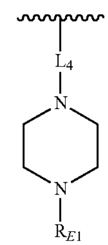

;

$L_3$ is a bond, —NH—, or $C_1$-$C_4$ alkylene, optionally wherein one or more carbon is independently replaced with —C(O)—, —O—, —S—, —$NR_{L3a}$—, —$NR_{L3a}$C(O)—, —C(O)$NR_{L3a}$—, —SC(O)—, —C(O)S—, OC(O)—, —C(O)O—, —$NR_{L3a}$C(S)—, —C(S)$NR_{L3a}$—, trans-$CR_{L3b}$=$CR_{L3b}$—, cis-$CR_{L3b}$=$CR_{L3b}$, C≡C, —S(O)—, —S(O)O—, —OS(O)—, —S(O)$NR_{L3a}$—, —$NR_{L3a}$S(O)—, —$S(O)_2$—, —$S(O)_2O$—, —$OS(O)_2$—, —S(O))$_2NR_{L3a}$—, or —$NR_{L3a}S(O)_2$—;

$R_{L3a}$ is hydrogen, $C_1$-$C_6$ alkyl optionally substituted with $R^9$, or a nitrogen protecting group;

$R_{L3b}$ is independently, at each occurrence, selected from the group consisting of hydrogen, halogen, $C_1$-$C_6$ alkyl, $C_2$-$C_6$ alkenyl, $C_2$-$C_6$ alkynyl, 3-8 membered cycloalkyl, 3-12 membered heterocycloalkyl, 6-10 membered aryl, and 5-8 membered heteroaryl, wherein alkyl, alkenyl, alkynyl, cycloalkyl, heterocyclyl, aryl, and heteroaryl are optionally substituted with one, two, or three $R^9$;

or, alternatively, two $R_{L3b}$ groups, together with the atoms to which they are attached, form a 3-8 membered cycloalkyl or 4-7 membered heterocycloalkyl, both of which are optionally substituted with one, two, or three $R^9$;

$L_4$ is a bond or $C_1$-$C_6$ alkyl optionally substituted with one, two, or three $R^9$;

each of $R_{E1}$, $R_{E2}$, and $R_{E3}$ is independently selected from the group consisting of hydrogen, halogen, $C_1$-$C_6$ alkyl, $C_2$-$C_6$ alkenyl, $C_2$-$C_6$ alkynyl, 3-12 membered cycloalkyl, 3-12 membered heterocycloalkyl, 6-12 membered aryl, and 5-12 membered heteroaryl, ON, $CH_2OR_{EE}$, $CH_2N(R_{EE})_2$, $CH_2SR_{EE}$, $OR_{EE}$, $N(R_{EE})_2$, $SR_{EE}$, wherein alkyl, alkenyl, alkynyl, cycloalkyl, heterocyclyl, aryl, and heteroaryl are optionally substituted with one, two, or three $R^9$;

or, alternatively, $R_{E1}$ and $R_{E3}$, or $R_{E2}$ and $R_{63}$, or $R_{E1}$ and $R_{E2}$ are joined to form 3-8 membered cycloalkyl or 4-7 membered heterocycloalkyl, both of which are optionally substituted with one, two, or three $R^9$;

each $R_{EE}$ is independently selected from the group consisting of hydrogen, $C_1$-$C_6$ alkyl, $C_1$-$C_6$ alkoxy, $C_2$-$C_6$ alkenyl, $C_2$-$C_6$ alkynyl, 3-8 membered cycloalkyl, 3-8 membered heterocycloalkyl, 6-10 membered aryl, and 5-10 membered heteroaryl, wherein alkyl, alkenyl, alkynyl, cycloalkyl, heterocyclyl, aryl, and heteroaryl are optionally substituted with one, two, or three $R^9$;

or, alternatively, two $R_{EE}$ groups, together with the atom to which they are attached, form 4-7 membered heterocycloalkyl;

$R_{E5}$ is halogen;

$R_{E6}$ is hydrogen, $C_1$-$C_6$ alkyl, or a nitrogen protecting group;

each Y is independently O, S, or $NR_{E7}$;

$R_{E7}$ is hydrogen, $C_1$-$C_6$ alkyl, or a nitrogen protecting group;

m is 0 or 1;

n is 0, 1, 2, or 3; and p is 0, 1, 2, 3, or 4.

In an embodiment, $R^2$ is (i-1)

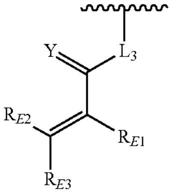

.

In another embodiment, $R^2$ is (i-1)

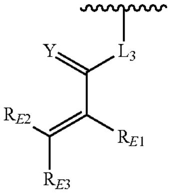

;

wherein L3 is —NH— and Y is O.

In yet another embodiment, the compound of Formula is a compound of Formula II:

(II)

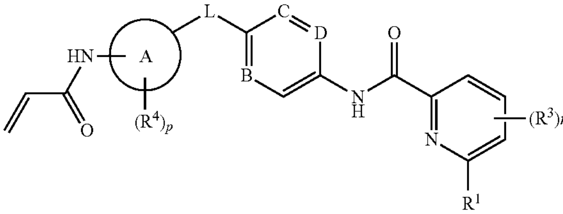

or a pharmaceutically acceptable salt thereof.

In still another embodiment, the compound of Formula I is a compound of Formula III:

(III)

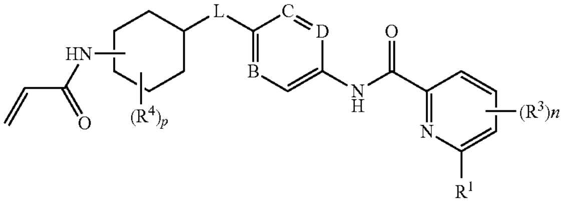

or a pharmaceutically acceptable salt thereof.

In an embodiment, the compound of Formula I is a compound of Formula IV:

(IV)

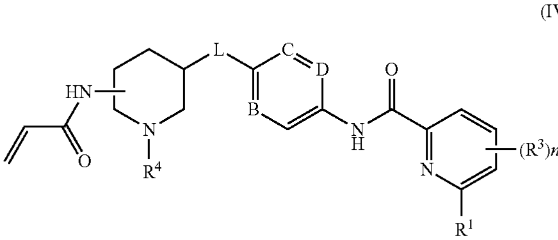

or a pharmaceutically acceptable salt thereof.

In another embodiment, the compound of Formula I is a compound of Formula IVa:

(IVa)

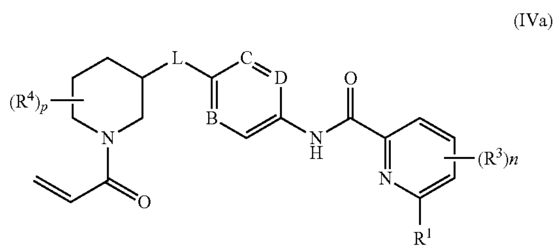

or a pharmaceutically acceptable salt thereof.

In yet another embodiment, the compound of Formula I is a compound of Formula V:

(V)

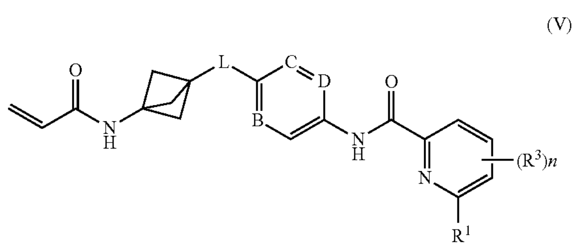

or a pharmaceutically acceptable salt thereof.

In still another embodiment, the compound of Formula I is a compound of Formula VI:

(VI)

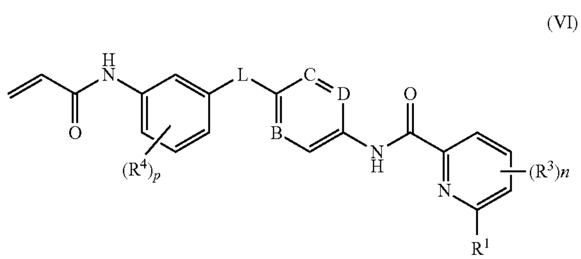

or a pharmaceutically acceptable salt thereof.

In an embodiment, the compound of Formula I is a compound of Formula VII:

(VII)

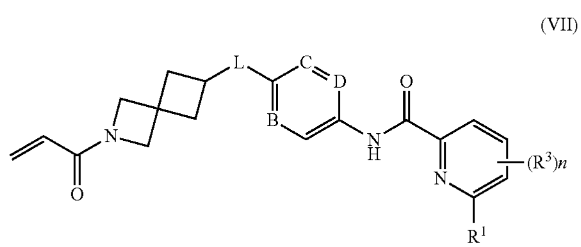

or a pharmaceutically acceptable salt thereof.

In an embodiment, $R^1$ is selected from the group consisting of pyrazole, isoxazole, pyrrole, furan, thiophene, imidazole, oxazole, thiazole, isothiazole, pyridine, indole, and benzofuran. In another embodiment, $R^1$ is pyrazole or isoxazole.

In another embodiment, L is selected from the group consisting of

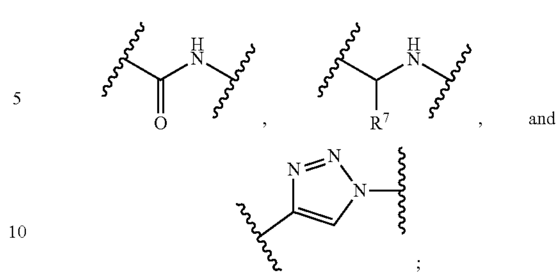

wherein $R^7$ is $C_1$-$C_6$ alkyl optionally substituted with one, two, or three halogen.

In yet another embodiment, B is CH, C is CH, and D is N. In still another embodiment, B is $CR^5$, C is CH, and D is CH. In an embodiment, B is N, C is CH, and D is N. In another embodiment, B is $CR^6$, C is CH, and D is N.

In yet another embodiment, n is 0. In still another embodiment, p is 0 or 1.

In an embodiment, the compound of Formula I, II, or II is selected from the group consisting of

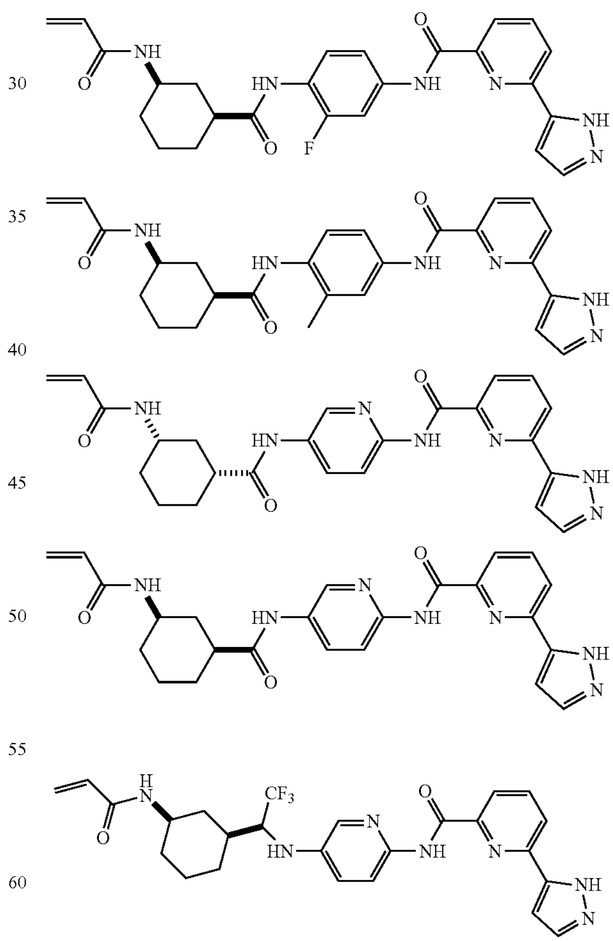

or a pharmaceutically acceptable salt thereof.

In another embodiment, the compound of Formula I. II, IV, or IVa is selected from the group consisting of -continued

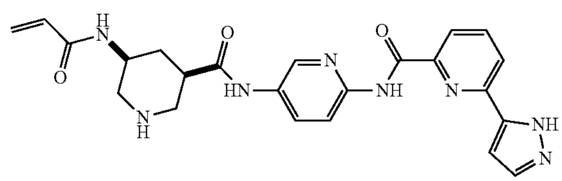

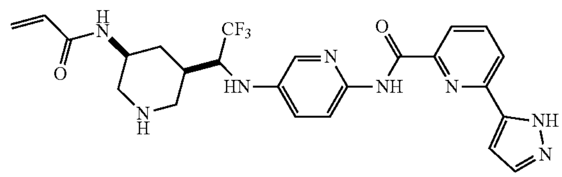

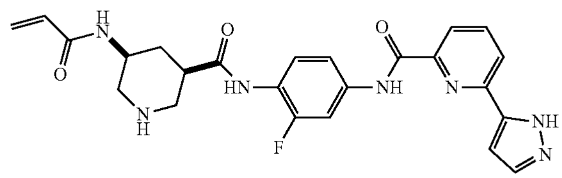

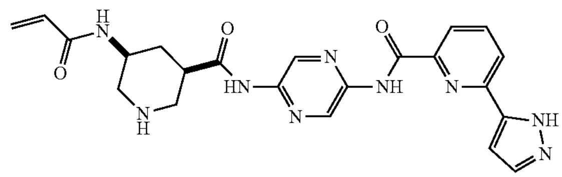

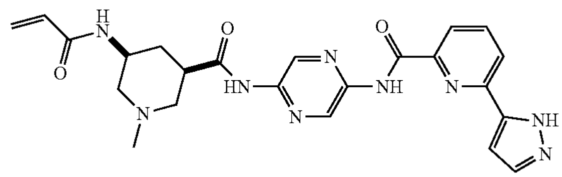

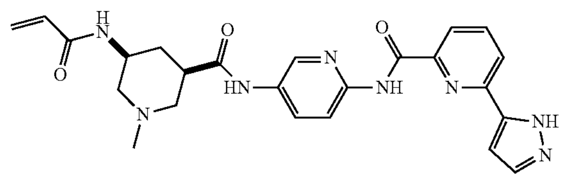

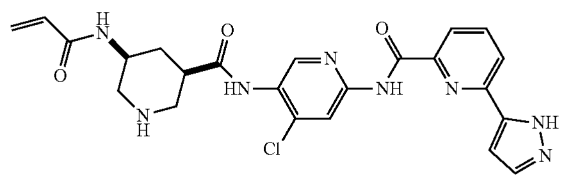

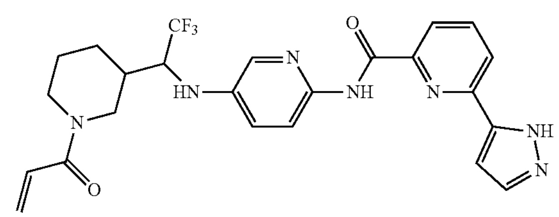

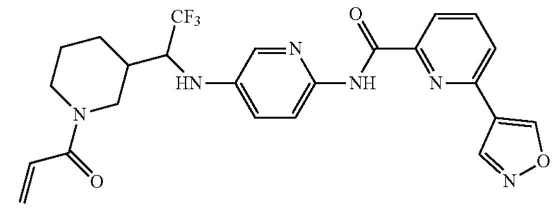

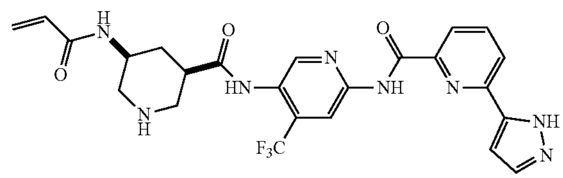

or a pharmaceutically acceptable salt thereof.

In yet another embodiment, the compound of Formula I, II, or V is selected from the group consisting of

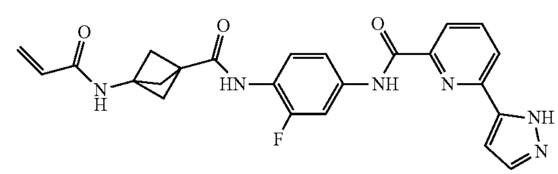

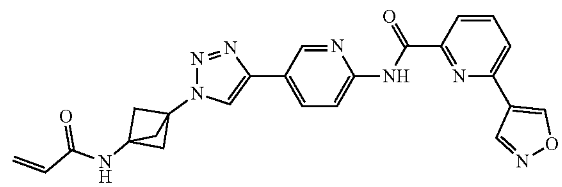

or a pharmaceutically acceptable salt thereof.

In still another embodiment, the compound of Formula I, II, or VI is selected from the group consisting of

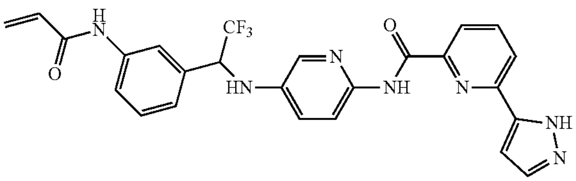

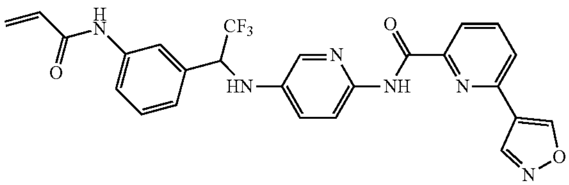

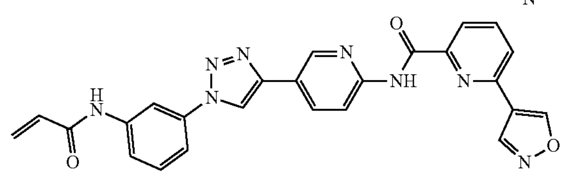

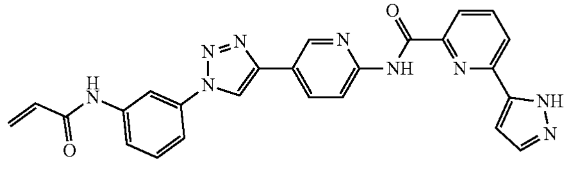

or a pharmaceutically acceptable salt thereof.

In an embodiment, the compound of Formula I, II, or VII is selected from the group consisting of:

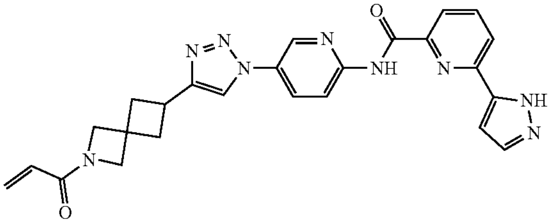
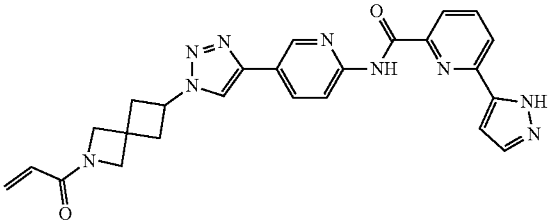
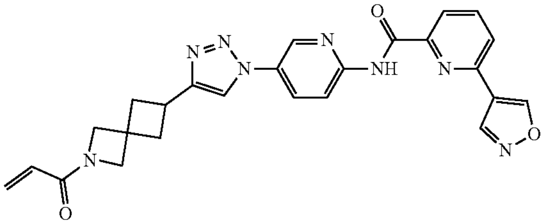
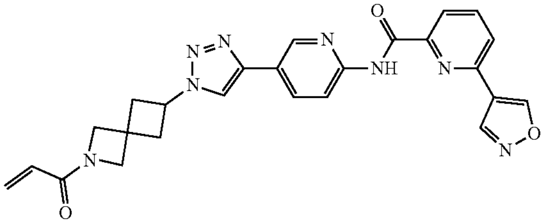
or a pharmaceutically acceptable salt thereof.
In another aspect, provided herein is a compound of Formula VIII:
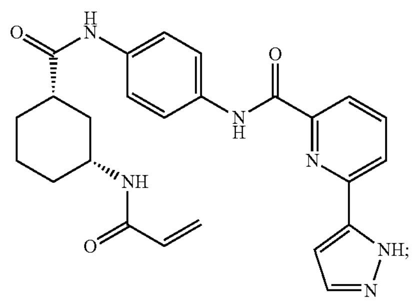 [SMILES: C=CC(=O)N[C@@H]1CCC[C@H](C(=O)Nc2ccc(NC(=O)c3cccc(-c4ccn[nH]4)n3)cc2)C1]
or a pharmaceutical y acceptable salt thereof.
In yet another embodiment, the compound of Formula I is selected from the group consisting of
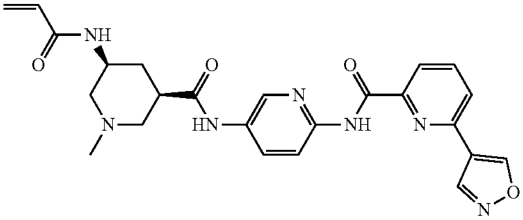
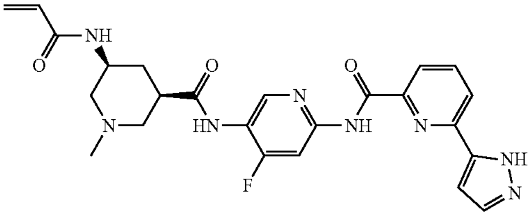
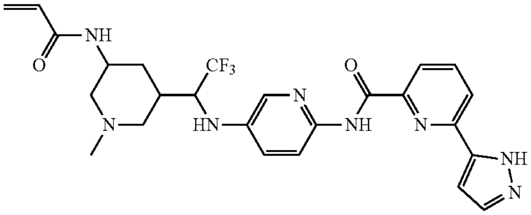
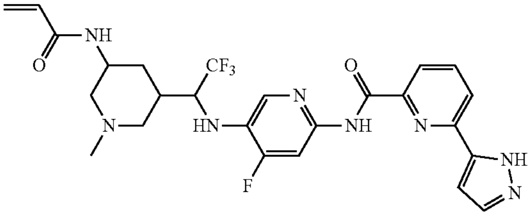
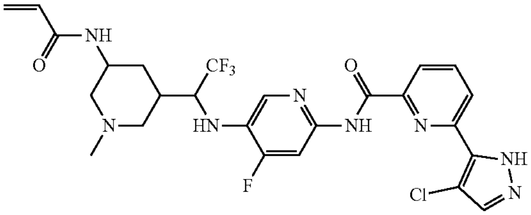
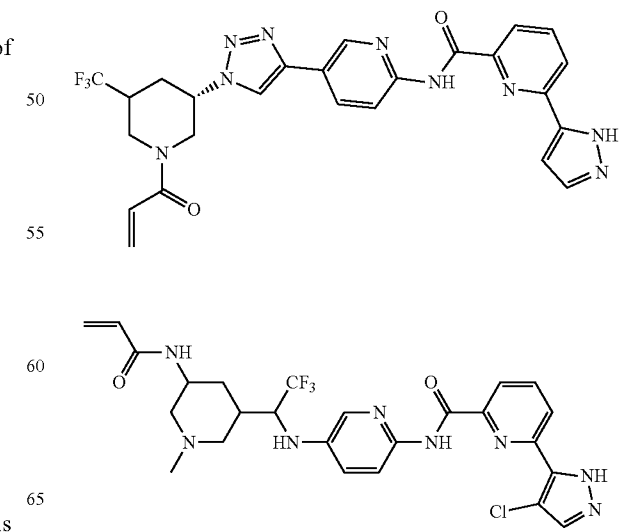

-continued
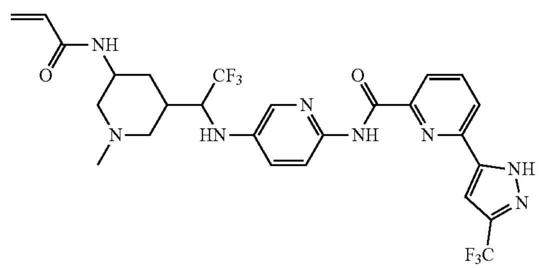
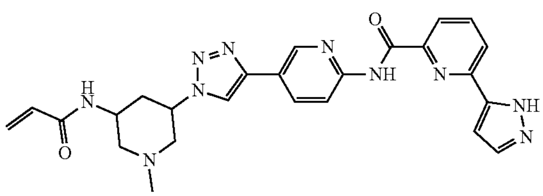
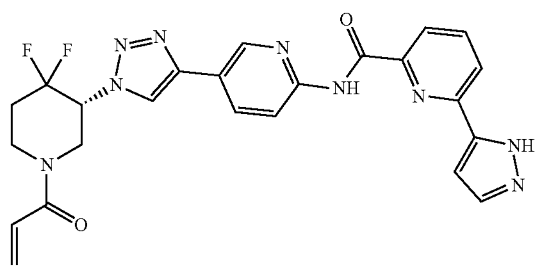
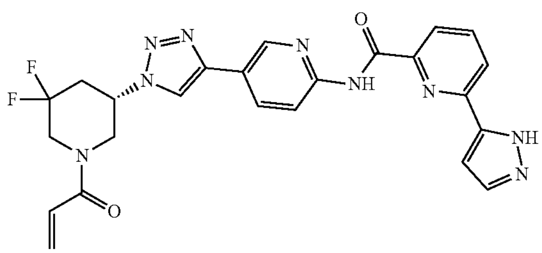
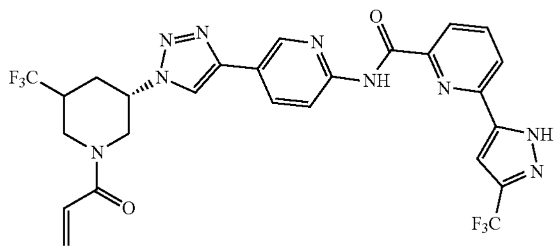
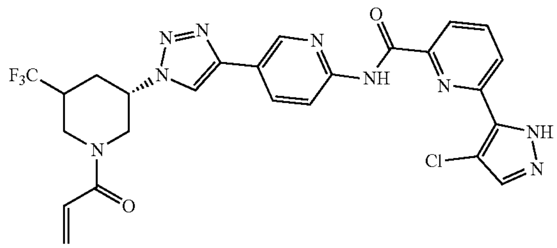
-continued
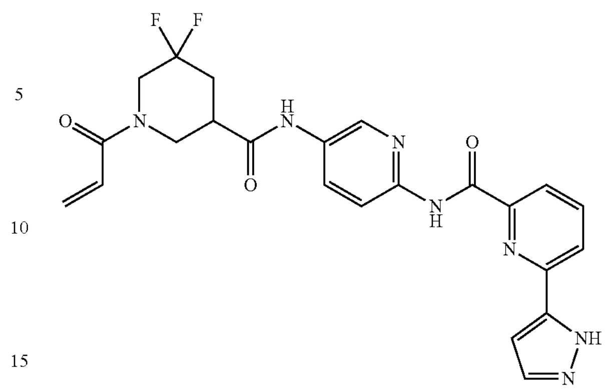
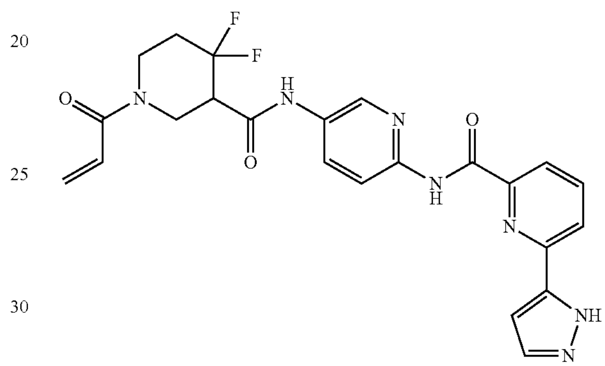
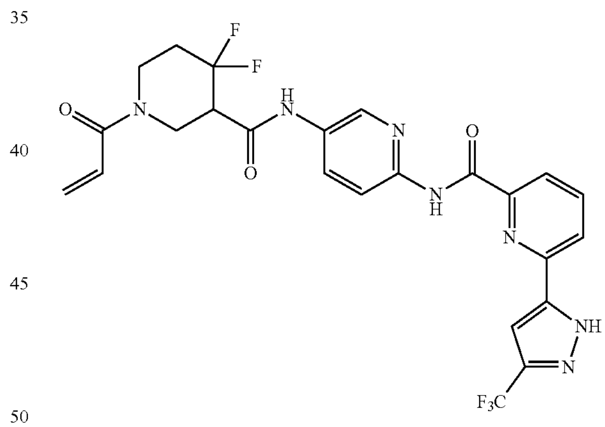
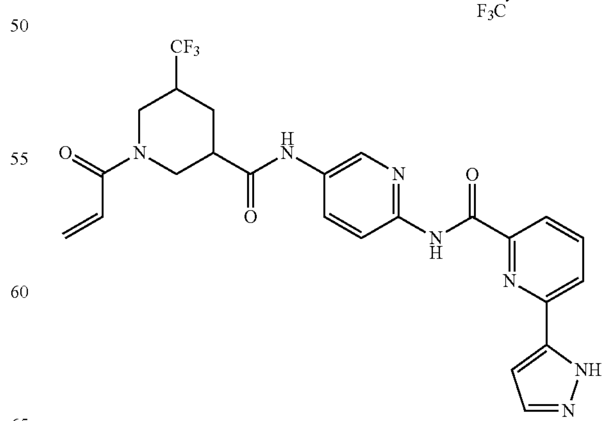

-continued
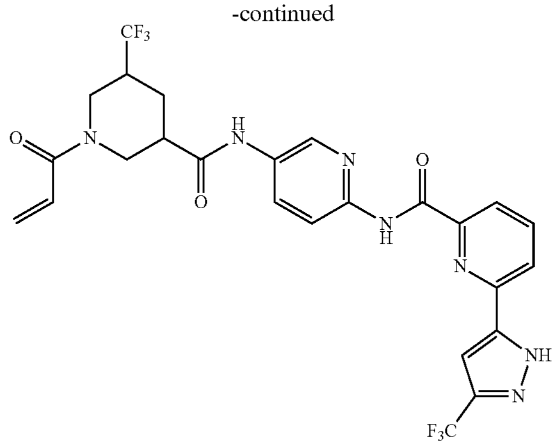
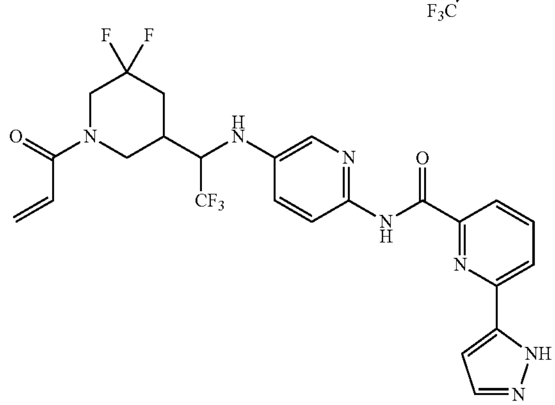
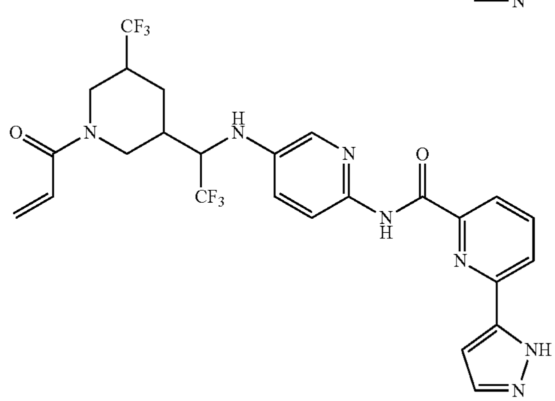
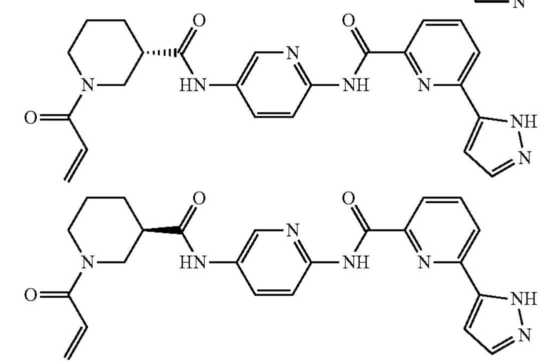
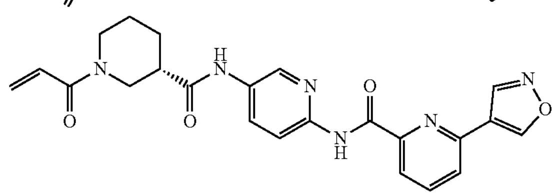
-continued
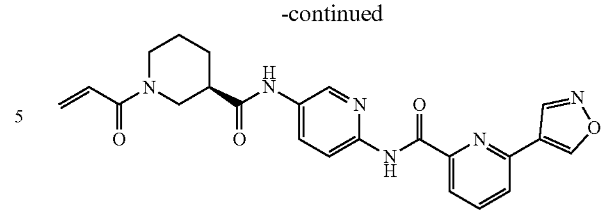
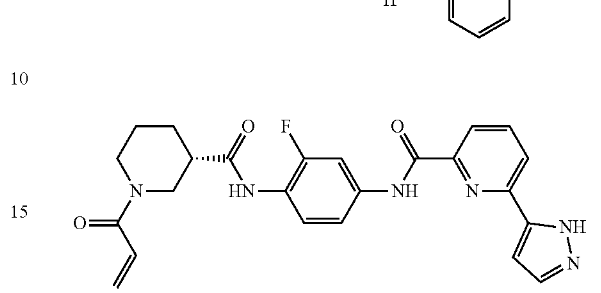
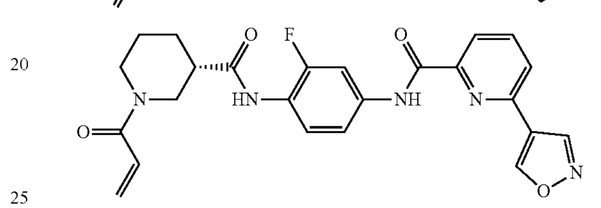
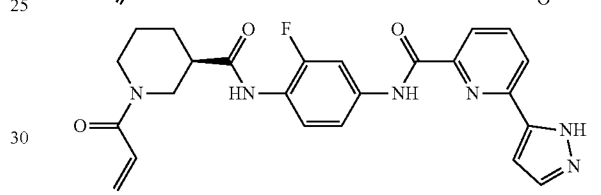
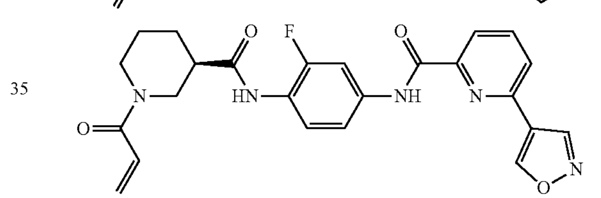
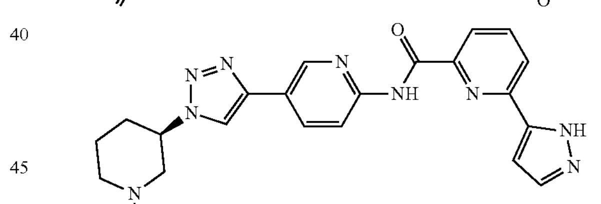
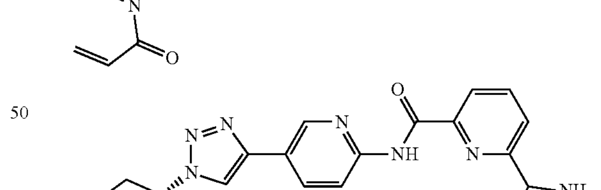
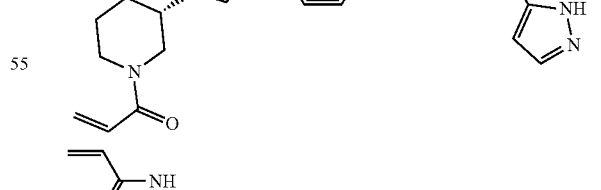
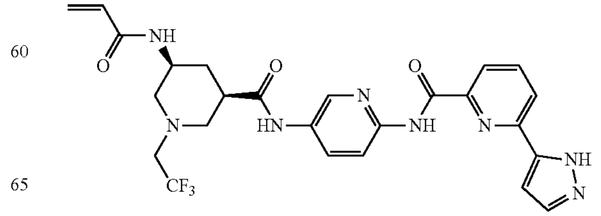

-continued
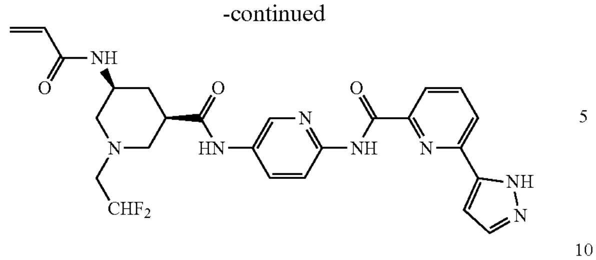
or a pharmaceutically acceptable salt thereof.
In another embodiment the compound of Formula i is selected from the group consisting of a compound in Table 1.
TABLE 1
| Structure | Compound No. |
|---|---|
| 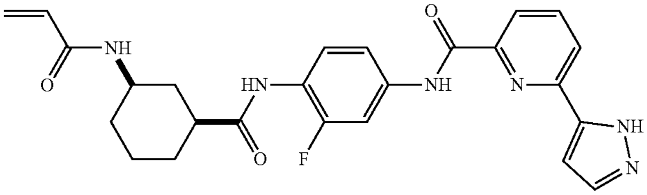 | 001 |
| 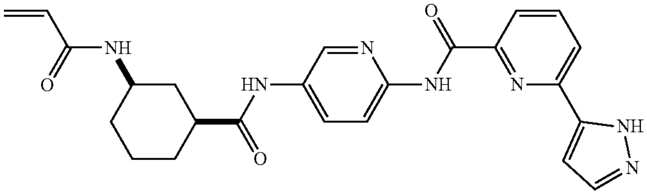 | 002 |
| 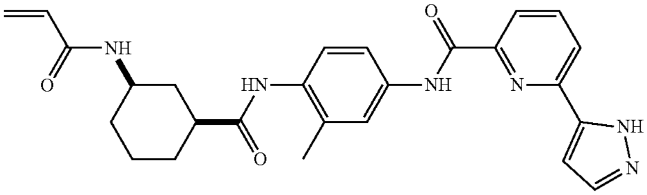 | 003 |
| 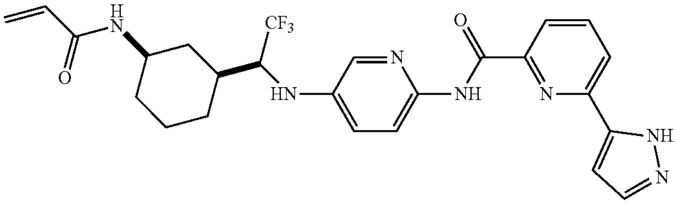 [SMILES: C=CC(=O)N[C@@H]1CCCC([C@H](Nc2ccc(NC(=O)c3cccc(-c4ccn[nH]4)n3)nc2)C(F)(F)F)C1] | 004 |
| 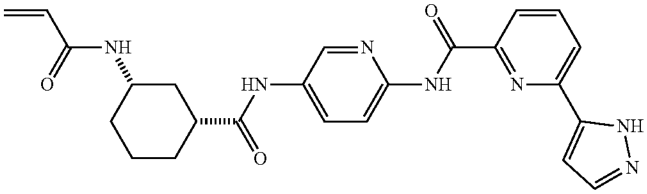 | 005 |

TABLE 1-continued
| Structure | Compound No. |
| --- | --- |
| 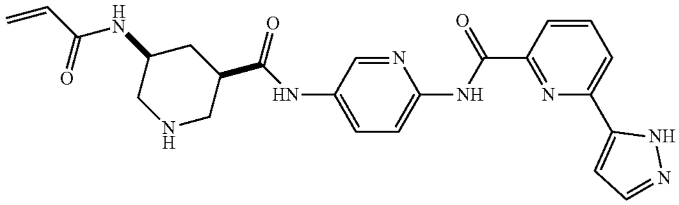 | 006 |
| 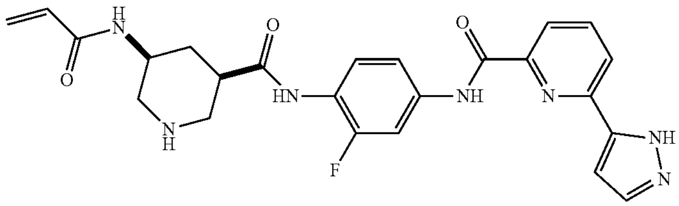 | 007 |
| 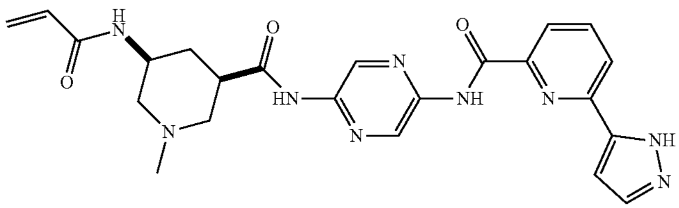 | 008 |
| 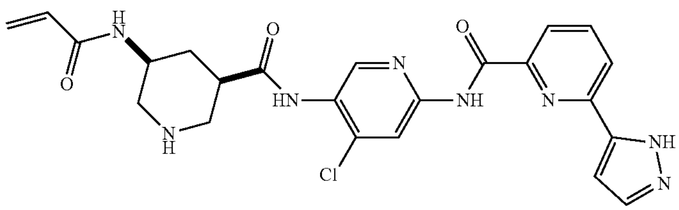 | 009 |
| 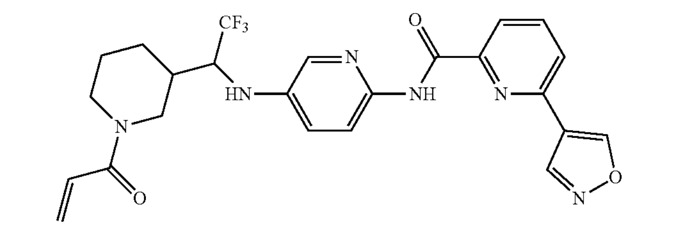 [SMILES: C=CC(=O)N1CCCC(C(Nc2ccc(NC(=O)c3cccc(-c4cnoc4)n3)nc2)C(F)(F)F)C1] | 010 |
| 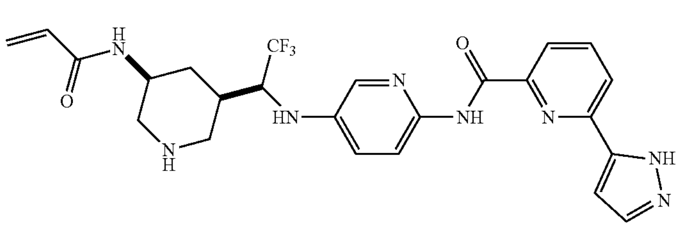 [SMILES: C=CC(=O)N[C@@H]1CNCC([C@H](Nc2ccc(NC(=O)c3cccc(-c4ccn[nH]4)n3)nc2)C(F)(F)F)C1] | 011 |
| 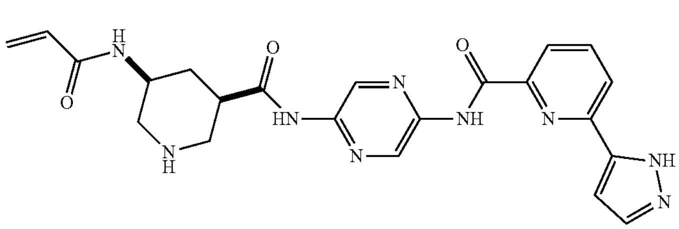 | 012 |

TABLE 1-continued
| Structure | Compound No. |
| --- | --- |
| 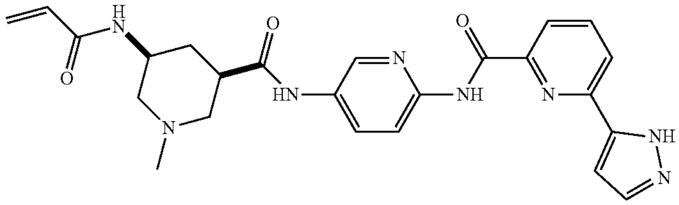 | 013 |
| 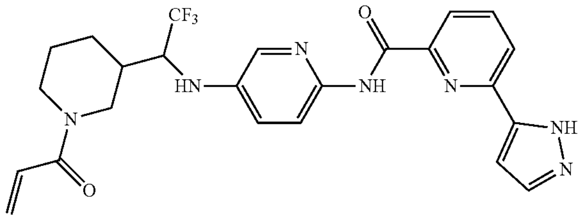 [SMILES: C=CC(=O)N1CCCC(C(Nc2ccc(NC(=O)c3cccc(-c4ccn[nH]4)n3)nc2)C(F)(F)F)C1] | 014 |
| 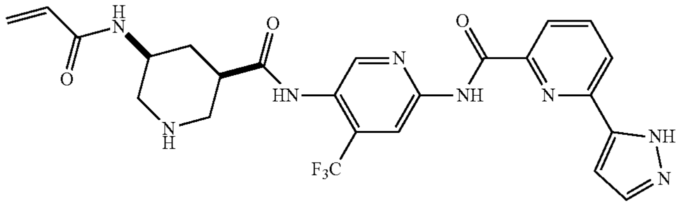 | 015 |
| 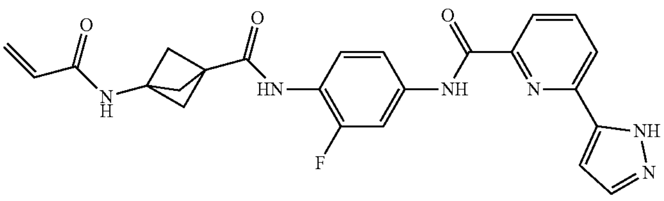 [SMILES: C=CC(=O)NC12CC(C(=O)Nc3ccc(NC(=O)c4cccc(-c5ccn[nH]5)n4)cc3F)(C1)C2] | 016 |
| 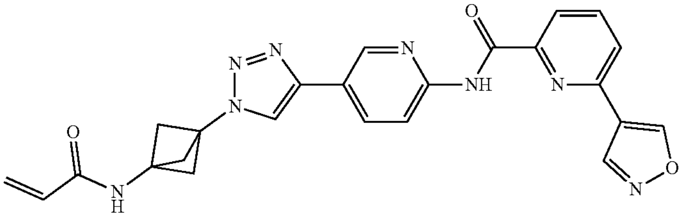 [SMILES: C=CC(=O)NC12CC(n3cc(-c4ccc(NC(=O)c5cccc(-c6cnoc6)n5)nc4)nn3)(C1)C2] | 017 |
| 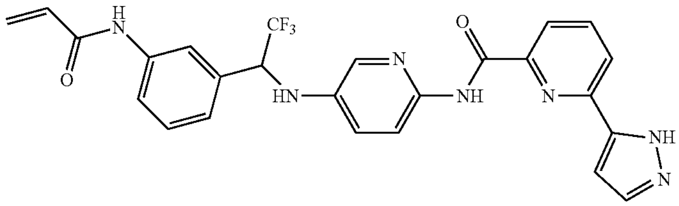 [SMILES: C=CC(=O)Nc1cccc(C(Nc2ccc(NC(=O)c3cccc(-c4ccn[nH]4)n3)nc2)C(F)(F)F)c1] | 018 |
| 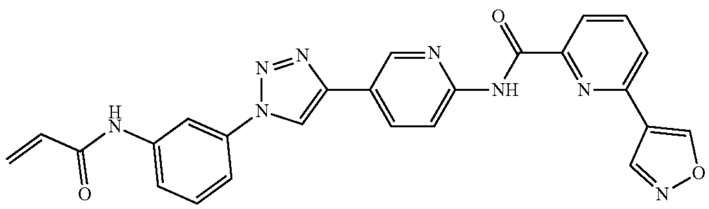 [SMILES: C=CC(=O)Nc1cccc(-n2cc(-c3ccc(NC(=O)c4cccc(-c5cnoc5)n4)nc3)nn2)c1] | 019 |

TABLE 1-continued
| Structure | Compound No. |
|---|---|
| 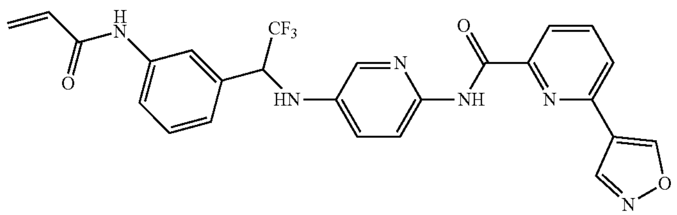 [SMILES: C=CC(=O)Nc1cccc(C(Nc2ccc(NC(=O)c3cccc(-c4cnoc4)n3)nc2)C(F)(F)F)c1] | 020 |
| 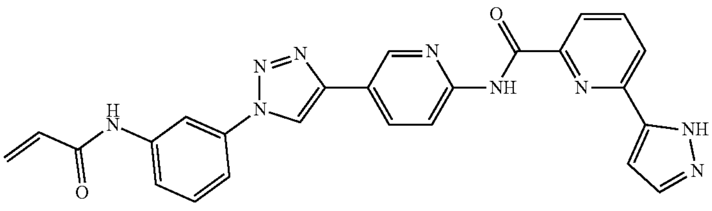 [SMILES: C=CC(=O)Nc1cccc(-n2cc(-c3ccc(NC(=O)c4cccc(-c5ccn[nH]5)n4)nc3)nn2)c1] | 021 |
| 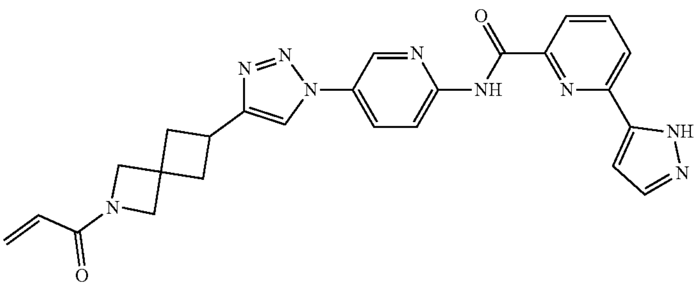 [SMILES: C=CC(=O)N1CC2(CC(c3cn(-c4ccc(NC(=O)c5cccc(-c6ccn[nH]6)n5)nc4)nn3)C2)C1] | 022 |
| 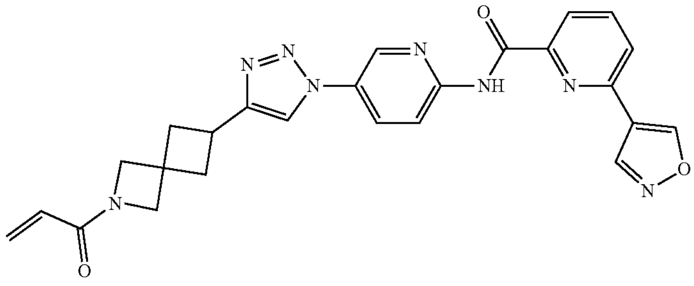 [SMILES: C=CC(=O)N1CC2(CC(c3cn(-c4ccc(NC(=O)c5cccc(-c6cnoc6)n5)nc4)nn3)C2)C1] | 023 |
| 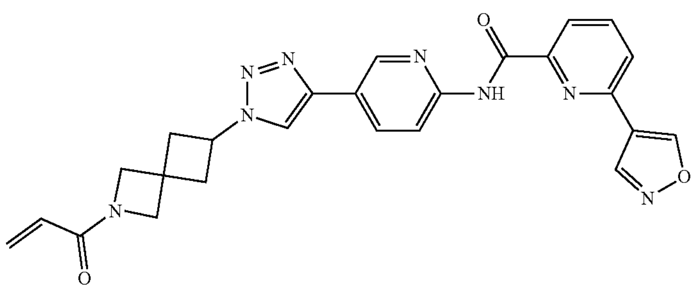 [SMILES: C=CC(=O)N1CC2(CC(n3cc(-c4ccc(NC(=O)c5cccc(-c6cnoc6)n5)nc4)nn3)C2)C1] | 024 |
| 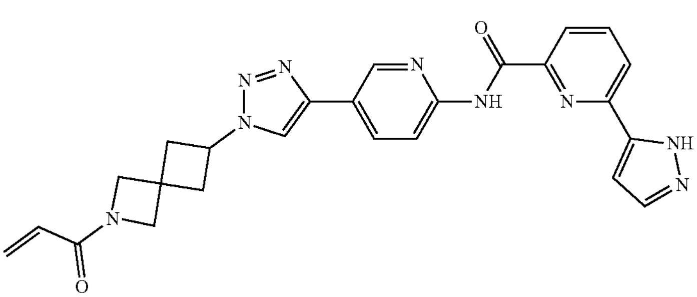 [SMILES: C=CC(=O)N1CC2(CC(n3cc(-c4ccc(NC(=O)c5cccc(-c6ccn[nH]6)n5)nc4)nn3)C2)C1] | 025 |

TABLE 1-continued
| Structure | Compound No. |
|---|---|
| 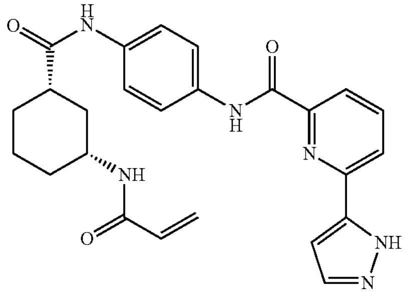 [SMILES: C=CC(=O)N[C@@H]1CCC[C@H](C(=O)Nc2ccc(NC(=O)c3cccc(-c4ccn[nH]4)n3)cc2)C1] | 026 |
| 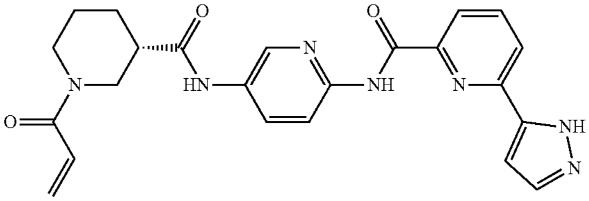 [SMILES: C=CC(=O)N1CCC[C@H](C(=O)Nc2ccc(NC(=O)c3cccc(-c4ccn[nH]4)n3)nc2)C1] | 027 |
| 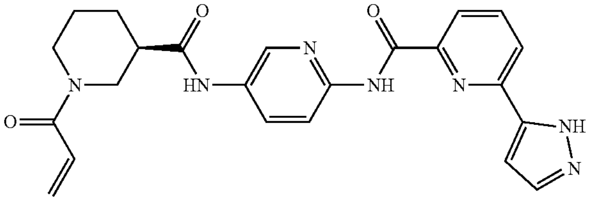 [SMILES: C=CC(=O)N1CCC[C@@H](C(=O)Nc2ccc(NC(=O)c3cccc(-c4ccn[nH]4)n3)nc2)C1] | 028 |
| 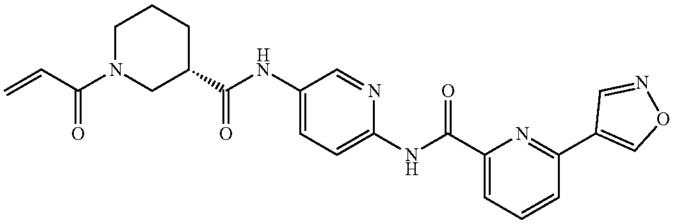 [SMILES: C=CC(=O)N1CCC[C@H](C(=O)Nc2ccc(NC(=O)c3cccc(-c4cnoc4)n3)nc2)C1] | 029 |
| 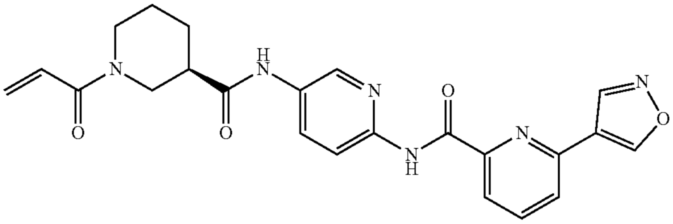 [SMILES: C=CC(=O)N1CCC[C@@H](C(=O)Nc2ccc(NC(=O)c3cccc(-c4cnoc4)n3)nc2)C1] | 030 |
| 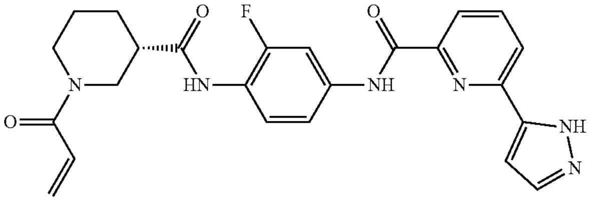 [SMILES: C=CC(=O)N1CCC[C@H](C(=O)Nc2ccc(NC(=O)c3cccc(-c4ccn[nH]4)n3)cc2F)C1] | 031 |

TABLE 1-continued
| Structure | Compound No. |
| --- | --- |
| 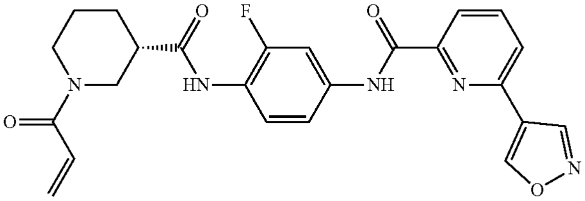 [SMILES: C=CC(=O)N1CCC[C@H](C(=O)Nc2ccc(NC(=O)c3cccc(-c4cnoc4)n3)cc2F)C1] | 032 |
| 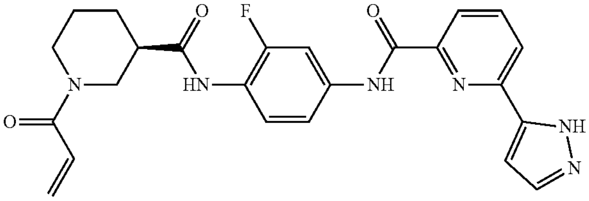 [SMILES: C=CC(=O)N1CCC[C@@H](C(=O)Nc2ccc(NC(=O)c3cccc(-c4ccn[nH]4)n3)cc2F)C1] | 033 |
| 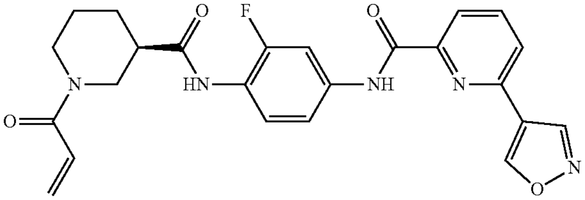 [SMILES: C=CC(=O)N1CCC[C@@H](C(=O)Nc2ccc(NC(=O)c3cccc(-c4cnoc4)n3)cc2F)C1] | 034 |
| 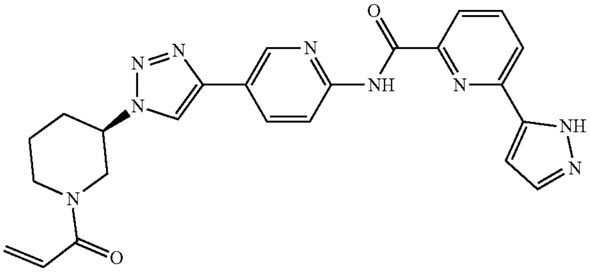 [SMILES: C=CC(=O)N1CCC[C@@H](n2cc(-c3ccc(NC(=O)c4cccc(-c5ccn[nH]5)n4)nc3)nn2)C1] | 035 |
| 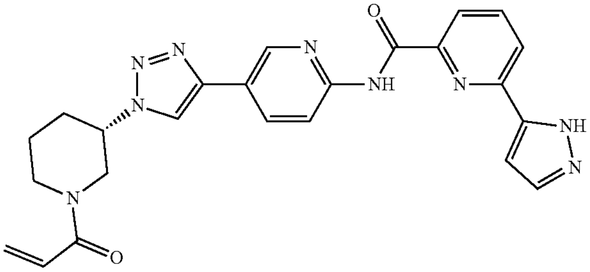 [SMILES: C=CC(=O)N1CCC[C@H](n2cc(-c3ccc(NC(=O)c4cccc(-c5ccn[nH]5)n4)nc3)nn2)C1] | 036 |
| 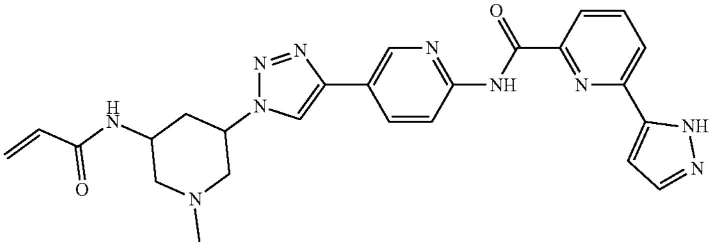 [SMILES: C=CC(=O)NC1CC(n2cc(-c3ccc(NC(=O)c4cccc(-c5ccn[nH]5)n4)nc3)nn2)CN(C)C1] | 037 |

TABLE 1-continued
| Structure | Compound No. |
| --- | --- |
| 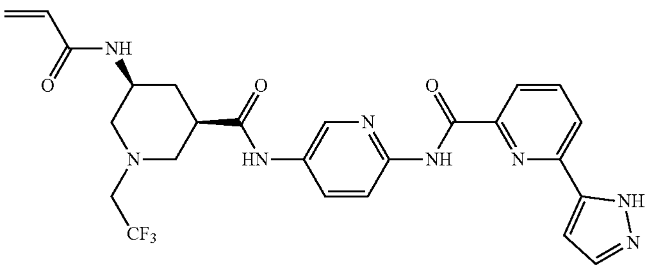 [SMILES: C=CC(=O)N[C@H]1C[C@@H](C(=O)Nc2ccc(NC(=O)c3cccc(-c4ccn[nH]4)n3)nc2)CN(CC(F)(F)F)C1] | 038 |
| 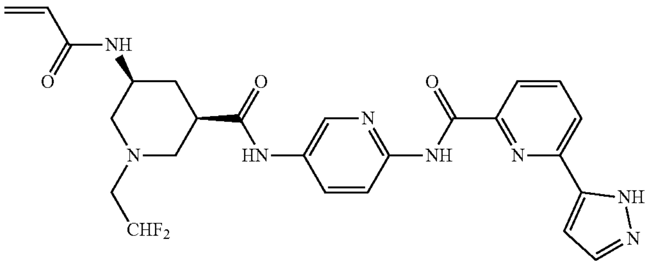 [SMILES: C=CC(=O)N[C@H]1C[C@@H](C(=O)Nc2ccc(NC(=O)c3cccc(-c4ccn[nH]4)n3)nc2)CN(CC(F)F)C1] | 039 |
| 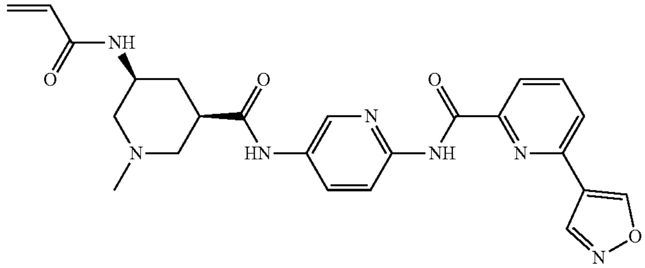 [SMILES: C=CC(=O)N[C@H]1C[C@@H](C(=O)Nc2ccc(NC(=O)c3cccc(-c4cnoc4)n3)nc2)CN(C)C1] | 040 |
| 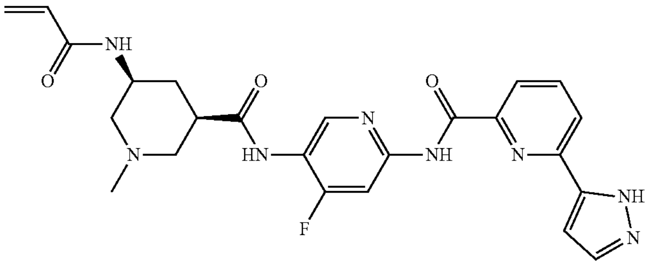 [SMILES: C=CC(=O)N[C@H]1C[C@@H](C(=O)Nc2cnc(NC(=O)c3cccc(-c4ccn[nH]4)n3)cc2F)CN(C)C1] | 041 |
| 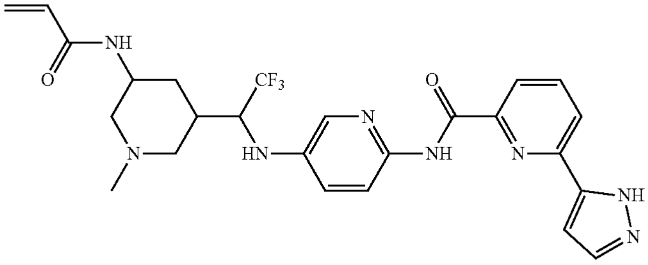 [SMILES: C=CC(=O)NC1CC(C(Nc2ccc(NC(=O)c3cccc(-c4ccn[nH]4)n3)nc2)C(F)(F)F)CN(C)C1] | 042 |

TABLE 1-continued
| Structure | Compound No. |
| --- | --- |
| 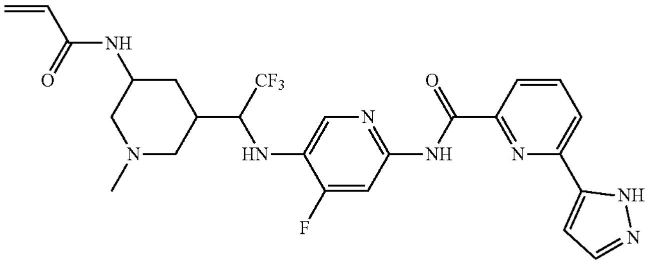 [SMILES: C=CC(=O)NC1CC(C(Nc2cnc(NC(=O)c3cccc(-c4ccn[nH]4)n3)cc2F)C(F)(F)F)CN(C)C1] | 043 |
| 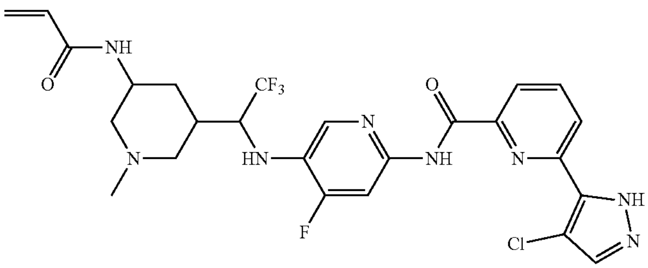 [SMILES: C=CC(=O)NC1CC(C(Nc2cnc(NC(=O)c3cccc(-c4[nH]ncc4Cl)n3)cc2F)C(F)(F)F)CN(C)C1] | 044 |
| 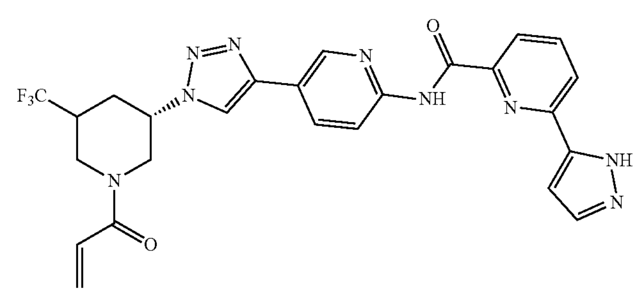 [SMILES: C=CC(=O)N1CC(C(F)(F)F)C[C@H](n2cc(-c3ccc(NC(=O)c4cccc(-c5ccn[nH]5)n4)nc3)nn2)C1] | 045 |
| 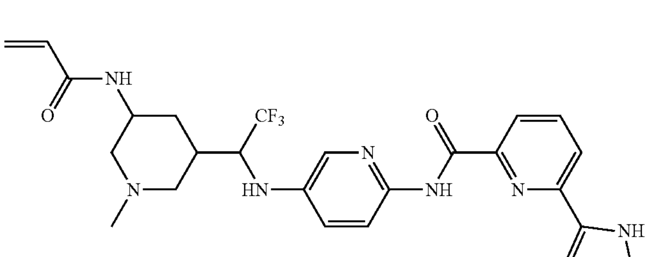 | 046 |
| 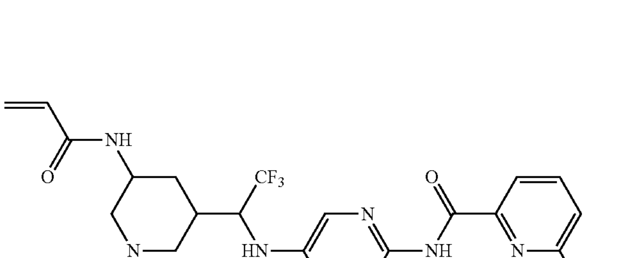 | 047 |

TABLE 1-continued
| Structure | Compound No. |
| --- | --- |
| 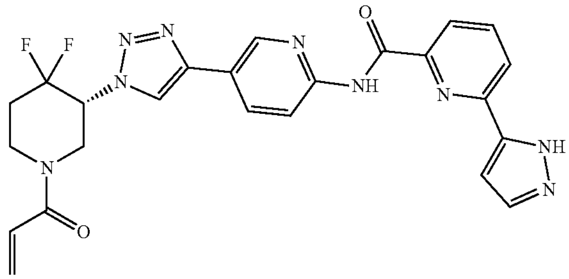 [SMILES: C=CC(=O)N1CCC(F)(F)[C@H](n2cc(-c3ccc(NC(=O)c4cccc(-c5ccn[nH]5)n4)nc3)nn2)C1] | 048 |
| 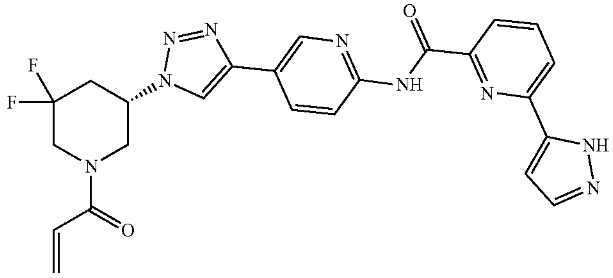 [SMILES: C=CC(=O)N1C[C@@H](n2cc(-c3ccc(NC(=O)c4cccc(-c5ccn[nH]5)n4)nc3)nn2)CC(F)(F)C1] | 049 |
| 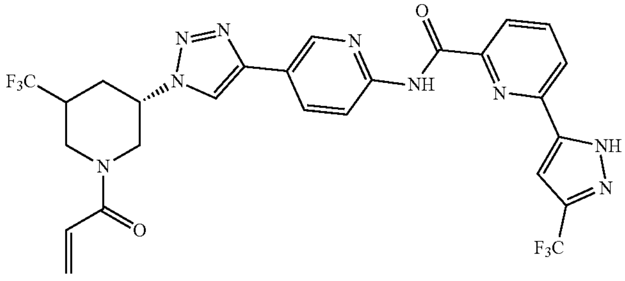 [SMILES: C=CC(=O)N1CC(C(F)(F)F)C[C@H](n2cc(-c3ccc(NC(=O)c4cccc(-c5cc(C(F)(F)F)n[nH]5)n4)nc3)nn2)C1] | 050 |
| 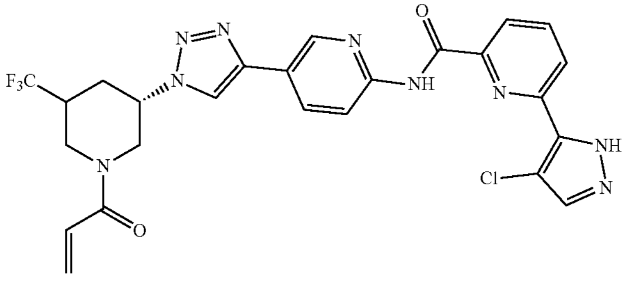 [SMILES: C=CC(=O)N1CC(C(F)(F)F)C[C@H](n2cc(-c3ccc(NC(=O)c4cccc(-c5[nH]ncc5Cl)n4)nc3)nn2)C1] | 051 |
| 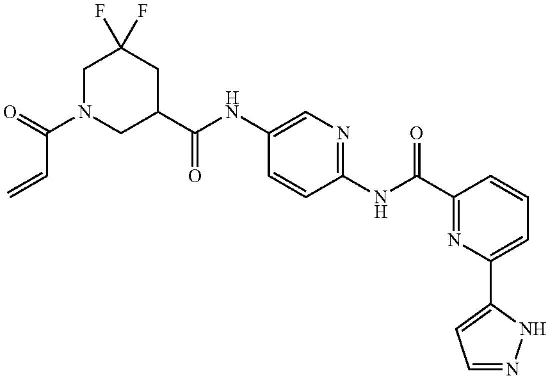 [SMILES: C=CC(=O)N1CC(C(=O)Nc2ccc(NC(=O)c3cccc(-c4ccn[nH]4)n3)nc2)CC(F)(F)C1] | 052 |

TABLE 1-continued
| Structure | Compound No. |
| --- | --- |
| 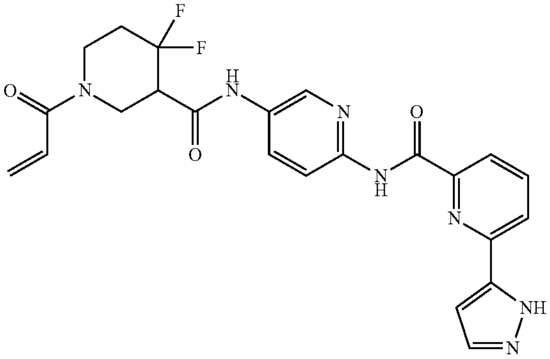 [SMILES: C=CC(=O)N1CCC(F)(F)C(C(=O)Nc2ccc(NC(=O)c3cccc(-c4ccn[nH]4)n3)nc2)C1] | 053 |
| 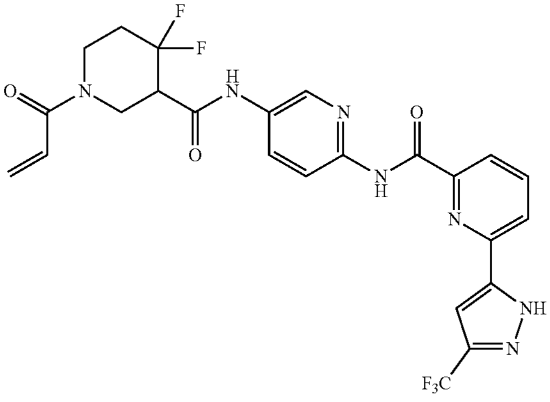 [SMILES: C=CC(=O)N1CCC(F)(F)C(C(=O)Nc2ccc(NC(=O)c3cccc(-c4cc(C(F)(F)F)n[nH]4)n3)nc2)C1] | 054 |
| 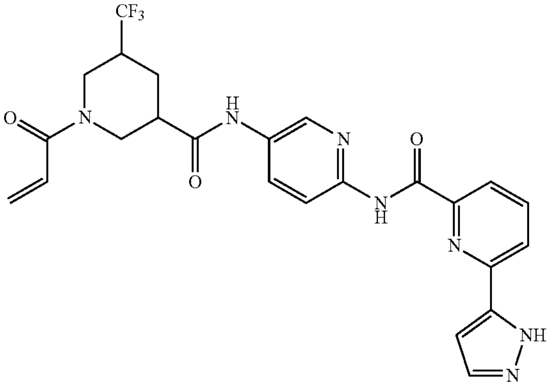 [SMILES: C=CC(=O)N1CC(C(=O)Nc2ccc(NC(=O)c3cccc(-c4ccn[nH]4)n3)nc2)CC(C(F)(F)F)C1] | 055 |
| 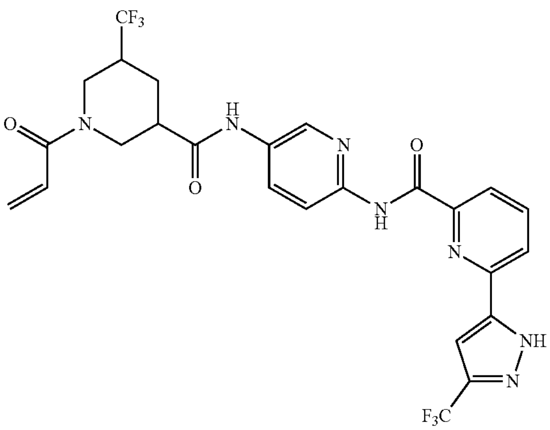 [SMILES: C=CC(=O)N1CC(C(=O)Nc2ccc(NC(=O)c3cccc(-c4cc(C(F)(F)F)n[nH]4)n3)nc2)CC(C(F)(F)F)C1] | 056 |

TABLE 1-continued

| Structure | Compound No. |
| --- | --- |
| 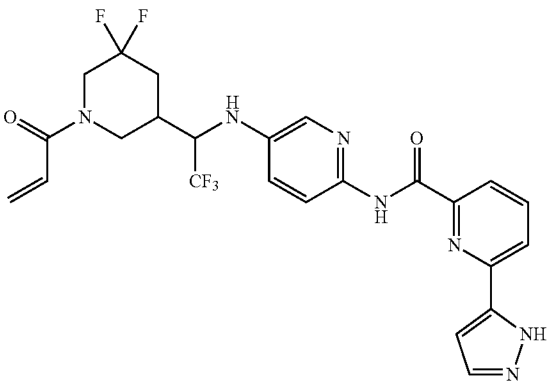 [SMILES: C=CC(=O)N1CC(C(Nc2ccc(NC(=O)c3cccc(-c4ccn[nH]4)n3)nc2)C(F)(F)F)CC(F)(F)C1] | 057 |
| 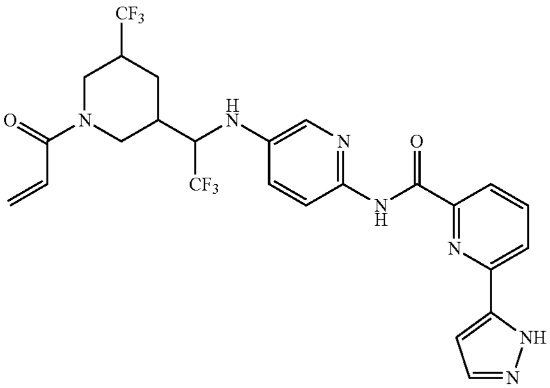 [SMILES: C=CC(=O)N1CC(C(Nc2ccc(NC(=O)c3cccc(-c4ccn[nH]4)n3)nc2)C(F)(F)F)CC(C(F)(F)F)C1] | 058 |

or a pharmaceutically acceptable salt thereof.

In an aspect, provided herein is a compound of any of the Formulae disclosed herein, or a pharmaceutically acceptable salt thereof, and a pharmaceutically acceptable carrier.

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound of Formulae I-VII is a prodrug within the scope of the present disclosure.

In another aspect, the pharmaceutical composition further comprises a second active agent, wherein said second pharmaceutical agent. In some embodiments, the second pharmaceutical agent is a kinase inhibitor. In further embodiments, the second pharmaceutical agent is a Bruton's tyrosine kinase (BTK) inhibitor.

In yet another aspect, the present disclosure provides pharmaceutical compositions including a compound described herein, and optionally a pharmaceutically acceptable excipient.

In an embodiment, the pharmaceutical compositions described herein include a therapeutically or prophylactically effective amount of a compound described herein. The pharmaceutical composition may be useful for treating a proliferative disease in a subject in need thereof, preventing a proliferative disease in a subject in need thereof, or inhibiting the activity of a protein kinase (e.g., IRAK) in a subject, biological sample, tissue, or cell. In certain embodiments, the proliferative disease is cancer (e.g., lymphoma, leukemia, or myelodysplastic syndrome (MDS)). In certain embodiments, the proliferative disease is an inflammatory disease. In certain embodiments, the inflammatory disease is rheumatoid arthritis, Crohn s disease, or fibrosis. In certain embodiments, the proliferative disease is an autoimmune disease.

Methods of Treatment

In an aspect, provided herein is a method of treating cancer in an individual in need thereof, comprising administering to the individual a therapeutically effective amount of a compound of Formula I. In an embodiment, the cancer is selected from the group consisting of lung cancer, colon cancer, breast cancer, endometrial cancer, thyroid cancer, glioma, squamous cell carcinoma, and prostate cancer. In another embodiment, the cancer is non-small cell lung cancer (NSCLC).

In another aspect, provided herein is a method of inhibiting a kinase in an individual in need thereof, comprising administering to the individual a therapeutically effective amount of a compound of Formula I. In an embodiment, the kinase is IRAK. In another embodiment, the kinase is IRAK1. In yet another embodiment, the kinase is IRAK4.

In another aspect, the present disclosure provides methods for eating and/or preventing a proliferative disease. Exemplary proliferative diseases that may be treated include diseases associated with the overexpression or increased activity of an interleukin-1 receptor-associated kinase (IRAK), e.g., cancer, benign neoplasms, diseases associated with angiogenesis, inflammatory diseases, autoinflammatory diseases, and autoimmune diseases. In certain embodiments, the cancer is selected from the group consisting of pancreatic cancer, lung cancer (e.g., small cell lung cancer (SCLC), non-small cell lung cancer), prostate cancer, breast cancer, ovarian cancer, kidney cancer, liver cancer, Ewing's sarcoma, myeloma, Waldenström s macroglobulinemia, myelodysplastic syndrome (MDS), osteosarcoma, brain cancer, neuroblastoma, and colorectal cancer.

In another aspect, provided herein is a method of inhibiting the activity of a kinase (e.g., IRAK (e.g., IRAK1 or IRAK4)) using a compound described herein in a biological sample or subject. In certain embodiments, the method involves the selective inhibition of IRAK1. In certain embodiments, the method involves the selective inhibition of IRAK4.

The present disclosure also provides methods of inhibiting cell growth in a biological sample or subject. In still another aspect, the present invention provides methods of inducing apoptosis of a cell in a biological sample or subject.

The present disclosure provides methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent (e.g., an antiproliferative agent). In certain embodiments, the additional pharmaceutical agent is a kinase inhibitor (e.g., an inhibitor of Bruton's tyrosine kinase (BTK)). The methods described herein may further include performing radiotherapy, immunotherapy, and/or transplantation on the subject.

In yet another aspect, provided herein is a method of treating or preventing a kinase-mediated disorder in an individual in need thereof, comprising administering to the individual a therapeutically effective amount of a compound of Formula I.

Modulation of IRAK containing provides an approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit greater inhibition of IRAK1 relative to IRAK4. In certain embodiments, the compounds of the disclosure exhibit at least 2-fold, 3-fold, 5-fold, 10-fold; 25-fold, 50-fold or 100-fold greater inhibition of IRAK1 to IRAK4. In various embodiments, the compounds of the disclosure exhibit up to 1000-fold greater inhibition of IRAK1 relative IRAK4. In various embodiments, the compounds of the disclosure exhibit up to 10000-fold greater inhibition of IRAK1 relative to IRAK4.

In some embodiments, the inhibition of IRAK activity is measured by $IC_{50}$.

In some embodiments, the inhibition of IRAK activity is measured by $EC_{50}$.

In some embodiments, the inhibition of IRAK by a compound of the disclosure can be measured via a biochemical assay. By illustrative and non-limiting example, a homogenous time-resolved fluorescence (HTRF) assay may be used to determine inhibition of IRAK activity using conditions and experimental parameters disclosed herein. The HTRF assay may, for example, employ concentrations of substrate (e.g., biotin-Lck-peptide substrate) of about 1 μM; concentrations of IRAK from about 0.2 nM to about 40 nM; and concentrations of inhibitor from about 0.000282 μM to about 50 μM. A compound of the disclosure screened under these conditions may, for example, exhibit an $IC_{50}$ value from about 1 nM to >1 μM; from about 1 nM to about 400 nM; from about 1 nil to about 150 nM; from about 1 nM to about 75 nM; from about 1 nM to about 40 nM; from about 1 nM to about 25 nM; from about 1 nM to about 15 nM; or from about 1 nM to about 10 nM.

In some embodiments, the compounds of the disclosure bind irreversibly to IRAK.

Potency of the inhibitor can be determined by $EC_{50}$ value. A compound with a lower $EC_{50}$ value, as determined under substantially similar conditions, is a more potent inhibitor relative to a compound with a higher $EC_{50}$ value.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value.

The selectivity between IRAK1 and IRAK4 can also be measured using cellular proliferation assays where cell proliferation is dependent on kinase activity. Proliferation assays are performed at a range of inhibitor concentrations (10 μM, 3 μM; 1.1 μM, 330 nM, 110 nM, 33 nM, 11 nM, 3 nM, 1 nM) and an $EC_{50}$ is calculated.

In still another aspect, the disclosure provides a method IRAK, the method comprising administering to a subject in need thereof an effective amount of a compound of disclosed herein, or a pharmaceutically acceptable salt thereof. In some embodiments, the method further comprises administering a second pharmaceutical agent. In some embodiments, the second pharmaceutical agent is an antibody. In another embodiment, the second pharmaceutical agent is a kinase inhibitor. In yet another embodiment, the second pharmaceutical agent is a Bruton's tyrosine kinase (BTK) inhibitor.

The additional pharmaceutical agents include, but are not limited to, antiproliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent).

In certain embodiments, the additional pharmaceutical agent is ibrutinib. In certain embodiments, the additional pharmaceutical agent is a protein kinase inhibitor (e.g., tyrosine protein kinase inhibitor). In certain embodiments, the additional pharmaceutical agent is a binder or inhibitor of an IRAK (e.g., IRAK1 or IRAK4). In certain embodiments, the additional pharmaceutical agent is a binder or inhibitor of IRAK1. In certain embodiments, the additional pharmaceutical agent is a binder or inhibitor of IRAK4. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g. tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In yet another aspect, provided herein is a method of treating a kinase-mediated disorder comprising administering to a subject in need thereof an effective amount of a compound disclosed herein, or a pharmaceutically acceptable salt thereof. In some embodiments, the kinase is IRAK. In other embodiments, the subject is administered an additional therapeutic agent. In other embodiments, the compound and the additional therapeutic agent are administered simultaneously or sequentially.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In an embodiment of the methods disclosed herein, the subject is a human.

In another aspect, the disclosure provides a compound disclosed herein, or a pharmaceutically acceptable salt thereof, for use in the manufacture of a medicament for treating or preventing a disease in which IRAK plays a role.

In an aspect, provided herein is a method of treating or preventing a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

In certain embodiments, the proliferative disease to be treated or prevented using the compounds described herein may be associated with the overexpression of an IRAK (e.g., IRAK1 or IRAK4).

A proliferative disease may be associated with aberrant activity of an IRAK (e.g., IRAK1 or IRAK4). Aberrant activity of an IRAK (e.g., IRAK1 or IRAK4) may be elevated and/or inappropriate or undesired activity of the IRAK. Deregulation of cell cycle progression is a characteristic of a proliferative disease, and a majority of proliferative diseases have abnormalities in some component of IRAK (e.g., IRAK1 or IRAK4) activity, frequently through elevated and/or inappropriate IRAK activation. In certain embodiments, IRAK is not overexpressed, and the activity of IRAK is elevated and/or inappropriate. In certain embodiments, IRAK1 is overexpressed, and the activity of IRAK1 is elevated and/or inappropriate. In certain embodiments, IRAK4 is overexpressed, and the activity of IRAK4 is elevated and/or inappropriate.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colonrectum, large intestine, rectum, brain and central nervous system, chronic myeloid leukemia (CML), and leukemia. The term "cancer" includes, but is not limited to, the following cancers: myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

The term "cancerous cell" as provided herein, includes a cell afflicted by any one of the above-identified conditions.

The disclosure further provides a method for the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias, or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, adrenoleukodystrophy (ALD), Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, familial fatal insomnia, frontotemporal lobar degeneration, Huntington's disease, H1V-associated dementia, Kennedy's disease, Krabbe's disease, Lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease (also known as Batten disease), spinocerebellar ataxia (multiple types with varying characteristics), spinal muscular atrophy, Steele-Richardson-Olszewski disease, tabes dorsalis, and toxic encephalopathy.

Another aspect of this disclosure provides a method for the treatment or lessening the severity of a disease selected from a proliferative or hyperproliterative disease, or a neurodegenerative disease, comprising administering an effective amount of a compound, or a pharmaceutically acceptable composition comprising a compound, to a subject in need thereof.

The activity of the compounds and compositions of the present disclosure as IRAK inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt thereof, and optionally a second active agent. For any of the above uses, the required dosage will vary depending on the mode of administration, the particular condition to be treated and the effect desired.

Administration/Dosaaes/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

In certain embodiments, these compositions optionally further comprise one or more additional therapeutic agents. For example, a Bruton's tyrosine kinase (BTK) inhibitor, chemotherapeutic agents, or other antiproliferative agents may be combined with the compounds of this disclosure to treat proliferative diseases and cancer.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic add, or potassium sorbate; partial glyceride mixtures of saturated vegetable fatty adds; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting kinase activity selected from one or more compounds of disclosed herein, or pharmaceutically acceptable salts thereof, and instructions for use in treating cancer.

In another aspect, provided herein is a kit comprising a compound capable of inhibiting IRAK activity selected from a compound disclosed herein, or a pharmaceutically acceptable salt thereof.

In another aspect, the disclosure provides a kit comprising a compound capable of inhibiting kinase activity selected from one or more compounds of disclosed herein, or pharmaceutically acceptable salts thereof; a second active agent; and instructions for use in treating cancer. In some embodiments, the second active agent is a Bruton's tyrosine kinase (BTK) inhibitor. In an embodiment, the BTK inhibitor is ibrutinib. In another embodiment, the BTK inhibitor is acalabrutinib. In yet another embodiment, the BTK inhibitor is zanubrutinib.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations

ACN acetonitrile
DCM dichloromethane
DIEA diisopropylethylamine
DMF N,N-dimethylformamide
DMSO dimethylsulfoxide
dppf Bis(diphenylphosphino)ferrocene
EtOAc ethyl acetate
HATU 1-[Bis(dimethylamino)methylene]-1H-1,2,3-triazolo[4,5-b]pyridinium 3-oxide hexafluorophosphate
MeOH methanol
t-BuXPhos 2-di-tert-butylphosphino-2',4',6'-triisopropylbiphenyl
TFA trifluoroacetic acid
THF tetrahydrofuran

Example 1: Preparation of Compound 006

Scheme 1.

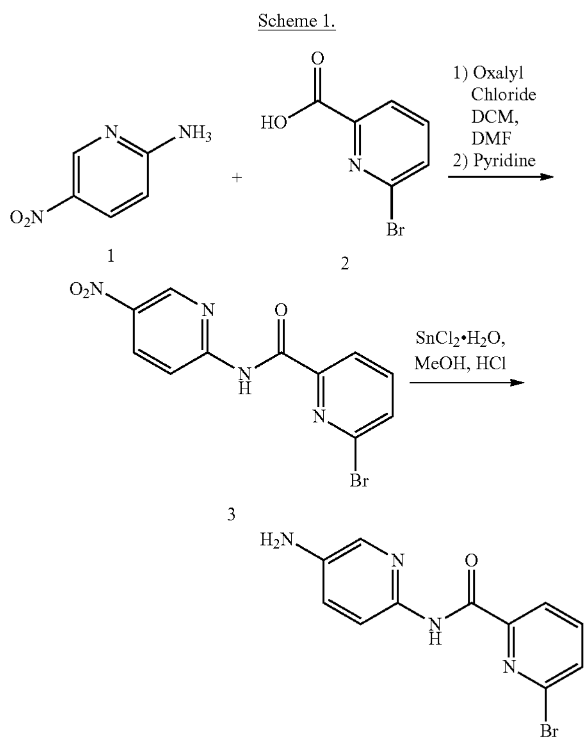

1 2

3

4

-continued

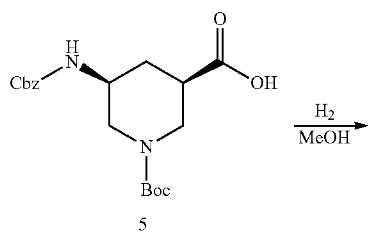

5

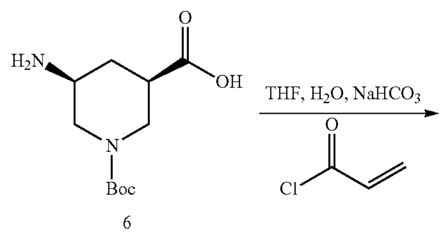

6

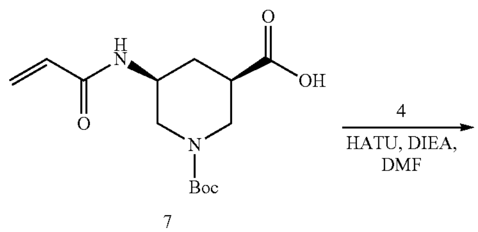

7

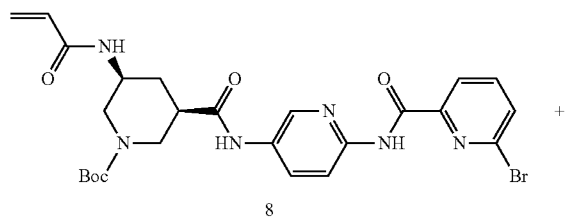

8

+

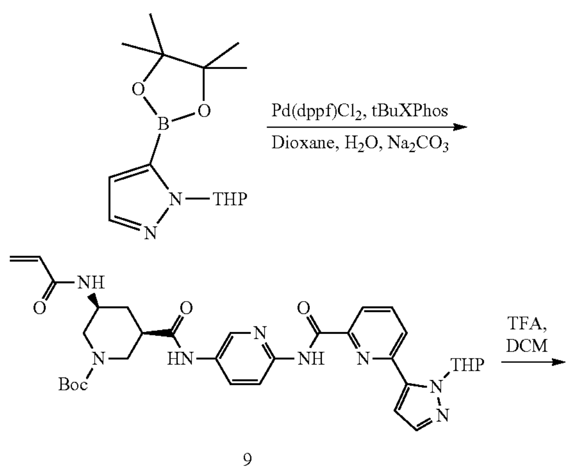

9

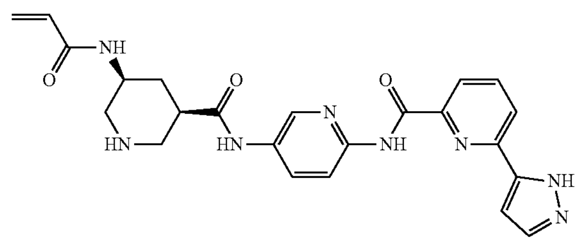

006

-continued

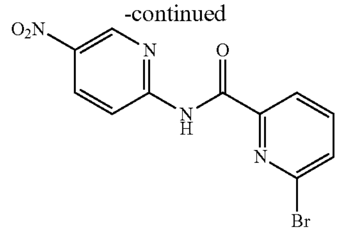

6-bromo-N-(5-nitropyridin-2-yl)picolinamide (3)

To a solution of 6-bromopicolinic acid (1 g, 4.95 mmol) in DCM (30 mL) was added oxalyl chloride (2.12 mL, 24.75 mmol) followed by DMF (5 drops). The mixture was stirred for 1 hour, then the solvent was removed. The residue was suspended in pyridine (10 mL) and a solution of 5-nitropyridin-2-amine (688 mg, 4.85 mmol) in pyridine (10 mL) was added dropwise at 0° C. After addition was complete, the mixture was warmed to a and stirred for 1 hour. The reaction was quenched with sat, aq. $NaHCO_3$ and extracted with DCM, dried over $MgSO_4$ and condensed. The resulting brown residue was triturated with EtOAc to yield a brown precipitate which was filtered, dried under $N_2$ and used in the next step without further purification. m/z ESI expected: 323.11, observed: 324.72

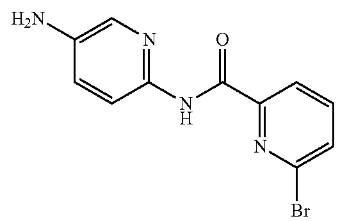 [SMILES: Nc1ccc(NC(=O)c2cccc(Br)n2)nc1]

N-(5-aminopyridin-2-yl)-6-bromopicolinamide (4)

To a solution of 3 (1.5 g, 4.64 mmol) in MeOH (30 mL) was added conc. HCl (5 mL) followed by $SnCl_2 \cdot 2H_2O$ (3.14 g, 1393 mmol). The mixture was stirred at 60° C. for 1 hour. The mixture was cooled to rt and diluted with EtOAc, $NH_4OH$ was added dropwise to adjust the pH to 6. Solid $Na_2CO_3$ was added to adjust pH to 10. The mixture was filtered and concentrated to yield the desired product as a brown solid that was used without further purification. m/z ESI expected: 293.12, observed: 294.64

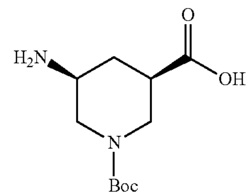 [SMILES: CC(C)(C)OC(=O)N1C[C@@H](N)C[C@@H](C(=O)O)C1]

(3R,5S)-5-amino-1-(tert-butoxycarbonyl)piperidine-3-carboxylic acid (6)

To a solution of (3R,5S)-5-(((benzyloxy)carbonyl) amino)-1-(tert-butoxycarbonyl)-piperidine-3-carboxylic acid (300 mg, 0.79 mmol) in MeOH (30 mL) was added 10% Pd/C (84 mg, 0.08 mmol). The flask was purged with $N_2$ and then a balloon filled with $H_2$ was attached. The mixture was stirred under $H_2$ for 2 hours, filtered through celite and condensed to give the desired compound as a clear oil that was used without further purification (190 mg, 97% yield). m/z ESI expected: 244.29, observed: 245.34

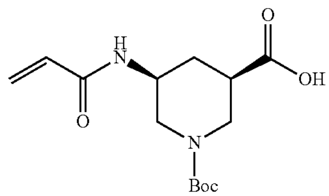 [SMILES: C=CC(=O)N[C@H]1C[C@@H](C(=O)O)CN(C(=O)OC(C)(C)C)C1]

(3R,5S)-5-acrylamido-1-(tert-butoxycarbonyl)piperidine-3-carboxylic acid (7)

To a solution of (3R,5S)-5-amino-1-(tert-butoxycarbonyl) piperidine-3-carboxylic acid (190 mg, 0.77 mmol) in THF (10 mL) was added sat. aq. $NaHCO_3$ (10 mL) followed by acryloyl chloride (75 μL, 0.92 mmol) was added and the mixture stirred for 15 minutes. The mixture was diluted with $H_2O$ and the pH adjusted to 5 using 10% HCl solution. The resulting solution was extracted with EtOAc, washed with brine, dried over $MgSO_4$ and condensed to give the desired product as a white solid that was used without further purification (210 mg, 91% yield). m/z ESI expected: 298, 34, observed: 298.79

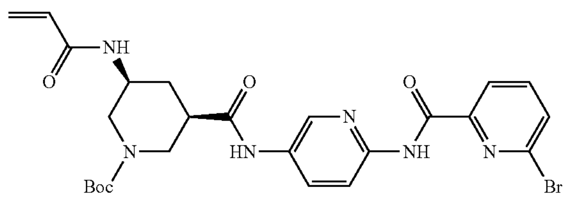 [SMILES: C=CC(=O)N[C@H]1C[C@@H](C(=O)Nc2ccc(NC(=O)c3cccc(Br)n3)nc2)CN(C(=O)OC(C)(C)C)C1]

tert-butyl (3S,5R)-3-acrylamido-54(6-(6-bromopicolinamido)pyridin-3-yl)carbamoyl)-piperidine-1-carboxylate (8)

To a solution of N-(5-aminopyridin-2-yl)-6-bromopicolinamide (200 mg, 0.68 mmol), HATU (519 mg, 1.36 mmol) and (3R,5S)-5-acrylamido-1-(tert-butoxycarbonyl) piperidine-3-carboxylic acid (203 mg, 0.68 mmol) in DMF (5 mL) was added DIEA (592 μL, 3.4 mmol). The mixture was stirred for 30 min at rt and then purified by reverse phase HPLC using a gradient of 1 to 80% ACN in $H_2O$ to give the desired compound as a white solid (280 mg, 72% yield) ink ESI expected: 573.45, observed: 574.52

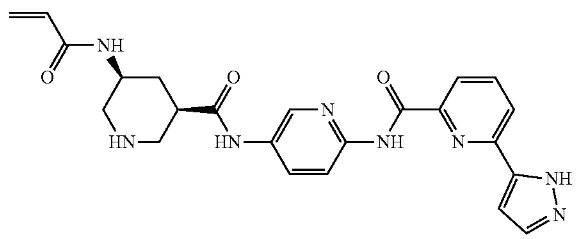 [SMILES: C=CC(=O)N[C@@H]1CNC[C@H](C(=O)Nc2ccc(NC(=O)c3cccc(-c4ccn[nH]4)n3)nc2)C1]

N-(5-((3R,5S)-5-acrylamidopiperidine-3-carboxamido)pyridin-2-yl)-6-(1H-pyrazol-5-yl)-picolinamide (006)

tert-butyl (3S,5R)-3-acrylamido-5-((6-(6-bromopicolinamido)pyridin-3-yl)carbamoyl)-piperidine-1-carboxylate (250 mg, 0.44 mmol) was dissolved in 1,4-Dioxane (5 mL). 1-(tetrahydro-2H-pyran-2-yl)-5-(4,4,5,5-tetramethyl-1,3,2-dioxaborolan-2-yl)-1H-pyrazole (146 mg, 0.52 mmol) was added followed by $Na_2CO_3$ 2M aqueous solution (1.1 mL, 2.19 mmol). The mixture was degassed in a sonicator for 2 minutes. Pd(dppf)$Cl_2$ (38 mg, 0.05 mmol) and t-BuXPhos (33 mg, 0.08 mmol) were added and the mixture heated to 90° C. in a sealed vial for 1 hour. The reaction was quenched with water (10 mL) and extracted with EtOAC (2×50 mL) washed with brine, dried over $MgSO_4$ and condensed. The crude material was dissolved in DCM (10 mL) and TFA (1 mL) was added. The mixture was stirred for 60 minutes and the solvent removed in vacuo. The crude material was purified by reversed phase HPLC to give the desired compound as a white solid (41 mg, 20% yield). m/z expected: 460.50, observed: 461.19; $^1$H NMR (500 MHz DMSO) δ 11.04 (Br, 1H), 10.45 (s, 1H), 9.07 (m, 1H), 8.90 (m, 1H), 8.69 (d, J=3 Hz, 1H), 8.35 (d, J=8 Hz, 1H), 8.28 (d, J=8 Hz, 1H), 8.15-8.06 (m, 3H) 7.75 (Br, 1H), 7.06 (d, J=2 Hz, 1H), 6.25-6.11 (m, 2H), 5.67 (dd, J=3 Hz, 10 Hz, 1H), 4.15 (m, 1H), 2.98, (m, 3H), 2.74 (m, 2H), 2.27 (m, 1H), 1.63 (m, 1H).

Example 2: Preparation of Compound 002

Scheme 2.

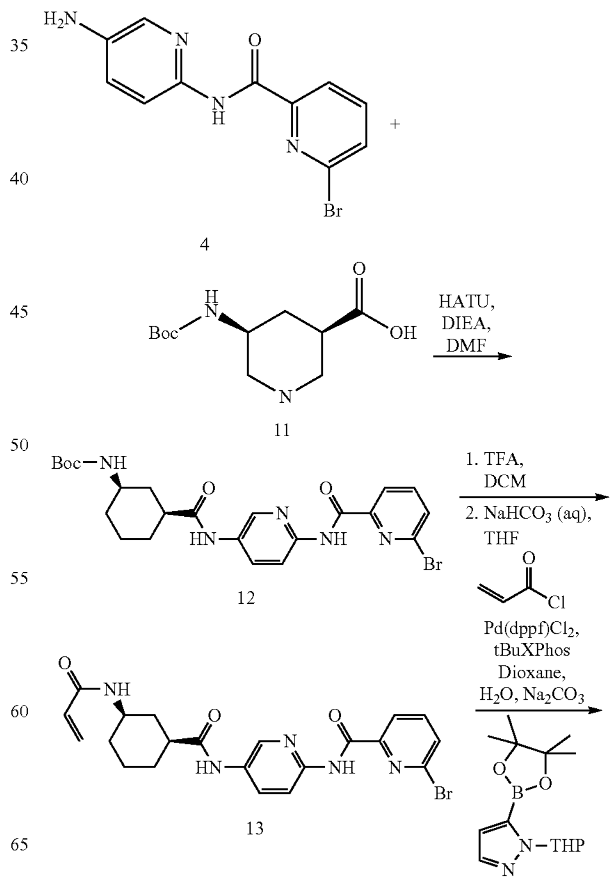

4

11

12

13

-continued

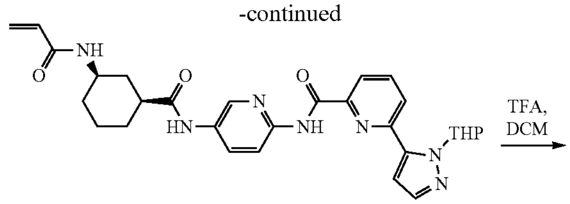

14

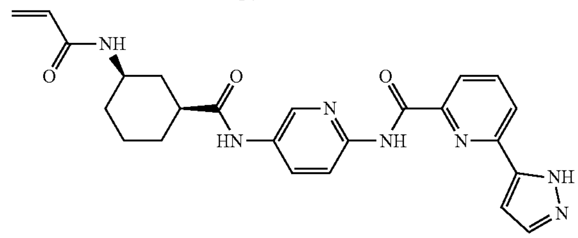

002

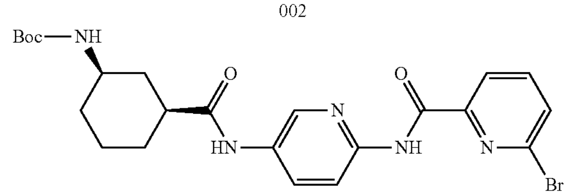

tert-butyl ((1R,3S)-3-((6-(6-bromopicolinamido)pyridin-3-yl)carbamoyl)cyclohexyl)-carbamate (12)

N-(5-aminopyridin-2.11)-6-bromopicolinamide (200 mg, 0.68 mmol) was dissolved in DMF (2 mL). (1S,3R)-3-((tert-butoxycarbonyl)amino)cyclohexane-1-carboxylic acid (183 mg, 0.75 mmol) was added followed by HATU (519 mg, 1.36 mmol) and DIEA (0.59 mL, 3.4 mmol). The mixture was stirred at room temperature until consumption of the starting material. The reaction was quenched with water (10 mL) and extracted with EtOAc (2×50 mL) washed with brine, dried over $MgSO_4$ and condensed. The resulting solid was triturated with ethyl acetate, filtered and dried to give the product which was carried forward without further purification. m/z expected: 518.42, observed: 520.04.

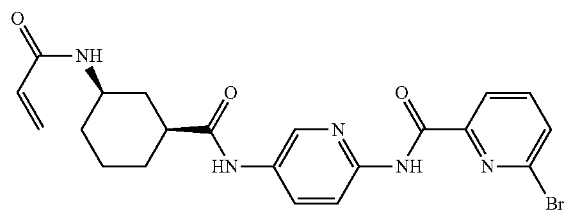 [SMILES: C=CC(=O)N[C@@H]1CCC[C@H](C(=O)Nc2ccc(NC(=O)c3cccc(Br)n3)nc2)C1]

N-(5-((1S,3R)-3-acrylamidocyclohexane-1-carboxamido)pyridin-2-yl)-6-bromopicolinamide (13)

To the suspension of tert-butyl ((1R,3S)-3-((6-(6-bromopicolinamido)pyridin-3-yl)-carbamoyl)cyclohexyl)carbamate (90 mg, 0.174 mmol) in DCM (3 mL) was added TFA (0.3 mL). The clear solution was stirred for 60 minutes and the solvent removed in vacuo. The crude was dissolved in THF (2 mL) to which was added saturated $NaHCO_3$ (aq) (2 mL) followed by slow, dropwise addition of acryloyl chloride (21 μL, 0.258 mmol). This was stirred at room temperature until consumption of starting material as monitored by LC/MS. The reaction was quenched by addition of water and extracted with EtOAc (2×10 mL) washed with brine, dried over $MgSO_4$ and condensed. The crude was carried forward without further purification. m/z expected: 473.48, observed: 474.07.

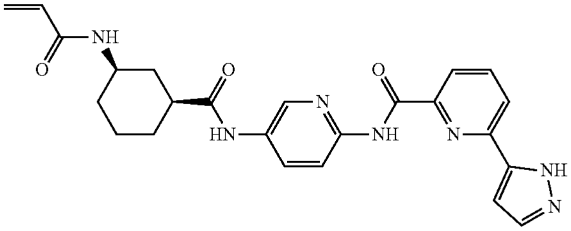 [SMILES: C=CC(=O)N[C@@H]1CCC[C@H](C(=O)Nc2ccc(NC(=O)c3cccc(-c4ccn[nH]4)n3)nc2)C1]

N-(5-((1S,3R)-3-acrylamidocyclohexane-1-carboxamido)pyridin-2-yl)-6-(1H-pyrazol-5-yl)-picolinamide (002)

The same procedure for 006 was followed to give 22 mg of the product in 59.8% yield. m/z expected: 459.51, observed: 460.20. $^{1}H$ NMR (500 MHz DMSO) δ 11.26 (br, 1H), 10.14 (s, 1H), 9.02 (br, 1H), 8.70 (s, 1H), 8.23 (d, J=8.5 Hz, 1H), 8.12-8.05 (m, 5H), 7.67 (br, 1H), 7.05 (s, 1H), 6.52 (br, 1H), 6.22-6.16 (m, 1H), 6.06 (dd, J=13 Hz, 2 Hz, 1H), 5.56 (dd, J=10 Hz, 2 Hz, 1H), 312-3.68 (m, 1H), 3.43, 3.12-3.06 (m, 1H), 1.39-1.32 (m, 3H), 1.18-1.15 (m, 3H).

Example 3: Preparation of Compound 026

Scheme 3.

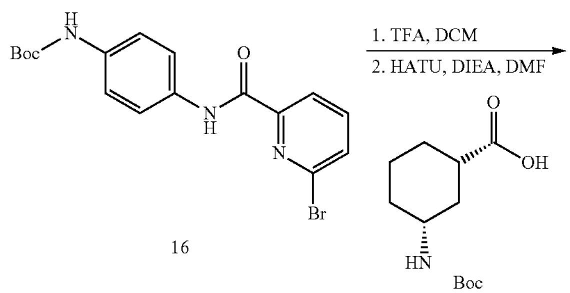

16

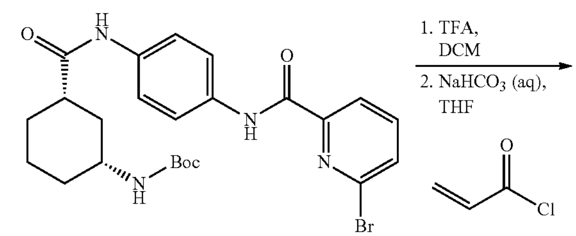

17

-continued

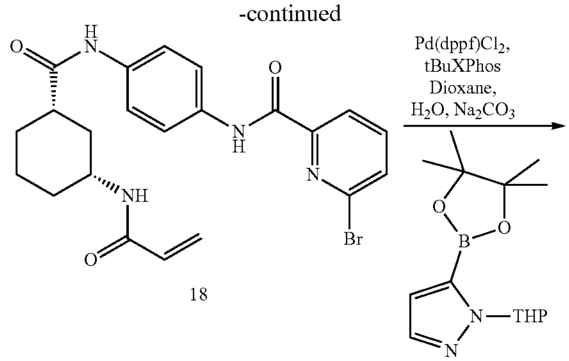

18

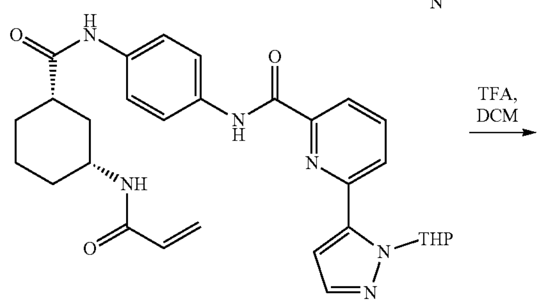

19

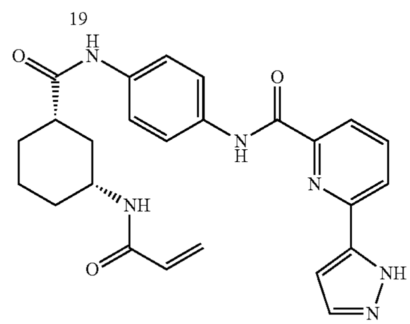

026

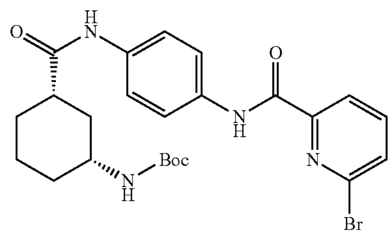

tert-butyl ((1R,3S)-3-((4-(6-bromopicolinamido) phenyl)carbamoyl)cyclohexyl)carbamate (17)

tert-butyl (4-(6-bromopicolinamido)phenyl)carbamate (200 mg, 051 mmol) was dissolved in DCM (3 mL) and TFA (0.6 mL) was added. This was stirred at room temperature for an hour and the solvent was removed in vacuo. To the crude dissolved in DMF (2 mL), was added (1S,3R)-3-((tert-butoxycarbonyl)amino)cyclohexane-1-carboxylic acid (183 mg, 0.75 mmol), DIEA (0.6 mL, 3.42 mmol), HATU (520 mg, 1.37 mmol) and stirred at room temperature. The reaction mixture was suspended in ethyl acetate, sonicated and filtered. The filtrate and the solid were checked on the LC/MS for the presence of the product. The solid was washed repeatedly with EtOAc (2×10 mL) and dried overnight under vacuum to give 48 mg of a white solid that was carried forward without any further purification. m/z expected: 517.42, observed: 419.14 (product without Boc group)

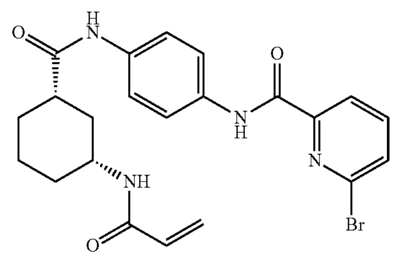 [SMILES: C=CC(=O)N[C@@H]1CCC[C@H](C(=O)Nc2ccc(NC(=O)c3cccc(Br)n3)cc2)C1]

N-(44(1S,3R)-3-acrylamidocyclohexane-1-carboxamido)phenyl)-6-bromopicolinamide (18)

The same procedure for 13 was followed to give 40 mg of a white solid that was carried forward without any further purification. m/z expected: 471.36, observed: 473.11

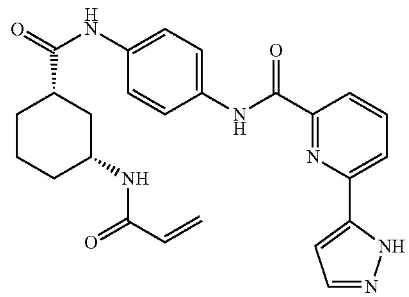 [SMILES: C=CC(=O)N[C@@H]1CCC[C@H](C(=O)Nc2ccc(NC(=O)c3cccc(-c4ccn[nH]4)n3)cc2)C1]

N-(4-((1 S,3R)-3-acrylamidocyclohexane-1-carboxamido)phenyl)-6-(1H-pyrazol-5-yl)-picolinamide (026)

The same procedure for 005 was followed to give 7 mg of a yellow solid. m/z expected: 471.36, observed: 473.11. $^1$H NMR (500 MHz, DMSO) δ 10.69 (br, 1H), 9.93 (s, 1H), 8.10-8.04 (m, 4H), 7.79 (s, 2H), 7.64 (s, 2H), 7.11 (br, 1H), 6.53 (br, 1H), 6.22-6.16 (m, 1H), 6.06 (dd, J=13 Hz, 2 Hz, 1H), 5.56 (dd, J=10 Hz, 2 Hz, 1H), 3.72-3.70 (m, 1H), 1.96-1.94 (m, 1H), 1.84-1.81 (m, 4H), 1.41-1.34 (m, 4H).

Example 4: Preparation of Compounds 027-030

Scheme 4.

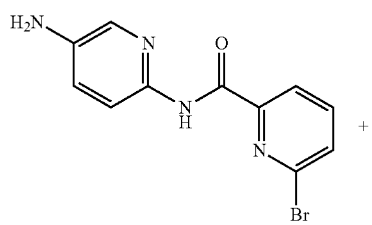

4

-continued

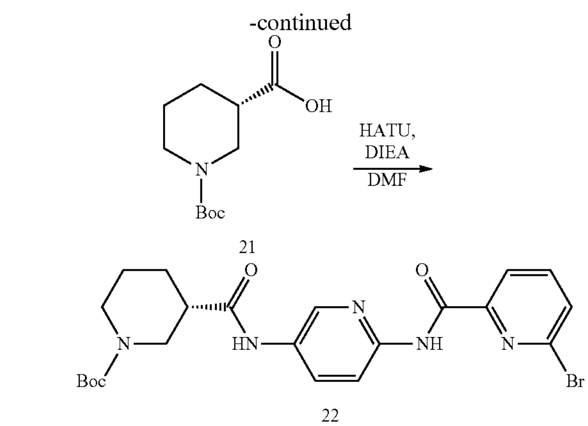

21

22

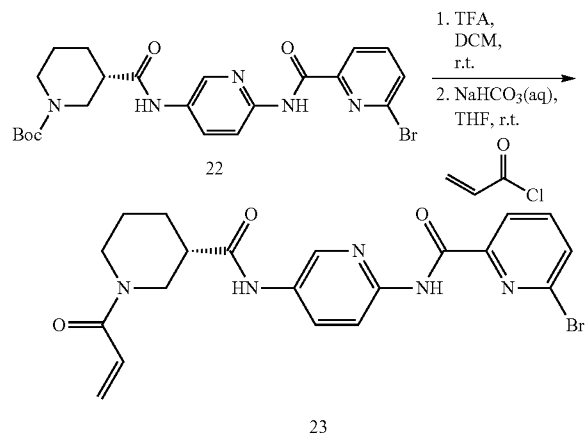

22

23

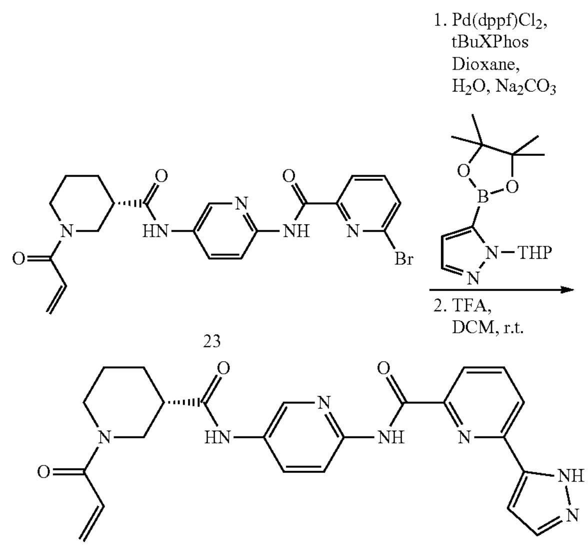

23

027

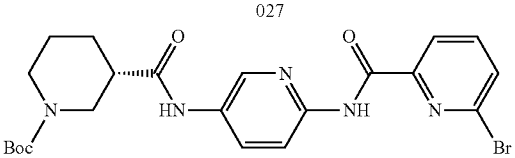

tert-Butyl (S)-34(6-(6-bromopicolinamido)pyridin-3-yl)carbamoyl)piperidine-1-carboxylate (22)

To a vial was added N-(5-aminopyridin-2-yl)-6-bromopicolinamide (500 mg, 1.71 mmol), (S)-1-(tert-butoxycarbonyl)piperidine-3-carboxylic acid (430.2 mg, 1.87 mmol), HATU (1.3 g, 3.42 mmol) and DMF (3 mL). To the stirring reaction mixture at room temperature was added DIEA (1.49 mL, 8.55 mmol) dropwise and stirred until completion of the reaction. The reaction was quenched with water, diluted with ethyl acetate. The aqueous layer was extracted with ethyl acetate (3×20 mL), combined, washed with brine, dried over $MgSO_4$, concentrated. The crude was purified by flash chromatography (10-50% ethyl acetate in hexanes) to give 550 mg of the product in 64% yield. m/z ESI expected: 504.39, observed $(M+H)^+$: 505.76. $^1$H NMR (500 MHz DMSO): δ 10.24 (s, 1H), 10.10 (s, 1H), 8.61 (s, 1H), 8.20-8.17 (m, 2H), 8.08 (dd, J=8.9 Hz, 2.6 Hz, 1H), 8.03 (t, J=7.8 Hz, 1H), 7.95 (d, J=7.85 Hz, 1H), 4.09-3.96 (m, 1H), 3.85 (d, J=13.9 Hz, 1H), 2.78 (t, J=12.2 Hz, 1H), 2.48-2.43 (m, 1H), 1.97-1.94 Om 1H), 1.73-1.70 (m, 1H), 1.67-1.58 (m, 1H), 1.42 (s, 9H), 1.38-1.36 (m, 2H).

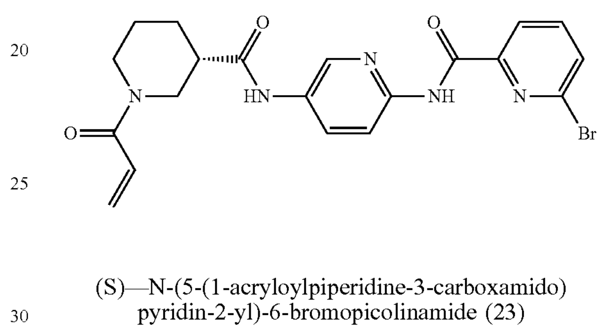

(S)—N-(5-(1-acryloylpiperidine-3-carboxamido)pyridin-2-yl)-6-bromopicolinamide (23)

Prepared according to the procedure for 13 to give 52 mg of product that was used without further purification. m/z ESI expected: 458.32, observed $(M+H)^+$: 459.77

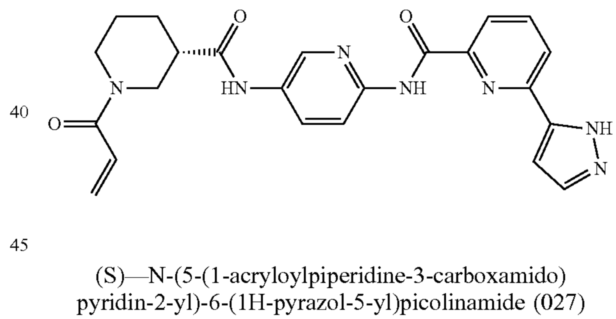

(S)—N-(5-(1-acryloylpiperidine-3-carboxamido)pyridin-2-yl)-6-(1H-pyrazol-5-yl)picolinamide (027)

Prepared according to the procedure for 10 to give the 4 mg of the product in 10% yield. m/z expected: 445.48, observed: 445.99; $^1$H NMR (500 MHz DMSO) δ 11.05 (s, 1H), 10.25 (d, J=14.9 Hz, 1H), 8.72 (s, 1H), 8.25 (d, J=9 Hz, 1H), 8.14-8.13 (m, 1H), 8.12 (s, 1H), 8.11-8.10 (m, 1H), 8.07 (dd, J=8.9 Hz, 2.6 Hz, 1H), 7.74 (s, 1H), 7.06 (s, 1H), 6.93-6.81 (m, 1H), 6.11 (dd, J=16.5 Hz, 2.5 Hz, 1H), 5.70-5.66 (m, 1H), 4.05-4.00 (m, 2H), 3.30-3.26 (m, 1H), 3.11-3.06 (m, 1H), 2.85-2.75 (m, 1H), 1.99 (s, 1H), 1.75-1.74 (m, 2H), 1.39-1.38 (m, 1H).

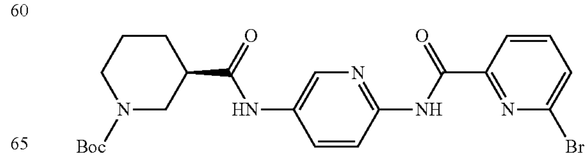

tert-butyl (R)-34(6-(6-bromopicolinamido)pyridin-3-yl)carbamoyl)piperidine-1-carboxylate (25)

Prepared according to the same procedure for 22 to give 505 mg of product in 59% yield. m/z ESI expected: 504.39, observed $(M\text{-}FH)^+$: 505.76. $^1$H NMR (500 MHz DMSO-d6): δ 10.24 (s, 1H), 10.10 (s, 1H), 8.61 (s, 1H), 8.20-8.18 (m, 2H), 8.08 (dd, J=8.9 Hz, 2.6 Hz, 1H), 8.04 (t, J=7.8 Hz, 1H), 7.96 (d, J=7.85 Hz, 1H), 4.03 (s, 1H), 3.87-3.84 (m, 1H), 2.81-2.76 (m, 2H), 2.47-2.43 (m, 1H), 1.97-1.93 (m, 1H), 1.73-1.70 (m, 1H), 1.67-1.61 (m, 1H), 1.40 (s, 9H), 1.38-1.36 (m, 2H).

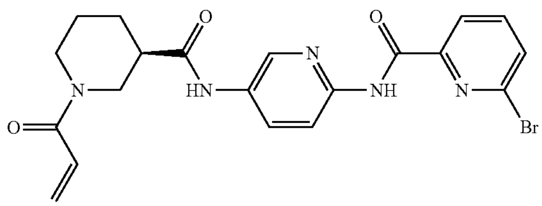 [SMILES: C=CC(=O)N1CCC[C@@H](C(=O)Nc2ccc(NC(=O)c3cccc(Br)n3)nc2)C1]

(R)—N-(5-(1-acryloylpiperidine-3-carboxamido)pyridin-2-yl)-6-bromopicolinamide (26)

Prepared according to the procedure for 13 to give 83 mg of product that was carried forward without further purification. m/z ESI expected: 458.32, observed $(M+H)^+$: 459.75

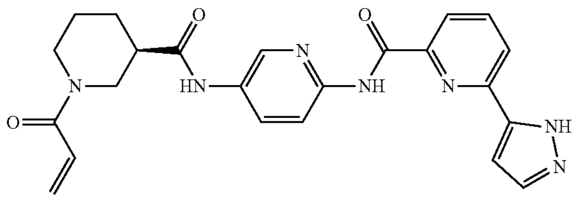

(R)—N-(5-(1-acryloylpiperidine-3-carboxamido)pyridin-2-yl)-6-(1H-pyrazol-5-yl)picolinamide (028)

Prepared according to the procedure for 10 to give 8 mg of product in 21% yield. m/z expected: 445.19, observed: 445.99; $^1$H NMR (500 MHz DMSO) δ 11.04 (s, 1H), 10.25 (d, J=15.0 Hz, 1H), 8.71 (s, 1H), 8.26 (d, J=10 Hz, 1H), 8.14-8.13 (m, 1H), 8.12 (s, 1H), 8.11-8.10 (m, 1H), 8.07 (dd, J=9.0 Hz, 2.7 Hz, 1H), 7.73 (s, 1H), 7.06 (s, 1H), 6.93-6.83 (m, 1H), 6.11 (dd, J=16.5 Hz, 2.5 Hz, 1H), 5.69-5.66 (m, 1H), 4.53-4.51 (m, 1H), 4.29-4.26 (m, 1H), 3.30-3.26 (m, 1H), 3.11-3.06 (m, 1H), 2.85-2.75 (m, 1H), 1.99 (s, 1H), 1.75-1.74 (m, 2H), 1.39-1.38 (m, 1H).

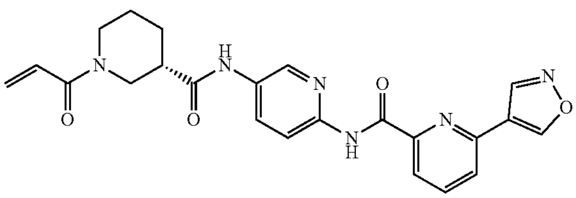 [SMILES: C=CC(=O)N1CCC[C@H](C(=O)Nc2ccc(NC(=O)c3cccc(-c4cnoc4)n3)nc2)C1]

(S)—N-(5-(1-acryloylpiperidine-3-carboxamido)pyridin-2-yl)-6-(isoxazol-4-yl)picolinamide (029)

To a solution (S)—N-(5-(1-acryloylpiperidine-3-carboxamido)pyridin-2-yl)-6-bromopicolinamide (30 mg, 0.065 mmol), in 1,4-Dioxane (2 mL), was added 4-(4,4,5,5-tetramethyl-1,3,2-dioxaborolan-2-yl)isoxazole (16.6 mg, 0.085 mmol) followed by 2M $Na_2CO_3$ (aq) (0.163 mL, 0.325 mmol). The mixture was degassed in a sonicator for 2 minutes. $Pd(dppf)Cl_2$ (5.71 mg, 0.0078 mmol) and t-BuXPhos (4.96 mg, 0.0117 mmol) were added and the mixture heated to 90° C. in a sealed vial for 1 hour. The reaction was quenched with water (5 mL) and extracted with ethyl acetate (2×10 mL) washed with brine, dried over $MgSO_4$ and concentrated in vacuo. The crude was purified by reversed phase HPLC to give the desired compound (7 mg, 26% yield). m/z expected: 446.47, observed: 446.97; H NMR (500 MHz DMSO) δ 10.7 (s, 1H), 10.26 (d, J=14.95 Hz, 1H), 9.9 (s, 1H), 9.54 (s, 1H), 8.68 (s, 1H), 8.22 (d, J=8.9 Hz, 1H), 8.18-8.15 (m, 1H), 8.12 (s, 1H), 8.11-8.10 (m, 1H), 8.09-8.08 (m, 1H), 6.93-6.81 (m, 1H), 6.11 (dd, J=16.5 Hz, 2.5 Hz, 1H), 5.70-5.66 (m, 1H), 4.53-4.51 (m, 1H), 4.3-4.28 (m, 1H), 4.16-4.13 (m, 1H), 4.05-4.02 (m, 1H), 3.11-3.06 (m, 1H), 2.89-2.73 (m, 1H), 2.02-2.00 (m, 1H), 1.77-1.75 (m, 2H), 1.39-1.38 (m, 1H).

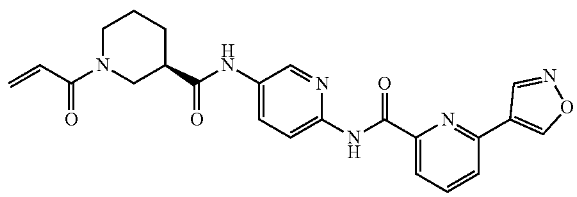 [SMILES: C=CC(=O)N1CCC[C@@H](C(=O)Nc2ccc(NC(=O)c3cccc(-c4cnoc4)n3)nc2)C1]

(R)—N-(5-(1-acryloylpiperidine-3-carboxamido)pyridin-2-yl)-6-(isoxazol-4-yl)picolinamide (030)

Prepared according to the procedure for 029 to give 14 mg of product in 51% yield. m/z expected: 446.47, observed: 447.25; $^1$H NMR (500 MHz DMSO) δ 10.7 (s, 1H), 10.26 (d, 1H, J=14.95 Hz), 9.9 (s, 1H), 9.54 (s, 1H), 8.68 (s, 1H), 8.22 (d, 1H, J=8.9 Hz), 8.18-8.15 (m, 1H), 8.12 (s, 1H), 8.11-8.10 (m, 1H), 8.09-8.08 (m, 1H), 6.93-6.81 (m, 1H), 6.11 (dd, 1H, J=16.5 Hz, 2.45 Hz), 5.70-5.66 (m, 1H), 4.54-4.52 (m, 1H), 3.3-3.25 (m, 1H), 3.11-3.06 (m, 1H), 2.85-2.74 (m, 1H), 2.02-2.00 (m, 1H), 1.77-1.75 (m, 2H), 1.40-1.38 (m, 1H).

Example 5: Preparation of Compounds 031-034

Scheme 5.

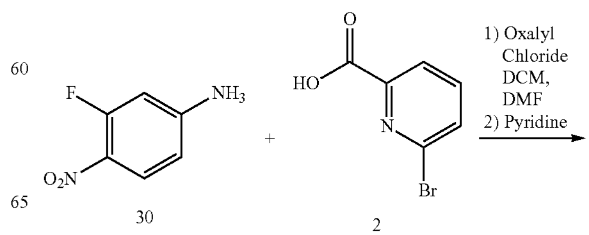

30

2

-continued

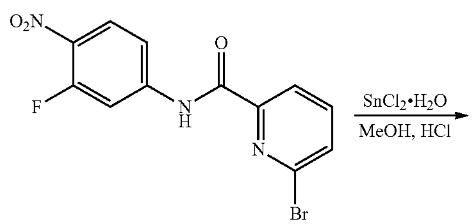

31

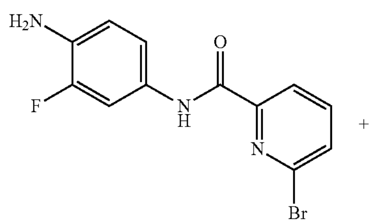

32

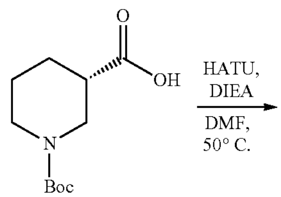

5

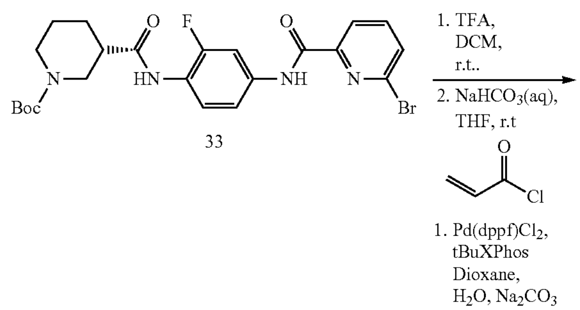

33

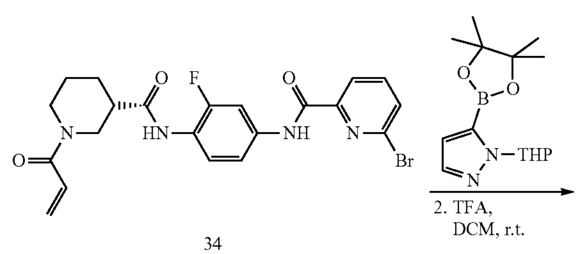

34

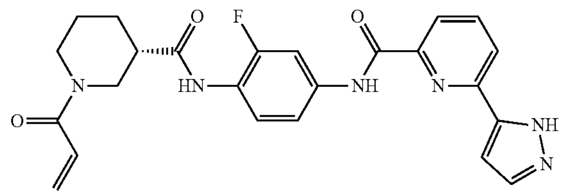

031

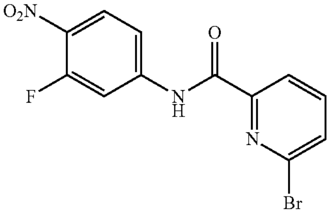

6-bromo-N-(3-fluoro-4-nitrophenyl)picolinamide (31)

Prepared according to the procedure for 3 to give 3.1 g of product that used in the next step without further purification. m/z ESI expected: 340.11, observed (Ml-FH)$^+$: 341.28

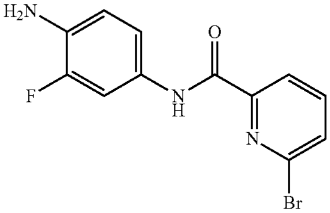 [SMILES: O=C(Nc1ccc([N+](=O)[O-])c(F)c1)c1cccc(Br)n1]

N-(4-amino-3-fluorophenyl)-6-bromopicolinamide (32)

Prepared according to the procedure for 4 to give the desired product that used in the next step without further purification. m/z ESI expected: 310.13

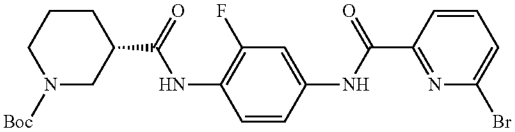 [SMILES: CC(C)(C)OC(=O)N1CCC[C@H](C(=O)Nc2ccc(NC(=O)c3cccc(Br)n3)cc2F)C1]

tert-butyl (S)-3-((4-(6-bromopicolinamido)-2-fluorophenyl)carbamoyl)piperidine-1-carboxylate (33)

Prepared according to the procedure for 22 to give 445 mg of the product in 53% yield. m/z ESI expected: 521.39, observed (M+H)$^+$: 522.8. $^1$H NMR (500 MHz DMSO-d6): δ 10.57 (s, 1H), 9.74 (s, 1H), 8.13 (dd, J=7.6 Hz, 1.1 Hz, 1H), 8.0 (t, J=10 Hz, 1H), 7.93 (dd, J=7.9 Hz, 1.1 Hz, 1H), 7.89 (dd, J=13.1 Hz, 2.4 Hz, 1H), 7.81-7.74 (m, 1H), 7.65-7.62 (m, 1H), 4.05-4.01 (m, 1H), 3.98-3.85 (m, 1H), 2.79-2.74 (m, 1H), 2.63-2.57 (m, 1H) 1.99-1.93 (m, 2H), 1.71-1.69 (m, 2H), 1.64-1.56 (m, 1H), 1.40 (s, 9H); 1.39-1.38 (m, 2H).

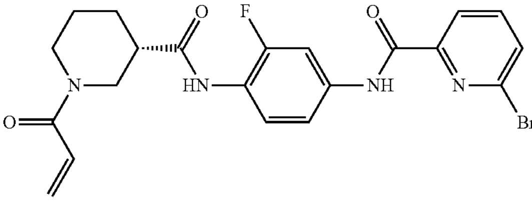 [SMILES: C=CC(=O)N1CCC[C@H](C(=O)Nc2ccc(NC(=O)c3cccc(Br)n3)cc2F)C1]

(S)—N-(4-(1-acryloylpiperidine-3-carboxamido)-3-fluorophenyl)-6-bromopicolinamide (34)

Prepared according to the procedure for 13 to give 89 mg of product that was used without further purification. m/z ESI expected: 475.32, observed (M-FH)$^+$: 476.32

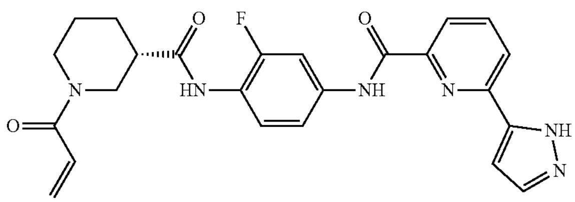 [SMILES: C=CC(=O)N1CCC[C@H](C(=O)Nc2ccc(NC(=O)c3cccc(-c4ccn[nH]4)n3)cc2F)C1]

(S)—N-(4-(1-acryloylpiperidine-3-carboxamido)-3-fluorophenyl)-6-(1H-pyrazol-5-yl)picolinamide (031)

Prepared according to the procedure for 10 to give the desired compound (9 mg, 24% yield). m/z expected: 462.49, observed: 463.22; $^1$H NMR (500 MHz DMSO) δ 10.72 (s, 1H), 9.79 (s, 1H), 8.15-8.10 (m, 2H), 8.08-8.06 (m, 1H), 7.92 (dd, 1H, J=12.9 Hz, 2.3 Hz), 7.87-7.80 (m, 1H), 7.74 (s, 1H), 7.65-7.64 (d, 1H, J=6.2 Hz), 7.2 (s, 1H), 6.93-6.81 (m, 1H), 6.1 (d, 1H, J=16.4 Hz), 5.69-5.67 (m, 1H), 4.52-4.50 (m, 1H), 4.28-4.25 (m, 1H), 4.12-4.01 (m, 1H), 3.09-3.05 (m; 1H), 2.83-2.75 (m, 1H), 2.64-2.58 (m, 1H), 2.00-1.98 (m, 1H), 1.79-1.70 (m, 2H), 1.71-1.69 (m, 2H), 1.38-1.37 (m, 1H).

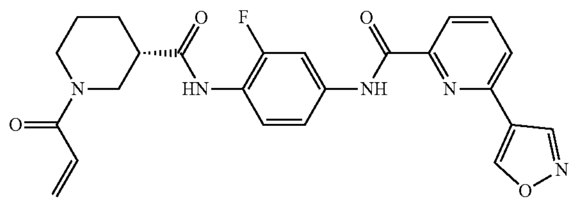 [SMILES: C=CC(=O)N1CCC[C@H](C(=O)Nc2ccc(NC(=O)c3cccc(-c4cnoc4)n3)cc2F)C1]

(S)—N-(4-(1-acryloylpiperidine-3-carboxamido)-3-fluorophenyl)-6-(isoxazol-4-yl)picolinamide (032)

Prepared according to the procedure for 029 to give the desired compound (7 mg, 26% yield). m/z expected: 463.47, observed: 463.88; $^1$H NMR (500 MHz DMSO) δ 10.91 (s, 1H), 10.59 (s, 1H), 9.78 (d, J=24.9 Hz, 1H), 9.01 (d, J=7.0 Hz, 1H), 8.24-8.21 (m, 1H), 8.05-8.01 (m, 1H), 7.93-7.88 (m, 1H), 7.83-7.75 (m, 1H), 7.61-7.49 (m, 2H), 6.91-6.8 (m, 1H), 6.53 (s, 1H), 6.1 (d, J=16.5 Hz, 1H), 5.69-5.67 (m, 1H), 4.51-4.49 (m, 1H), 4.28-4.24 (m, 1H), 4.1-4.01 (m, 2H), 3.09-3.04 (m, 1H), 2.80-2.77 (m, 1H), 2.64-2.60 (m, 1H), 1.99-1.97 (m, 1H), 1.75-1.68 (m, 2H), 1.37-1.36 (m, 1H).

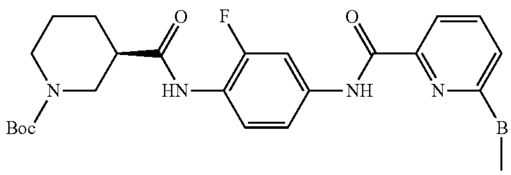

tert-butyl (R)-3-((4-(6-bromopicolinamido)-2-fluorophenyl)carbamoyl)piperidine-1-carboxylate (37)

Prepared according to the procedure for 22 to give 444 mg of the product in 53% yield. m/z ESI expected: 521.39, observed (M+H)$^+$: 522.7. $^1$H NMR (500 MHz DMSO-d6): δ 10.57 (s, 1H), 9.74 (s, 1H), 8.13 (dd, J=7.6 Hz, 1.1 Hz, 1H), 8.0 (t, J=10 Hz, 1H), 7.93 (dd, J=7.9 Hz, 1.1 Hz, 1H), 7.89 (dd, J=13.1 Hz, 2.4 Hz, 1H), 7.81-7.75 (m, 1H), 7.65-7.63 (m, 1H), 4.05-4.01 (m, 1H), 3.87-3.84 (m, 1H), 2.79-2.74 (m, 1H), 2.62-2.57 (m, 1H) 1.96-1.93 (m, 2H), 1.71-1.69 (m, 2H), 1.64-1.56 (m, 1H), 1.40 (s, 9H), 1.39-1.38 (m, 2H).

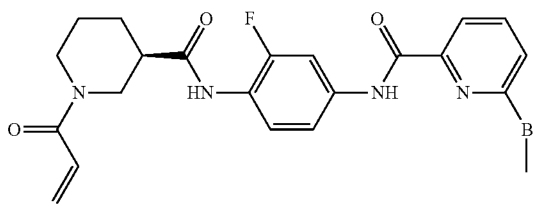

(R)—N-(4-(1-acryloylpiperidine-3-carboxamido)-3-fluorophenyl)-6-bromopicolinamide (38)

Prepared according to the procedure for 13 to give 88 mg of product that was used without further purification. m/z ESI expected: 475.32, observed (M+H)$^+$: 476.32

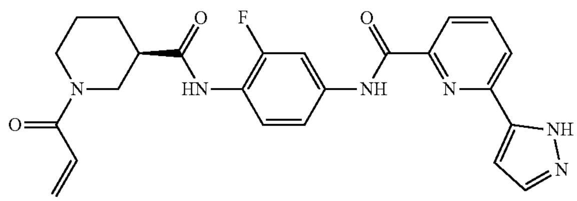

(R)—N-(4-(1 acryloylpiperidine-3-carboxamido)-3-fluorophenyl)-6-(1H-pyrazol-5-yl)picolinamide (033)

Prepared according to the procedure for 10 to give 14 mg of product in 35% yield. m/z expected: 462.49, observed: 463.22; $^1$H NMR (500 MHz DMSO) δ 10.72 (s, 1H), 9.79 (s, 1H), 8.15-8.10 (m, 2H), 8.08-8.07 (m, 1H), 7.92 (del, 1H, J=12.9 Hz, 2.3 Hz), 7.87-7.80 (m, 1H), 7.74 (s, 1H), 7.65-7.64 (d, 1H, J=6.2 Hz), 7.2 (s, 1H), 6.93-6.81 (m, 1H), 6.1 (d, 1H, J=16.4 Hz), 5.69-5.67 (m, 1H), 4.52-4.50 (m, 1H), 4.28-4.25 (m, 1H), 4.12-4.01 (m, 1H), 3.09-3.05 (m, 1H), 2.83-2.75 (m, 1H), 2.66-2.60 (m, 1H), 2.00-1.98 (m, 1H), 1.79-1.70 (m, 2H), 1.71-1.69 (m, 2H), 1.38-1.37 (m, 1H).

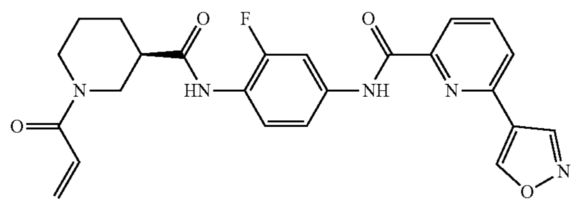 [SMILES: C=CC(=O)N1CCC[C@@H](C(=O)Nc2ccc(NC(=O)c3cccc(-c4cnoc4)n3)cc2F)C1]

(R)—N-(4-(1-acryloylpiperidine-3-carboxamido)-3-fluorophenyl)$_{66}$-(isoxazol-4-yl)picolinamide (034)

Prepared according to the procedure for 029 to give 8 mg of product in 27% yield. m/z expected: 463.47, observed: 463.88; $^1$H NMR (500 MHz DMSO) δ 10.91 (s, 1H), 10.59 (s, 1H), 9.79 (d, J=24.2 Hz, 1H), 9.02 (d, J=10.2 Hz, 1H), 8.23-8.20 (m, 1H), 8.03-8.00 (m, 1H), 7.92-7.86 (m, 1H), 7.83-7.75 (m, 1H), 7.62-7.48 (m, 2H), 6.92-6.8 (m, 1H), 6.52 (s, 1H), 6.1 (d, J=16.5 Hz, 1H), 5.69-5.66 (m, 1H), 4.51-4.49 (m, 1H), 4.26-4.24 (m, 1H), 4.09-4.01 (m, 1H), 3.09-3.04 (m, 1H), 2.80-2.73 (m, 1H), 2.64-2.59 (m, 1H), 1.99-1.97 try, 1H), 1.75-1.68 (m, 2H), 1.37-1.36 (m, 1H).

Example 6: Preparation of Compounds 035 and 036

Scheme 6.

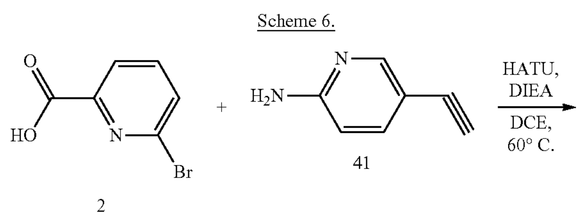

2 41

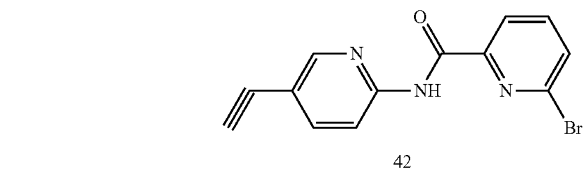

42

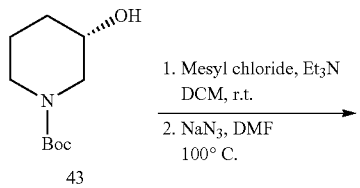

43

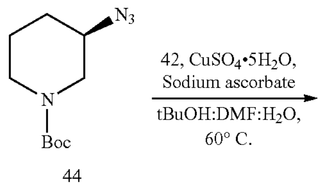

44

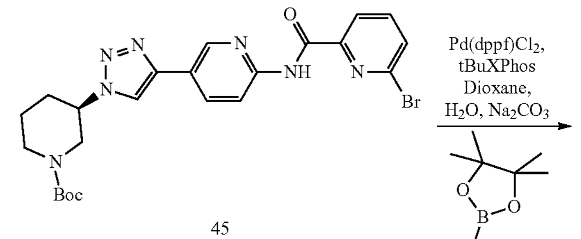

45

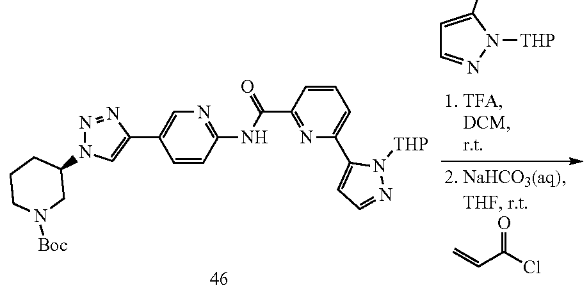

46

-continued

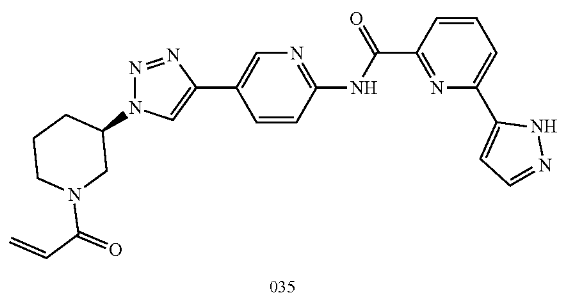

035

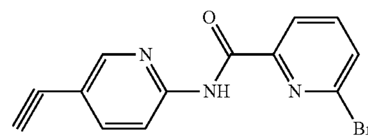

6-bromo-N-(5-ethynylpyridine-2-yl)picolinamide (42)

Prepared according to the procedure for 22 to give 550 mg of the product in 24% yield. m/z ESI expected: 302.15, observed (M+H)$^+$: 304.87. $^1$H NMR (500 MHz DMSO-d6): δ 10.25 (s, 1H), 8.23 (d, J=9.6 Hz, 1H), 8.18 (dd, J=7.5 Hz, 1 Hz, 1H), 8.03 (dd, J=10 Hz, 5 Hz, 1H), 7.99 (dd, J=8.6 Hz, 2.3 Hz, 1H), 7.96 (dd, J=7.9 Hz, 1.0 Hz, 1H), 4.38 (s, 1H),

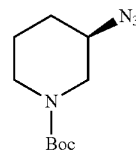

tert-butyl (R)-3-azidopiperidine-1-carboxylate (44)

To a flask containing tert-butyl (S)-3-hydroxypiperidine-1-carboxylate (1 g, 4.96 mmol) in DCM (5 mL) was added TEA (1.38 mL, 9.92 mmol) at 0° C. and mesyl chloride (0.46 mL, 5.96 mmol) dropwise and set to stir until completion of reaction. The solvents were evaporated in vacuo, the crude was dissolved in ethyl acetate and washed with $NaHCO_3$ (aq) (3×10 mL). The organic layers were washed with brine, dried over $MgSO_4$, concentrated. The crude was dissolved in DMF (2 mL) and $NaN_3$ (2.56 g, 39.68 mmol) was added and stirred at 100° C. until consumption of the starting mesylate material. The reaction mixture was diluted with ethyl acetate, washed with $NaHCO_3$ (aq) (3×10 mL). The organic layers were washed with brine, dried over $MgSO_4$, concentrated. The crude was purified by flash chromatography (2%-25% ethyl acetate in hexanes) to give 479 mg of the product in 43% yield. m/z expected: 226.28, observed: 170.91 (without the BOO group); $^1$H NMR (500 MHz DMSO) δ 3.69 (s, 1H), 3.58-3.40 (m, 2H), 3.29-3.17 (m, 2H), 1.82 (s, 1H), 1.58 (s, 2H), 1.4 (s, 9H), 1.38-1.35 (m, 1H).

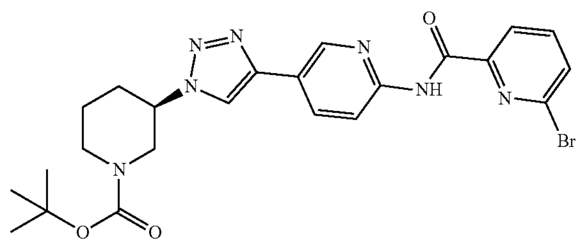 [SMILES: CC(C)(C)OC(=O)N1CCC[C@@H](n2cc(-c3ccc(NC(=O)c4cccc(Br)n4)nc3)nn2)C1]

tert-butyl (R)-3-(4-(6-(6-bromopicolinamido)pyridin-3-yl)-1H-1,2,3-triazol-1-yl)piperidine-1-carboxylate (45)

To a vial containing 6-bromo-N-(5-ethynylpyridine-2-yl) picolinamide (150 mg, 0.49 mmol) in 1:1:1 DMF:water:tert-butanol (3 mL) was added tert-butyl (R)-3-azidopiperidine-1-carboxylate (110.88 mg, 0.49 mmol), $CuSO_4 \cdot 5H_2O$ (125 mg, 0.49 mmol), sodium ascorbate (99.1 mg, 0.49 mmol) and stirred at 60° C. until completion of reaction. The reaction mixture was quenched with water, filtered. The solid was dissolved in DMSO and purified by reverse phase HPLC to give 189 mg of product in 73% yield. m/z expected: 528.41, observed:

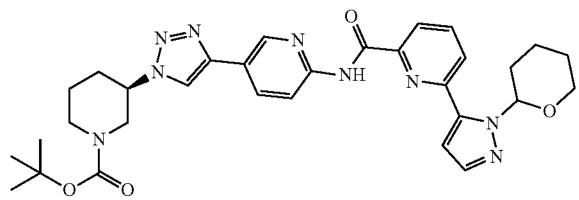 [SMILES: CC(C)(C)OC(=O)N1CCC[C@@H](n2cc(-c3ccc(NC(=O)c4cccc(-c5ccnn5C5CCCCO5)n4)nc3)nn2)C1]

tert-butyl (3R)-3-(4-(6-(6-(1-(tetrahydro-2H-pyran-2-yl)-1H-pyrazol-5-yl)picolinamido)pyridin-3-yl)-1H-1,2,3-triazol-1-yl)piperidine-1-carboxylate (46)

Prepared according to the procedure for 10 to give the desired compound (42 mg, 74% yield), m/z expected: 599.7, observed: 600.23; $^1$H NMR (500 MHz, DMSO) δ 11.17 (s, 1H), 10.65 (s, 1H), 8.94 (dd, J=19 Hz, 2.4 Hz, 1H), 8.79 (d, J=5.4 Hz, 1H), 8.42-8.39 (m, 1H), 8.35-8.33 (m, 1H), 8.15-8.13 (m, 3H), 7.74 (s, 1H), 7.17 (s, 1H), 7.07 (s, 1H), 5.54 (d, J=12.4 Hz, 1H), 4.62 (s, 1H), 4.21-4.00 (m, 1H), 3.82-3.68 (m, 2H), 3.51-3.26 (m, 2H), 3.04 (s, 2H), 2.27-2.25 (m, 1H), 2.21-2.13 (m, 1H), 2.03-1.99 (m, 1H), 183 (s, 1H), 1.77-1.68 (m, 1H), 1.63-1.54 (m, 2H), 1.40 (s, 9H).

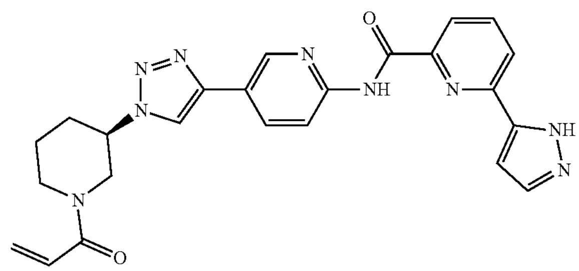 [SMILES: C=CC(=O)N1CCC[C@@H](n2cc(-c3ccc(NC(=O)c4cccc(-c5ccn[nH]5)n4)nc3)nn2)C1]

(R)—N-(5-(1-(1-acryloylpiperidin-3-yl)-1H-1,2,3-triazol-4-yl)pyridin-2-yl)-6-(1H-pyrazol-5-yl)picolinamide (035)

To a solution of tort-butyl (3R)-3-(4-(6-(6-(1-(tetrahydro-2H-pyran-2-yl)-1H-pyrazol-5-yl)picolinamido)pyridin-3-yl)-1H-1,2,3-triazol-1-yl)piperidine-1-carboxylate (150 mg, 0.25 mmol) in dichloromethane (10 mL), was added trifluoroacetic acid (1 mL, 10% v/v) and stirred at room temperature until consumption of starting material. The solvents were removed in vacuo; the crude was dissolved in THE (2 mL), $NaHCO_3$ (aq) (2 mL), followed by acryloyl chloride (17.2 μL, 0.211 mmol) were added and the mixture stirred for 15 minutes. The reaction was quenched with water, extracted with ethyl acetate (3×20 mL), combined, washed with brine, dried over $MgSO_4$, purified by reverse phase HPLC to give 59 mg of product in 51% yield. m/z ESI expected: 469.51, observed: 470.01; $^1$H NMR (500 MHz, DMSO) δ 11.18 (s, 1H), 8.94 (s, 1H), 8.82 (s, 1H), 8.41 (d, J=8.6 Hz, 1H), 8.35 (dd, J=8.7 Hz, 2.4 Hz, 1H), 8.17-8.13 (m, 3H), 7.74 (s, 1H), 7.07 (s, 1H), 6.89-6.84 (m, 1H), 6.17-6.09 (m, 1H), 5.74-5.67 (m, 1H), 4.68-4.62 (m, 2H), 4.33-4.02 (m, 2H), 3.75-3.71 (m, 1H), 3.29-3.22 (m, 1H), 3.09-3.05 (m, 1H), 2.35-2.30 (m, 1H), 2.21-2.17 (m, 1H), 1.91-1.88 (m, 1H) 1.61 (s, 1H).

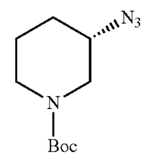 [SMILES: CC(C)(C)OC(=O)N1CCC[C@H](N=[N+]=[N-])C1]

tert-butyl (S)-3-azidopiperidine-1-carboxylate (48)

Prepared according to the procedure for 44 to give 600 mg of the product in 53% yield. m/z expected: 226.28, observed: 170.91 (without the BOO group); $^1$H NMR (500 MHz DMSO) δ); $^1$H NMR (500 MHz DMSO) δ 3.69 (s, 1H), 3.58-3.40 (m, 2H), 3.29-3.17 (m, 2H), 1.82 (s, 1H), 1.58 (s, 2H), 1.4 (s, 9H), 1.38-1.35 (m, 1H).

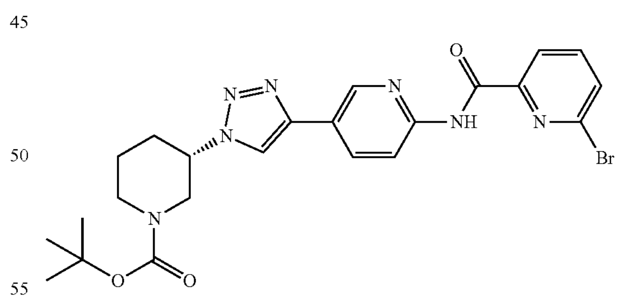

tert-butyl (S)-3-(4-(6-(6-bromopicolinamido)pyridin-3-yl)-1H-1,2,3-triazol-1-yl)piperidine-1-carboxylate (49)

Prepared according to the procedure for 45 to give 193 mg of product in 74% yield, m/z expected: 528.41, observed: 528.98; 1H NMR (500 MHz DMSO) δ); 1H NMR (500 MHz DMSO) δ 10.26 (s, 1H), 8.87 (s, 1H), 8.79 (s, 1H), 8.36 (s, 1H), 8.21 (d, J=7.5 Hz, 1H), 8.06 (t, J=7.6 Hz, 1H), 7.99 (d, J=7.9 Hz, 1H), 4.62 (s, 1H), 4.21 (s, 2H), 3.77 (s, 1H), 3.52-3.25 (m, 1H), 3.04 (s, 1H), 2.27-2.24 (m, 1H), 2.17-2.11 (m, 1H), 1.86-1.81 (m, 1H), 1.62-1.55 (m, 1H), 1.39 (s, 9H),

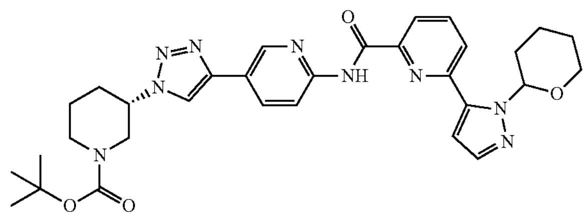 [SMILES: CC(C)(C)OC(=O)N1CCC[C@H](n2cc(-c3ccc(NC(=O)c4cccc(-c5ccnn5C5CCCCO5)n4)nc3)nn2)C1]

tert-butyl (3S)-3-(4-(6-(6-(1-(tetrahydro-2H-pyran-2-yl)-1H-pyrazol-5-yl)picolinamido)pyridin-3-yl)-1H-1,2,3-triazol-1-yl)piperidine-1-carboxylate (50)

Prepared according to the procedure for 10 to give 125 mg of product in 63% yield, m/z expected: 599.7, observed: 600.23; $^1$H NMR (500 MHz, DMSO) δ 10.65 (s, 1H), 8.91 (dd, J=18.7 Hz, 3 Hz, 1H), 8.78 (d, J=5.1 Hz, 1H), 8.42-8.39 (m, 1H), 8.36-8.33 (m, 1H), 8.23-8.22 (m, 1H), 8.16-8.13 (m, 3H), 8.07 (d, J=2.5 Hz, 1H), 7.74 (s, 1H), 7.18 (s, 1H), 7.08 (s, 1H), 5.54 (d, J=12.4 Hz, 1H), 4.62 (s, 1H), 4.00-3.96 (m, 1H), 3.72-3.66 (m, 1H), 3.04 (s, 1H), 2.27-2.21 (m, 1H), 2.17-2.11 (m, 2H), 2.02-1.98 (m, 1H), 1.83 (s, 1H), 1.75-1.68 (m, 1H), 1.59-1.57 (m, 1H), 1.39 (s, 9H).

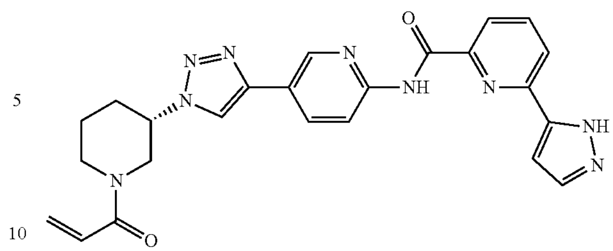

(S)—N-(5-(1-(1-acryloylpiperidin-3-yl)-1H-1,2,3-triazol-4-yl)pyridin-2-yl)-6-(1H-pyrazol-5-yl)picolinamide (036)

Prepared according to the procedure for 035 give 49 mg of product in 62% yield. m/z expected: 469.51, observed: 470.01; $^1$H NMR (500 MHz, DMSO) δ 11.18 (s, 1H), 8.94 (s, 1H), 8.82 (s, 1H), 8.41 (d, J=8.5 Hz, 1H), 8.34 (dd, J=8.6 Hz, 2.4 Hz, 1H), 8.17-8.12 (m, 3H), 7.74 (s, 1H), 7.07 (s, 1H), 6.89-6.84 (m, 1H), 6.17-6.09 (m, 1H), 5.74-5.67 (m, 1H), 4.68-4.62 (m, 2H), 4.33-4.13 (m, 1H), 4.05-3.71 (m, 1H), 3.29-3.22 (m, 1H), 3.09-3.05 (m, 1H), 2.36-2.31 (m, 1H), 2.21-2.17 (m, 1H), 1.88 (s, 1H), 1.61 (s, 1H).

Example 7: Preparation of Compounds 037, 024, and 025

Scheme 7.

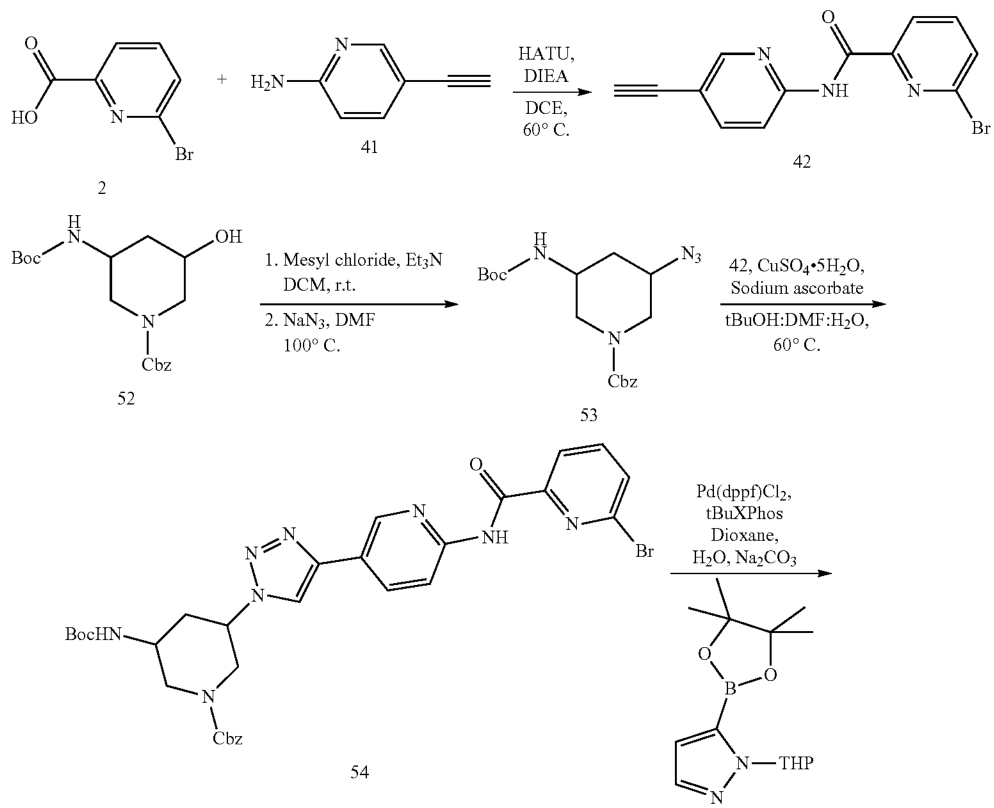

2 41 42 52 53 54

-continued

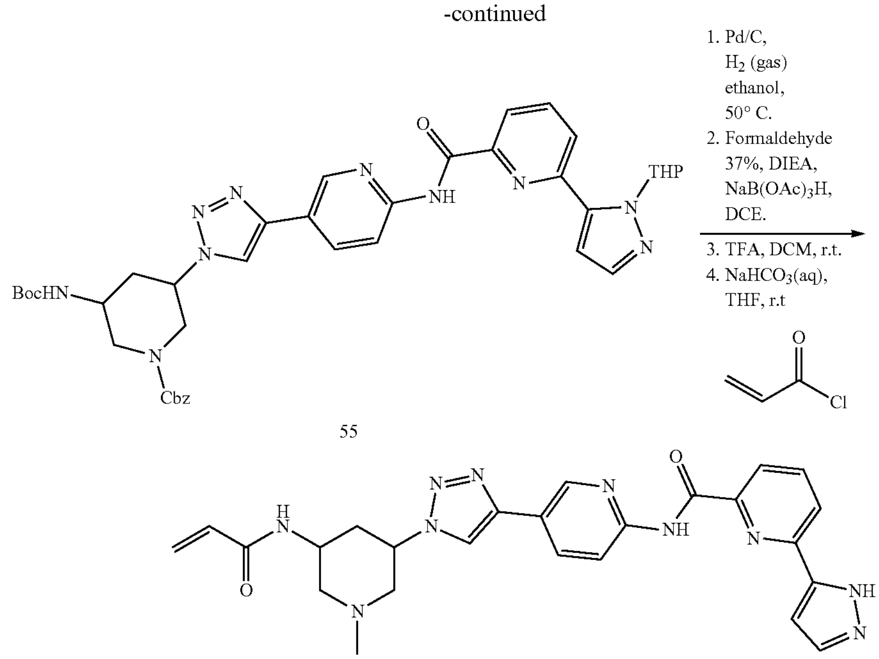

55

037

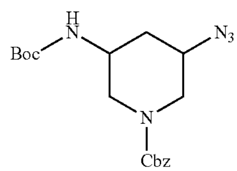

benzyl 3-azido-5-((tert-butoxycarbonyl)amino)piperidine-1-carboxylate (53)

Prepared according to the procedure for 44 to give 410 mg of product in 38% yield. m/z expected: 275.31, observed: 275.85 (without the BOO group); $^1$H NMR (500 MHz DMSO) δ 7.37-7.29 (m, 5H), 6.96 (d, J=7.9 Hz, 1H), 5.1 (s, 2H), 4.05-3.99 (m, 1H), 3.66-3.60 (m, 1H), 3.41 (s, 1H), 2.64 (s, 1H), 2.16-2.14 (m, 1H), 1.83 (s, 1H), 1.4 (s, 2H), 1.38 (s, 9H).

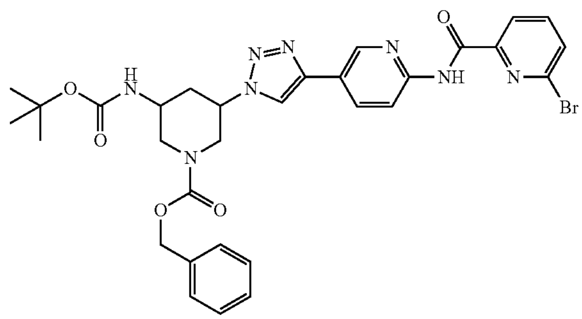 [SMILES: CC(C)(C)OC(=O)NC1CC(n2cc(-c3ccc(NC(=O)c4cccc(Br)n4)nc3)nn2)CN(C(=O)OCc2ccccc2)C1]

benzyl 3-(4-(6-(6-bromopicolinamido)pyridin-3-yl)-1H-1,2,3-triazol-1-yl)-5-((tert-butoxycarbonyl) amino)piperidine-1-carboxylate (54)

Prepared according to the procedure for 45 to give 80 mg of product in 56% yield. m/z expected: 677.56, observed: 677.03. $^1$H NMR (500 MHz DMSO) δ 10.26 (s, 1H), 8.87 (s, 1H), 8.79 (s, 1H), 8.34 (s, 2H), 8.22 (d, J=6.5 Hz, 1H), 8.06 (t, J=7.5 Hz, 1H), 7.99 (d, J=9 Hz, 1H), 7.39-7.36 (m, 4H), 7.33-7.32 (m, 1H), 7.20-7.17 (m, 1H), 5.15 (s, 2H), 4.77 (s, 2H), 4.44-4.42 (m, 1H), 4.19-4.17 (m, 1H), 3.61 (s, 1H), 2.44-2.42 (m, 2H), 2.01-1.98 (m, 1H), 1.4 (s, 9H).

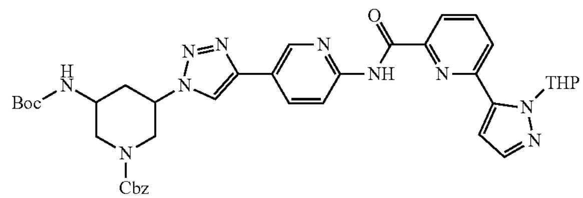

benzyl 3-((tert-butoxycarbonyl)amino)-5-(4-(6-(6-(1-(tetrahydro-2H-pyran-2-yl)-1H-pyrazol-5-yl)picolinamido)pyridin-3-yl)-1H-1,2,3-triazol-1-yl)piperidine-1-carboxylate (55)

Prepared according to the procedure for 10 to give 100 mg of product in 43% yield, m/z expected: 748.85, observed: 749.23. $^1$H NMR (500 MHz DMSO) δ 11.17 (s, 1H), 10.64 (s, 1H), 8.92 (dd, J=19.8 Hz, 2.8 Hz, 1H), 8.90-8.79 (m, 1H), 8.40 (dd, J=8.7 Hz, 6.5 Hz, 1H), 8.36-8.33 (m, 1H), 8.16-8.13 (m, 2H), 7.74 (s, 1H), 7.39-7.31 (m, 5H), 7.20-7.17 (m, 1H), 7.07 (s, 1H), 5.54 (dd, J=10 Hz, 2.4 Hz, 1H), 5.16 (s, 2H), 4.77 (s, 2H), 4.45-4.43 (m, 1H), 4.20-4.17 (m, 1H), 3.99-3.97 (m, 1H), 3.71-3.62 (m, 2H), 3.13 (s, 1H), 2.63 (s, 1H), 2.46-2.43 (m, 1H), 2.22-2.14 (m, 1H), 2.02-1.97 (m, 2H), 1.76-1.73 (m, 1H), 1.61-1.57 (m, 1H), 1.4 (s, 9H).

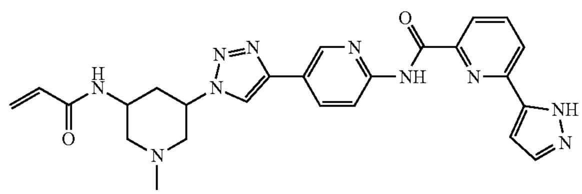 [SMILES: C=CC(=O)NC1CC(n2cc(-c3ccc(NC(=O)c4cccc(-c5ccn[nH]5)n4)nc3)nn2)CN(C)C1]

N-(5-(1-(5-acrylamido-1-methylpiperidin-3-yl)-1H-1,2,3-triazol-4-yl)pyridin-2-yl)-6-(1H-pyrazol-5-yl) picolinamide (037)

To a flask containing 10% Pd on C (1.42 mg, 0.0134 mmol) in ethanol (5 mL) was added benzyl 3-((tert-butoxycarbonyl)amino)-5-(4-(6-(6-(1-(tetrahydro-2H-pyran-2-yl)-1H-pyrazol-5-yl)picolinamido)pyridin-3-yl)-1H-1,2,3-triazol-1-yl)piperidine-1-carboxylate (100 mg, 0.134 mmol) and stirred at 50° C. under a hydrogen atmosphere until completion of reaction. The reaction mixture was filtered through a pad of celite, washed with ethyl acetate and the solvents removed in vacuo. The crude was dissolved in 1,2 dichloroethane to which was added 37% formaldehyde solution in water (0.0335 mL, 0.45 mmol) and DIEA (0.068 mL, 0.39 mmol) and stirred for 30 minutes at room temperature. $NaB(OAc)_3H$ (96.4 mg, 0.45 mmol) was added and the reaction stirred until completion. The reaction mixture was quenched, extracted with ethyl acetate, washed with brine, dried over $MgSO_4$ and concentrated. The crude was then subjected to a procedure similar for 47 and purified by reverse phase HPLC to obtain 15 mg of product in 24% yield. m/z expected: 498.55, observed: 499.04. $^1H$ NMR (500 MHz DMSO) δ11.18 (s, 1H), 8.95 (s, 1H), 8.85 (s, 1H), 8.55 (s, 1H), 8.43 (d, J=8.6 Hz, 1H), 8.35 (dd, J=8.5 Hz, 2.4 Hz, 1H), 8.16-8.14 (m, 3H), 7.75 (s, 1H), 7.07 (s, 1H), 6.27-6.15 (m, 2H), 5.71 (dd, J=9.8 Hz 2.5 Hz, 1H), 5.05 (s, 1H), 4.31 (s, 1H), 3.95 (s, 1H), 3.65-3.56 (m, 2H), 2.57-2.54 (m, 1H), 2.95 (s, 3H), 2.91 (s, 1H), 2.22-2.08 (m, 1H)

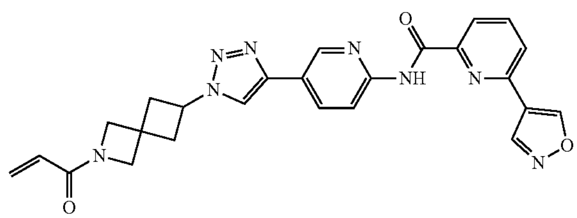 [SMILES: C=CC(=O)N1CC2(CC(n3cc(-c4ccc(NC(=O)c5cccc(-c6cnoc6)n5)nc4)nn3)C2)C1]

N-(5-(1-(2-acryloyl-2-azaspiro[3,3]heptan-6-yl)-1H-1,2,3-triazol-4-yl)pyridin-2-yl)-6-(isoxazol-4-yl) picolinamide (024)

Prepared according to the procedure for 029 to give 1 mg of product in 5% yield. m/z expected: 482.5, observed: 483.17

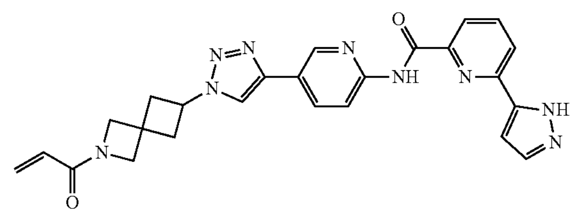 [SMILES: C=CC(=O)N1CC2(CC(n3cc(-c4ccc(NC(=O)c5cccc(-c6ccn[nH]6)n5)nc4)nn3)C2)C1]

N-(5-(1-(2-acryloyl-2-azaspiro[3,3]heptan-6-yl)-1H-1,2,3-triazol-4-yl)pyridin-2-yl)-6-(1H-pyrazol-4-yl) picolinamide (025)

Prepared according to the procedure for 10 to give 14 mg of product in 49% yield. m/z expected: 481.52, observed: 481.86.

Example 8: Preparation of Compounds 013 and 038

Scheme 8.

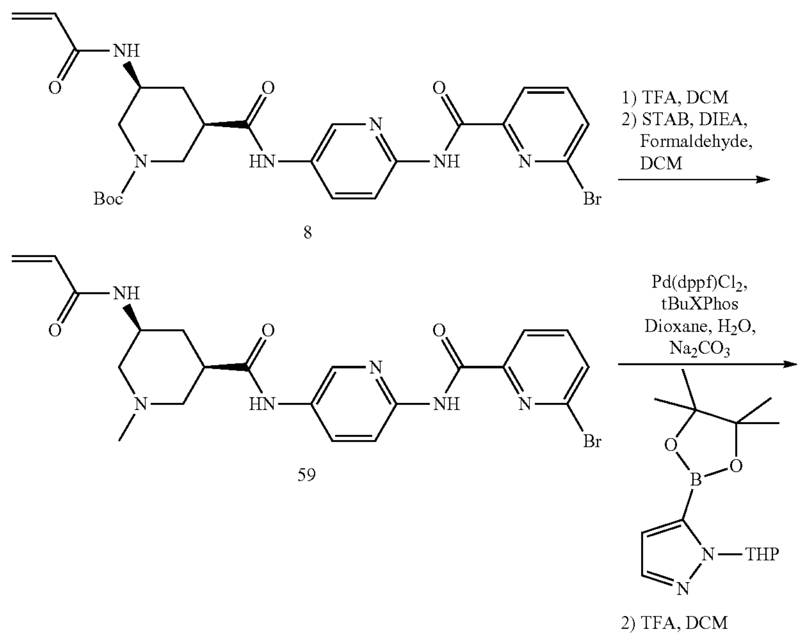

-continued

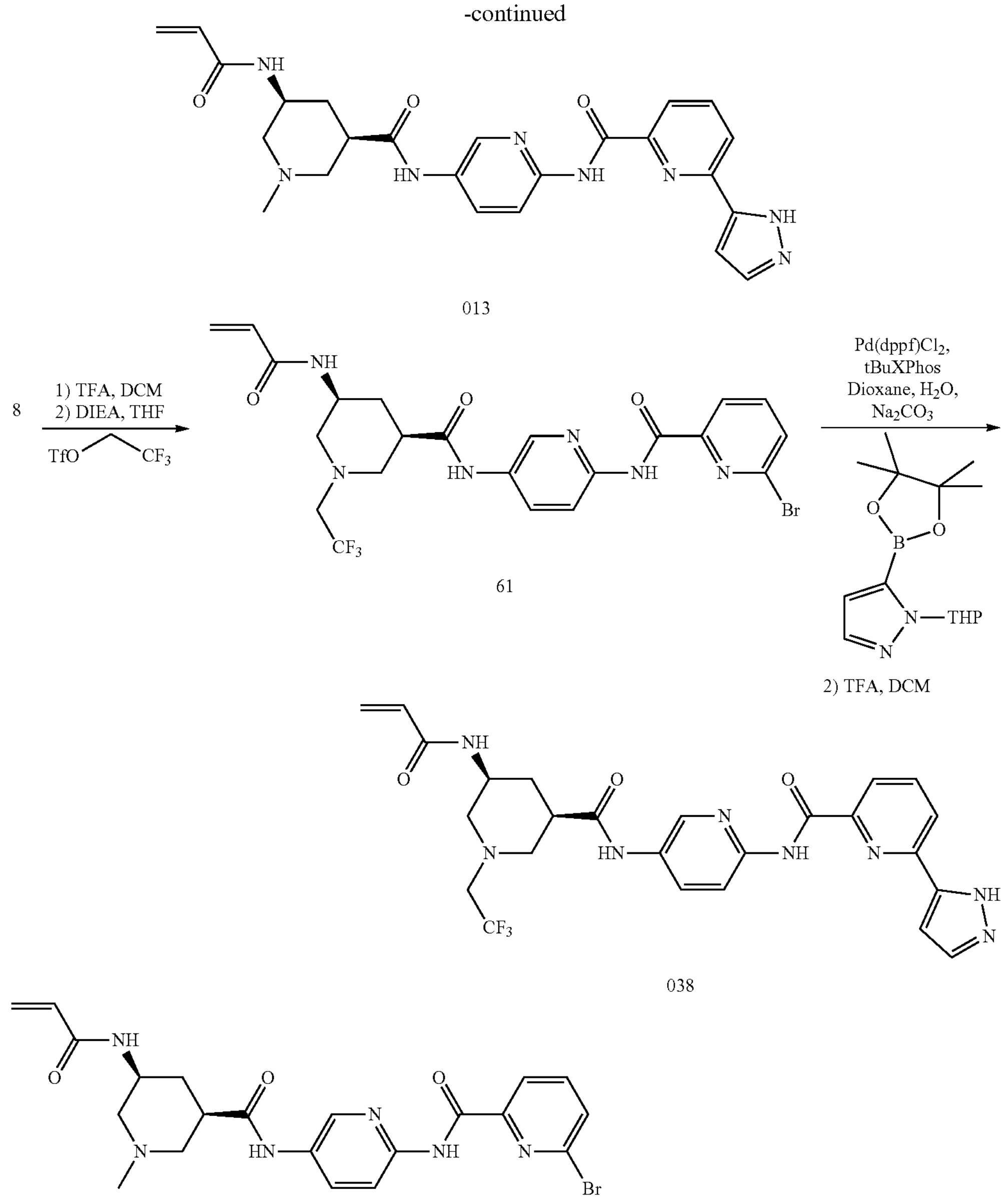

013

8

61

038

N-(5-((3R,5S)-5-acrylamido-1-methylpiperidine-3-carboxamido)pyridin-2-yl)-6-bromopicolinamide (59)

To a stirred solution of 8 (200 mg, 0.35 mmol) in DCM (10 mL) was added TFA (1 mL). The reaction mixture was stirred for 30 minutes at room temperature, and the solvent was removed. The mixture was dissolved in DOM (10 mL). DIVA (610 µL, 3.5 mmol) was added followed by formaldehyde 37% aq soln (142 µL, 1.75 mmol). The mixture was stirred for 10 minutes, then sodium triacetoxyborohydride (222 mg, 1.05 mmol) was added and the mixture stirred for 2 hr at rt. The reaction was quenched with sat aq $NaHCO_3$ and extracted with DOM. The combined organic layer was dried over $MgSO_4$, filtered and condensed to give 59 a brown oil that was used without further purification, m/z expected: 487.36, observed: 488.74

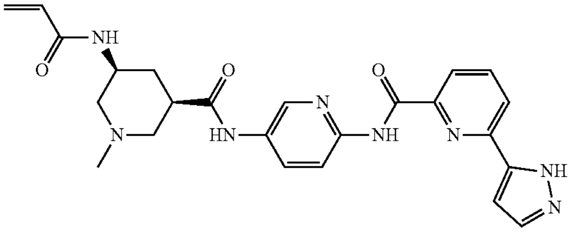 [SMILES: C=CC(=O)N[C@H]1C[C@@H](C(=O)Nc2ccc(NC(=O)c3cccc(-c4ccn[nH]4)n3)nc2)CN(C)C1]

N-(5-((3R,5S)-5-acrylamido-1-methylpiperidine-3-carboxamido)pyridin-2-yl)-6-(1H-pyrazol-5-yl)picolinamide (013)

The same procedure for 10 was followed to give 12 mg of the product in 38% yield. m/z expected: 474.53, observed: 475.26. $^1$H NMR (500 MHz DMSO) δ 11.03 (s, 1H), 10.51

(s, 1H), 9.98 (s, 1H), 8.67 (s, 1H), 8.44 (d, J=7.9 Hz, 1H), 8.28 (d, J=8.8 Hz, 1H), 8.16-8.09 (m, 3H), 8.07 (dd, J=8.9 Hz, 2.9 Hz, 1H), 7.74 (s, 1H), 7.05 (s, 1H), 6.27-6.19 (m, 1H), 6.15 (dd, J=17.1 Hz, 2.6 Hz, 1H), 5.68 (dd, J=9.7 Hz, 2.7 Hz, 1H), 3.03-2.98 (m, 2H), 2.90 (s, 3H), 2.77 (s, 2H), 2.27-2.24 (m, 2H), 1.62-1.55 (m, 2H).

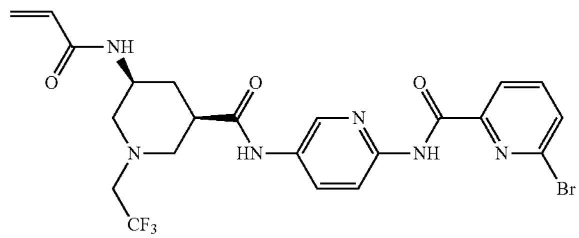 [SMILES: C=CC(=O)N[C@H]1C[C@@H](C(=O)Nc2ccc(NC(=O)c3cccc(Br)n3)nc2)CN(CC(F)(F)F)C1]

N-(5-((3R,5S)-5-acrylamido-1-(2,2,2-trifluoroethyl) piperidine-3-carboxamido)pyridin-2-yl)-6-bromopicolinamide (61)

To a stirred solution of 8 (200 mg, 0.35 mmol) in DCM (10 mL) was added TEA (1 mL). The reaction mixture was stirred for 30 minutes at room temperature, and the solvent was removed. The mixture was dissolved in THE (10 mL). DIEA (610 μL, 3.5 mmol) was added followed by 2,2,2-trifluoroethyl trifluoromethanesulfonate (252 μL, 1.75 mmol). The mixture was stirred for 2 hr at rt. The reaction was quenched with sat aq $NaHCO_3$ and extracted with EtOAc. The combined organic layer was dried over $MgSO_4$, filtered and condensed to give 61 a brown oil that was used without further purification. m/z expected: 555.36, observed: 556.43

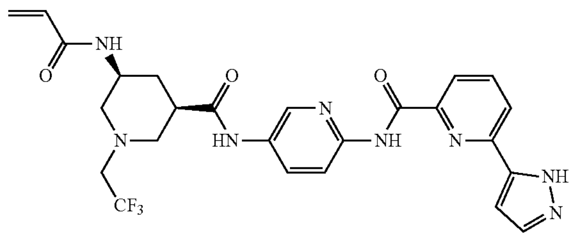 [SMILES: C=CC(=O)N[C@H]1C[C@@H](C(=O)Nc2ccc(NC(=O)c3cccc(-c4ccn[nH]4)n3)nc2)CN(CC(F)(F)F)C1]

N-(5-((3R,5S)-5-acrylamido-1-(2,2,2-trifluoroethyl) piperidine-3-carboxamido)pyridin-2-yl)-6-(1H-pyrazol-5-yl)picolinamide (038)

The same procedure for 10 was followed to give 32 mg of the product in 46% yield. m/z expected: 542.52, observed: 543.19. $^1H$ NMR (500 MHz DMSO) δ 11.03 (s, 1H), 10.30 (s, 1H), 8.70 (s, 1H), 8.25 (d, J=8.9 Hz, 2H), 8.14-8.10 (m, 4H), 8.07 (dd, J=9.0 Hz, 2.7 Hz, 1H), 7.74 (s, 1H), 7.06 (s, 1H), 6.22-6.17 (m, 1H), 6.10 (dd, J=17.2 Hz, 2.5 Hz, 1H), 5.61 (dd, J=10 Hz, 2.4 Hz, 1H), 3.36-3.27 (m, 3H), 3.12-3.03 (m, 3H), 2.77-2.72 (m, 1H), 2.16-2.12 (m, 1H), 2.04-2.02 (m, 1H), 1.49-1.41 (m, 1H).

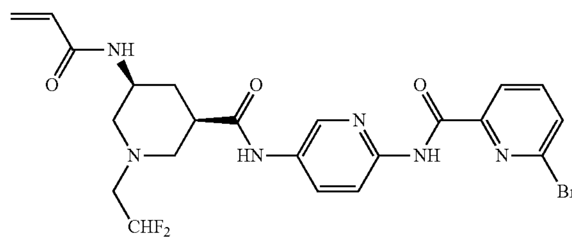

N-(54(3R,5S)-5-acrylamido-1-(2,2-difluoroethyl) piperidine-3-carboxamido)pyridin-2-yl)-6-bromopicolinamide (63)

Prepared following the same procedure used for 61 using 2,2-difluoroethyl trifluoromethanesulfonate to give a brown oil that was used without further purification. m/z expected: 537.37, observed: 538.61

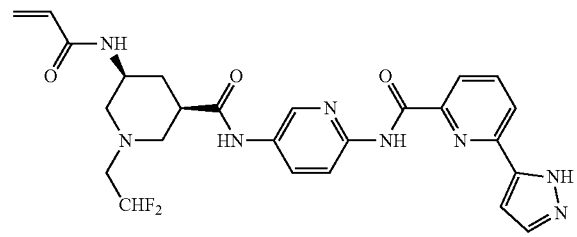 [SMILES: C=CC(=O)N[C@H]1C[C@@H](C(=O)Nc2ccc(NC(=O)c3cccc(-c4ccn[nH]4)n3)nc2)CN(CC(F)F)C1]

N-(5-((3R,5S)-5-acrylamido-1-(2,2-difluorethyl) piperidine-3-carboxamido)pyridin-2-yl)-6-(1H-pyrazol-5-yl)picolinamide (039)

The same procedure for 10 was followed to give 46 mg of the product in 57% yield. m/z expected: 524.53, observed: 525.67. $^1H$ NMR (500 MHz DMSO) δ 11.04 (s, 1H), 10.39 (s, 1H), 8.68 (s, 1H), 8.26 (d, J=8.8 Hz, 1H), 8.15-8.09 (m, 4H), 8.07 (dd, J=9.0 Hz, 2.7 Hz, 1H), 7.74 (s, 1H), 7.06 (s, 1H), 6.23-6.18 Om 1H), 6.13 (dd, J=17.1 Hz, 2.6 Hz, 1H), 5.64 (dd, J=9.8 Hz, 2.5 Hz, 1H), 3.27 (s, 1H), 2.89 (m, 2H), 2.71 (s, 1H), 2.14-2.11 (m, 1H), 1.75-1.68 (m, 1H), 1.56-1.49 (m, 2H), 1.44-1.38 (m, 2H), 1.35-1.3 (m, 1H).

Example 9: Biological Assays

To measure the 050 values of compounds herein against IRAK4, a Z'-LYTE assay (ThermoFisher) was used. Briefly, 2.5 μL. of different concentrations of the compounds in 1% DMSO were added to 2.4 μL kinase buffer (50 mM HEPES pH 7.5, 0.01% BRIJ-35, 10 mM $MgCl_2$, 1 mM EGTA) in each well of a 384-well plate (Corning Cat. #3676). 5 μL of 2×IRAK4/Ser/Thr 07 mixture (prepared in 50 mM HEPES pH 7.5, 0.01% BRIJ-35, 10 mM $MnCl_2$, 2 mM OTT, and 0.02% $NaN_3$) and 2.5 μL of 4×ATP solution (4×ATP, 50 mM HEPES, pH 7.5, 0.01% BRIJ-35, 10 mM $MgCl_2$, 1 mM EGTA) were added to each well. The plate was shaken for 30 seconds, and then incubated at room temperature for 60 minutes. 5 μL of a 1:100000 dilution of Development Reagent A was added to each well. The plate was shaken for 30 seconds and incubated for 60 minutes at room temperature. The plate was subsequently read on a fluorescence plate reader, and the emissions ratio was calculated to determine the ratio of Ser/Thr 07 phosphorylated by the reaction. Emissions Ratio=Coumarin Emission (443 nm)/Flourescein Emission (520 nm).

To measure the $IC_{50}$ values of the compounds herein against IRAK1, the Adapta Universal Kinase Assay (ThermoFisher) was used. Briefly, 100 nL of different concentrations of the compounds in 100% DMSO were added to each well of a 384-well plate (Corning Cat. #4512). 2.4 μL of 30 mM HEPES, 2.5 μL of 4×ATP solution (in water), and 5 μL of 2× IRAK1/Histone H3 (1-20) peptide mixture (prepared in 50 mM HEPES pH 7.5, 0.01% BRIJ-35, 10 mM $MgCl_2$, 1 mM EGTA) were added to each well. The plate was shaken for 30 seconds and centrifuged for 1 minute at 1000×g. The plate was then incubated at room temperature for 60 minutes. 5 μL of Detection Mix was added to each well. The plate was shaken for 30 seconds and centrifuged for 1 minute at 1000×g. The plate was then incubated at room temperature for 60 minutes. The plate was subsequently read on a fluorescence plate reader, and the emissions ratio was calculated to determine the ratio of ATP to ADP. Emissions Ratio=AF647 Emission (665 nm)/Europium Emission (615 nm).

The data obtained from these assays are shown in Table 2 below.

TABLE 2

| Compound No. | IRAK1 $IC_{50}$ (nM) | IRAK4 $IC_{50}$ (nM) |
|---|---|---|
| 001 | 129 | >10,000 |
| 002 | 257 | >10,000 |
| 003 | 671 | >10,000 |
| 005 | 189 | >10,000 |
| 006 | 14 | 4000 |
| 007 | 150 | >10,000 |
| 013 | 18.5 | >10,000 |
| 016 | 301 | 9,930 |
| 024 | 612 | 3,330 |
| 025 | 26.6 | 1,630 |
| 026 | 68.1 | >10,000 |
| 027 | 6.37 | 1,870 |
| 028 | 12.5 | 722 |
| 029 | 658 | >10,000 |
| 030 | 399 | 3,330 |
| 031 | 40.1 | 1,110 |
| 032 | 1,190 | >10,000 |
| 033 | 74.2 | 2,510 |
| 034 | 344 | 2,010 |
| 038 | 12.1 | >10,000 |
| 039 | 14.9 | >10,000 |

Various modifications of the invention, in addition to those described herein, will be apparent to those skilled in the art from the foregoing description. Such modifications are also intended to fail within the scope of the appended claims. Each reference, including without limitation all patent, patent applications, and publications, cited in the present application is incorporated herein by reference in its entirety.

The invention claimed is:

1. A compound of Formula I:

(I)

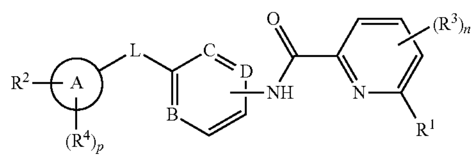

or a pharmaceutically acceptable salt thereof;

wherein

A is piperidinyl;

B is CH or $CR^5$;

C is CH;

D is N;

L is selected from the group consisting of

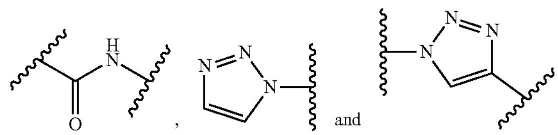

$R^1$ is pyrazole or isoxazole optionally substituted one or two times with $R^8$;

$R^3$ is selected from the group consisting of halogen, $C_1$-$C_6$ alkyl, $C(O)C_1$-$C_6$ alkyl, $C_2$-$C_6$ alkenyl, $C_2$-$C_6$ alkynyl, 3-8 membered cycloalkyl, 3-8 membered heterocycloalkyl, 6-10 membered aryl, 5-10 membered heteroaryl, $OR^9$, $N(R^9)_2$, and $SR^9$, wherein alkyl, alkenyl, alkynyl, cycloalkyl, heterocycloalkyl, aryl, and heteroaryl are optionally substituted with one, two, or three $R^9$;

$R^4$ is independently, at each occurrence, selected from the group consisting of hydrogen, halogen, and $C_1$-$C_2$ alkyl, wherein alkyl is optionally substituted with one, two, or three fluorine atoms;

$R^5$ is selected from the group consisting of halogen, $C_1$-$C_6$ alkyl, $C(O)C_1$-$C_6$ alkyl, $C_2$-$C_6$ alkenyl, $C_2$-$C_6$ alkynyl, $OR^9$, $N(R^9)_2$, and $SR^9$, wherein alkyl is optionally substituted with one, two, or three halogen;

$R^8$ is selected from the group consisting of $C_1$-$C_6$ alkyl, OH, CN, $NO_2$, halogen, $C_1$-$C_6$ alkoxy, and $C_1$-$C_6$ alkylamine, wherein alkyl is optionally substituted one, two, or three times with halogen, OH, and $NH_2$;

$R^9$ is independently, at each occurrence, selected from the group consisting of hydrogen, halogen, $C_1$-$C_6$ alkyl, $C(O)C_1$-$C_6$ alkyl, $C_2$-$C_6$ alkenyl, $C_2$-$C_6$ alkynyl, 3-8 membered cycloalkyl, 3-8 membered heterocycloalkyl, 6-10 membered aryl, and 5-10 membered heteroaryl;

alternatively, two $R^9$, together with the atoms to which they are attached form a 3-8 membered heterocycloalkyl;

$R^2$ is

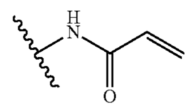

n is 0 or 1; and p is 0, 1, or 2.

2. The compound of claim 1, wherein the compound of Formula I is a compound of Formula IV:

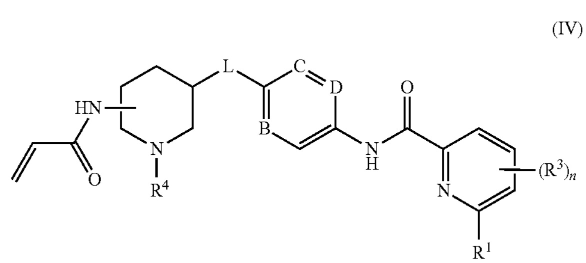

(IV)

or a pharmaceutically acceptable salt thereof.

3. The compound of claim 1, wherein the compound of Formula I is a compound of Formula IVa:

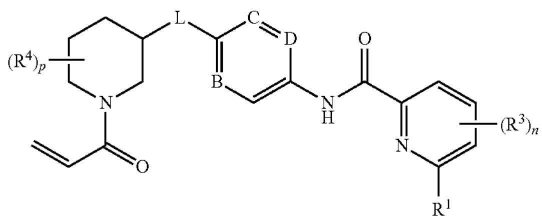

(IVa)

or a pharmaceutically acceptable salt thereof.

4. The compound of claim 1, wherein B is CH.

5. The compound of claim 1, wherein B is $CR^5$.

6. The compound of claim 1, wherein the compound of Formula I is selected from the group consisting of

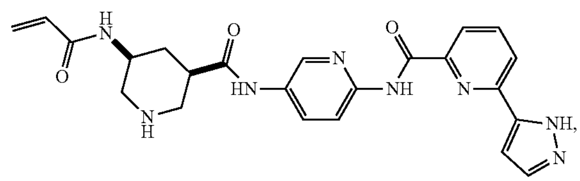

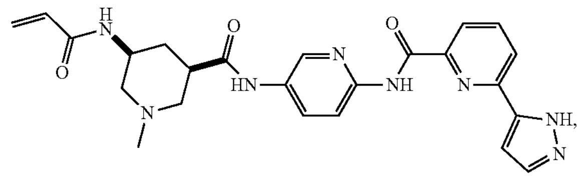

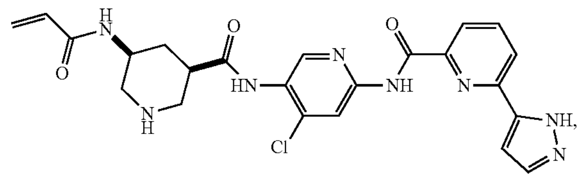

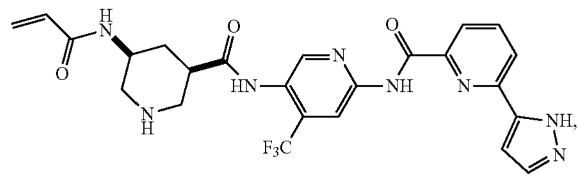

-continued

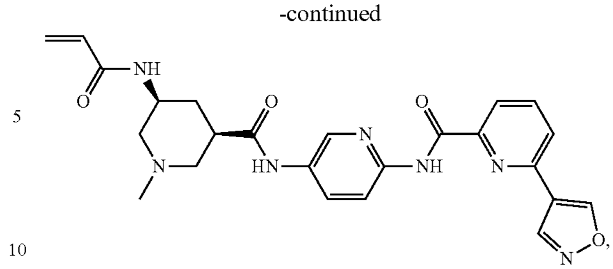

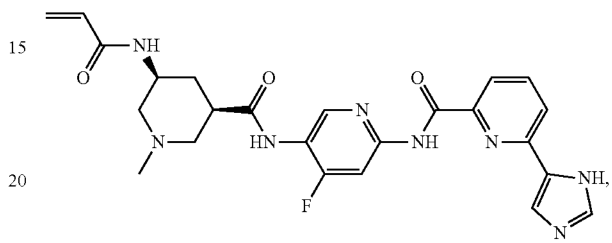

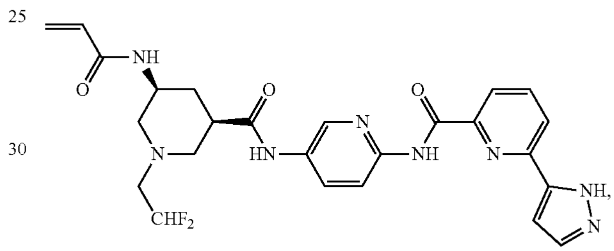

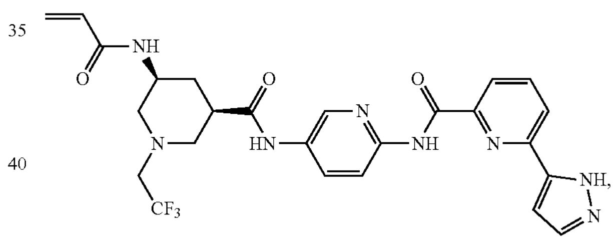

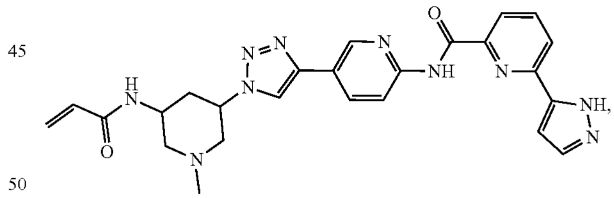

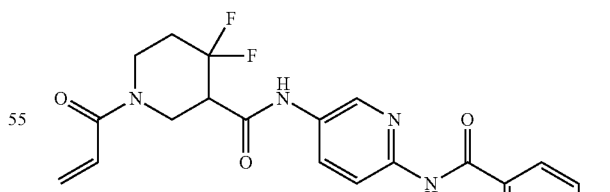

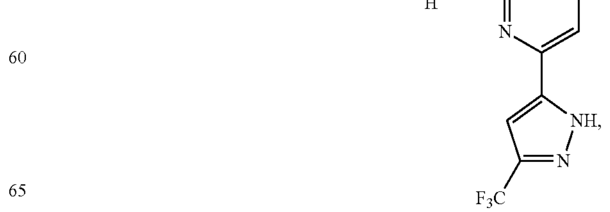

-continued
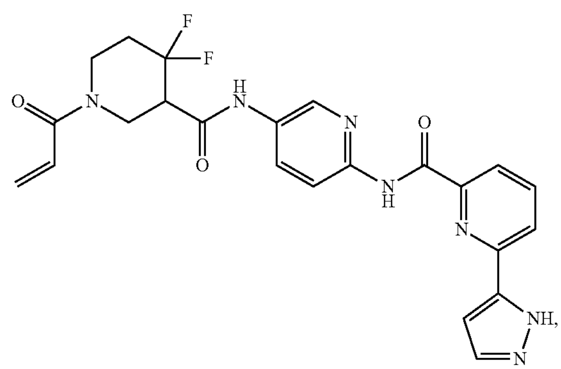
,
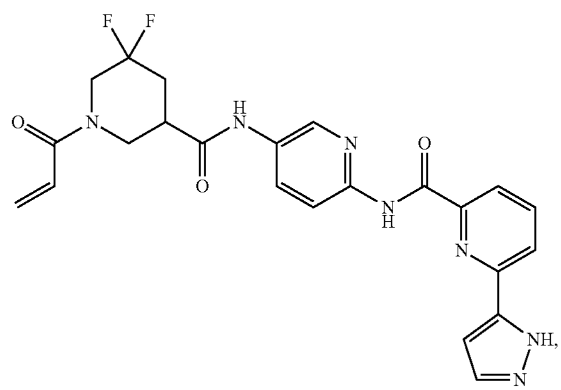
,
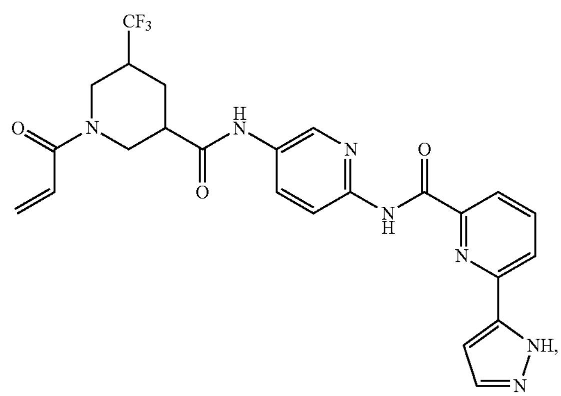
,
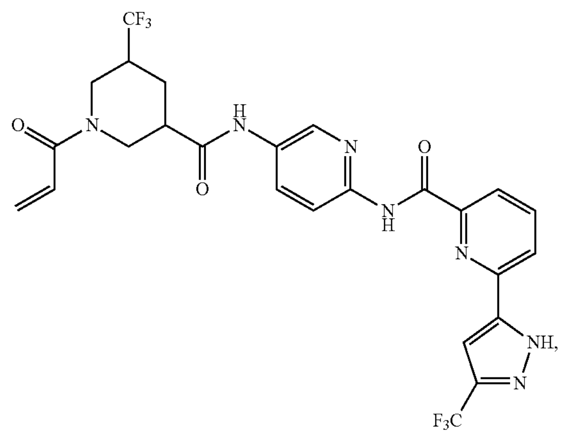
,
-continued
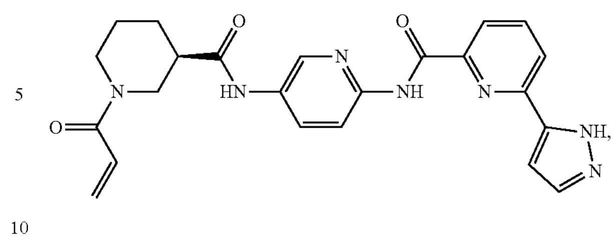
,
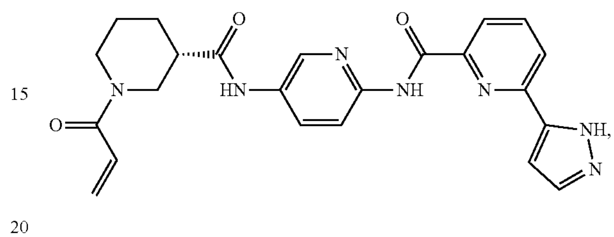
,
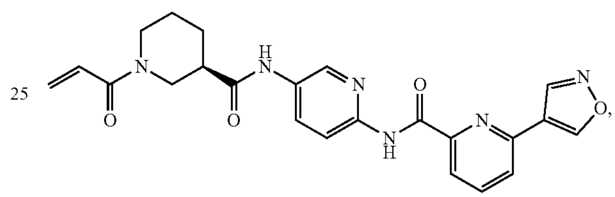
,
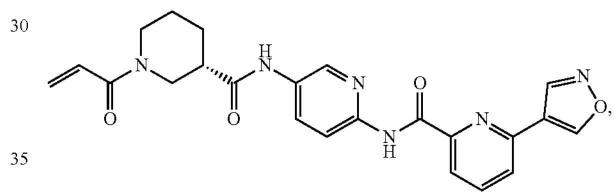
,
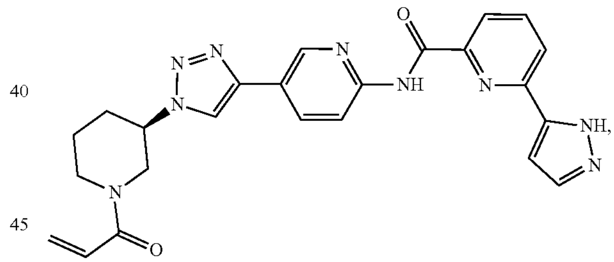
,
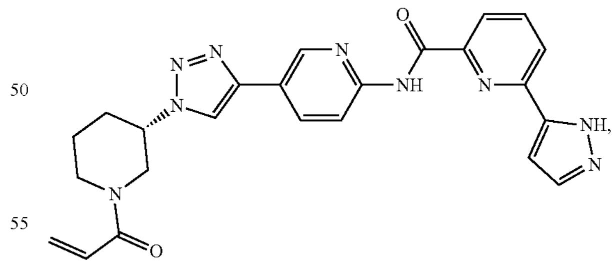
,
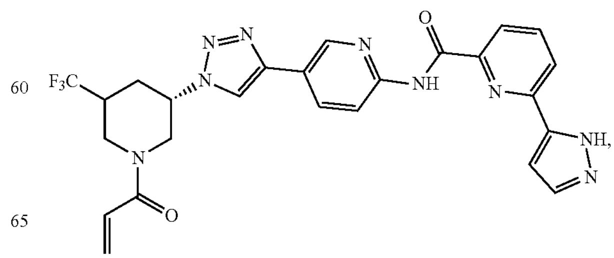
, -continued

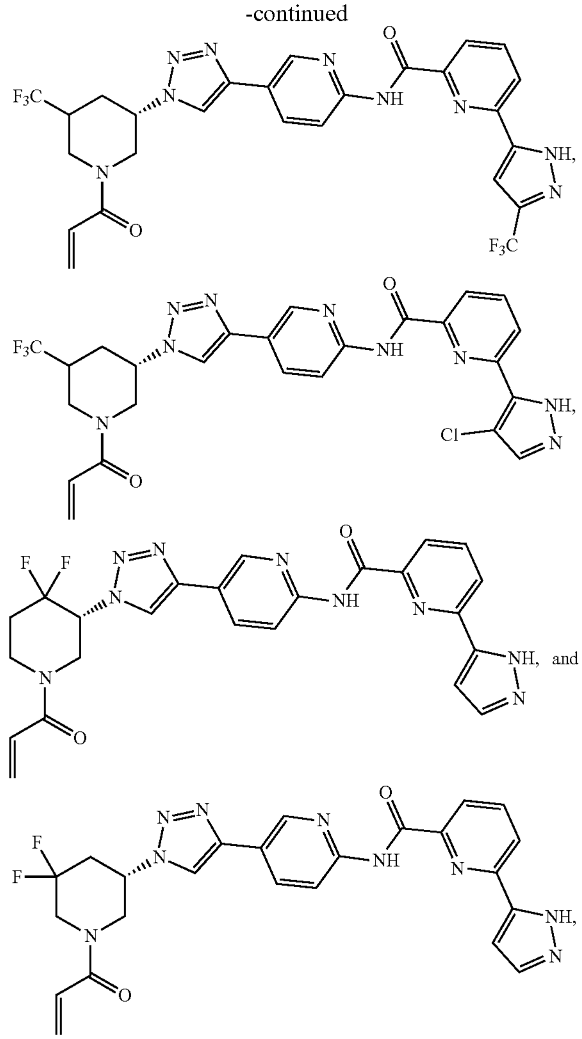

and or a pharmaceutically acceptable salt thereof.

7. A pharmaceutical composition comprising a compound of claim 1, or a pharmaceutically acceptable salt thereof, and a pharmaceutically acceptable carrier.

8. A method of inhibiting interleukin-1 receptor-associated kinase 1 (IRAK1) in a subject in need thereof comprising administering to the subject a therapeutically effective amount of a compound of claim 1.

9. A method of treating a proliferative disease associated with overexpression, aberrant activity, or increased activity of interleukin-1 receptor-associated kinase (IRAK) in a subject in need thereof comprising administering to the subject a therapeutically effective amount of a compound of claim 1.

10. The method of claim 9, wherein the proliferative disease is associated with overexpression of interleukin-1 receptor-associated kinase 1 (IRAK1) or interleukin-1 receptor-associated kinase 4 (IRAK4).

11. The method of claim 10, wherein the proliferative disease is cancer, an inflammatory disease, or an autoimmune disease.

12. The method of claim 11, wherein the proliferative disease is cancer.

13. The method of claim 12, wherein the cancer is selected from the group consisting of breast cancer, Waldenström macroglobulinemia, myelodysplastic syndrome (MDS), leukemia, and lymphoma.

14. The method of claim 12, wherein the cancer is triple-negative breast cancer (TNBC) or acute myeloid leukemia (AML).

15. The method of claim 12, wherein the cancer is acute myeloid leukemia (AML).

16. The method of claim 9, wherein the method further comprises administering a second pharmaceutical agent.

17. The method of claim 16, wherein the second pharmaceutical agent is a Bruton's tyrosine kinase (BTK) inhibitor.

* * * * *